(12) United States Patent
Shoseyov et al.

(10) Patent No.: US 8,759,487 B2
(45) Date of Patent: Jun. 24, 2014

(54) METHODS OF PROCESSING RECOMBINANT PROCOLLAGEN

(75) Inventors: Oded Shoseyov, Karmei Yosef (IL); Hanan Stein, Nes-Ziona (IL); Michal Rosenthal, Holon (IL); Or Dgany, Ashdod (IL); Tamar Haya Tal, Gan-Yavne (IL); Amit Yaari, Kibbutz Ein Dror Doar-Na Yizrael (IL)

(73) Assignee: CollPlant Ltd., Nes Ziona (IL)

( * ) Notice: Subject to any disclaimer, the term of this patent is extended or adjusted under 35 U.S.C. 154(b) by 205 days.

(21) Appl. No.: 12/739,192

(22) PCT Filed: Oct. 26, 2008

(86) PCT No.: PCT/IL2008/001408
§ 371 (c)(1),
(2), (4) Date: Apr. 22, 2010

(87) PCT Pub. No.: WO2009/053985
PCT Pub. Date: Apr. 30, 2009

(65) Prior Publication Data
US 2012/0065376 A1    Mar. 15, 2012

Related U.S. Application Data

(60) Provisional application No. 60/996,084, filed on Oct. 26, 2007.

(51) Int. Cl.
*A61K 38/17* (2006.01)
(52) U.S. Cl.
USPC ........................................................ 530/356
(58) Field of Classification Search
None
See application file for complete search history.

(56) References Cited

U.S. PATENT DOCUMENTS

| 4,488,911 | A  |   | 12/1984 | Luck et al. |
| 5,670,369 | A  |   | 9/1997  | Fink et al. |
| 6,617,431 | B1 |   | 9/2003  | Gruber et al. |
| 6,713,662 | B1 | * | 3/2004  | Karatzas et al. ............... 800/14 |

FOREIGN PATENT DOCUMENTS

| DE  | 2462222       | A | * | 5/1976 |
| WO  | WO 2006/035442 |   |   | 4/2006 |
| WO  | WO 2009/053985 |   |   | 4/2009 |

OTHER PUBLICATIONS

Herman et al., "Protein Storage Bodies and Vacuoles", The Plant Cell, vol. 11, 601-613, Apr. 1999.*
Machine Translation of DE 2462 2222 A (May 1976).*
Derwent Abstract for DE 2462 2222 A (May 1976).*
International Search Report Dated Feb. 27, 2009 From the International Searching Authority Re.: Application No. PCT/IL2008/001408.
Written Opinion Dated Feb. 27, 2009 From the International Searching Authority Re.: Application No. PCT/IL2008/001408.
Bulleid et al. "Recombinant Expression System for the Production of Collagen", Biochemical Society Transactions, 28(Pt.4): 350-353, 2000.
Horn et al. "Plant Molecular Farming: Systems and Products", Plant Cell Reports, XP002514486, 22(10): 711-720, May 2004. p. 714, 716.
Hulmes "Building Collagen Molecules, Fibrils, and Suprafibrillar Structures", Journal of Structural Biology, 137: 2-10, 2002.
Khoshnoodi et al. "Molecular Recognition in the Assembly of Collagens: Terminal Noncollagenous Domains Are Key Recognition Modules in the Formation of Triple Helical Protomers", The Journal of Biological Chemistry, 281(50): 38117-38121, Dec. 15, 2006.
Klee et al. "Agrobacterium-Mediated Plant Transformation and Its Further Applications to Plant Biology", Annual Review of Plant Physiology, 38: 467-486, 1987.
Merle et al. "Hydroxylated Human Homotrimeric Collagen T in Agrobacterium Tumefaciens-Mediated Transient Expression and in Transgenic Tobacco Plant", FEBS Letters, 515: 114-118, 2002.
Olsen et al. "Recombinant Collagen and Gelatin for Drug Delivery", Advanced Drug Delivery Reviews, XP002368792, 55(12): 1547-1567, Nov. 28, 2003. p. 1550, col. 2, § 2-p. 1554, col. 2, § 2, p. 1550, col. 1, § 3, p. 1551, col. 1, § 1-2, p. 1554, col. 1, § 1, p. 1556, col. 1, § 2.
Pope et al. "Molecular Abnormalities of Collagen: A Review", Journal of the Royal Society of Medicine, XP002514485, 76(12): 1050-1062, Dec. 1983. p. 1050.
Potrykus "Gene Transfer to Plants: Assessment of Published Approaches and Results", Annual Review of Plant Physiology and Plant Molecular Biology, 42: 205-225, 1991.
Ruggiero et al. "Triple Helix Assembly and Processing of Human Collagen Produced in Transgenic Tobacco Plants", FEBS Letters, 469: 132-136, 2000.
Shimamoto et al. "Fertile Transgenic Rice Plants Regenerated From Transformed Protoplasts", Nature, 338: 274-276, Mar. 16, 1989.
Vaughan et al. "Production of Recombinant Hydroxylated Human Type III Collagen Fragment in *Saccharomyces cerevisiae*", DNA and Cell Biology, XP000961111, 17(6): 511-518, Jan. 1, 1998.
Wang et al. "The Third Activity for Lysyl Hydroxylase 3: Galactosylation of Hydroxylysyl Residues in Collagens In Vitro", Matrix Biology, 21: 559-566, 2002.
International Preliminary Report on Patentability Dated May 6, 2010 From the International Bureau of WIPO Re.: Application No. PCT/IL2008/001408.
Communication Pursuant to Article 94(3) EPC Dated Aug. 29, 2011 From the European Patent Office Re. Application No. 08841256.4.
Response Dated Dec. 25, 2011 to Communication Pursuant to Article 94(3) EPC of Aug. 29, 2011 From the European Patent Office Re. Application No. 08841256.4.

(Continued)

*Primary Examiner* — Suzanne M Noakes

(57) ABSTRACT

A method of generating atelocollagen is disclosed. The method comprises contacting a human telopeptide-comprising collagen with a protease selected from the group consisting of neutrase, subtilisin, ficin recombinant human trypsin and recombinant human pepsin, wherein said human telopeptide-comprising collagen is expressed in a non-animal cell, thereby generating the atelocollagen. Compositions comprising the atelocollagen generated thereby are also disclosed.

4 Claims, 16 Drawing Sheets
(16 of 16 Drawing Sheet(s) Filed in Color)

(56) References Cited

OTHER PUBLICATIONS

Office Action Dated Mar. 12, 2012 From the Israel Patent Office Re. Application No. 205270 and Its Translation Into English.
Communication Pursuant to Article 94(3) EPC Dated Sep. 25, 2012 From the European Patent Office Re. Application No. 08841256.4.
Office Action Dated Oct. 10, 2012 From the Israel Patent Office Re. Application No. 205270 and Its Translation Into English.
Office Action Dated Jun. 30, 2013 From the Israel Patent Office Re. Application No. 205270 and Its Translation Into English.
Communication Pursuant to Article 94(3) EPC Dated Jan. 30, 2014 From the European Patent Office Re. Application No. 08841256.4.

* cited by examiner

METHODS OF PROCESSING RECOMBINANT PROCOLLAGEN

RELATED APPLICATIONS

This Application is a National Phase of PCT Patent Application No. PCT/IL2008/001408 having International filing date of Oct. 26, 2008, which claims the benefit of U.S. Provisional Patent Application No. 60/996,084 filed on Oct. 26, 2007. The contents of the above Applications are all incorporated herein by reference.

FIELD AND BACKGROUND OF THE INVENTION

The present invention relates to a method of processing recombinant procollagen.

Collagens are the main proteins responsible for the structural integrity of vertebrates and many other multicellular organisms. Type I collagen represents the prototypical fibrillar collagen and is the major collagen type in most tissues, including bone, tendon, skin, aorta, and lung. Type I collagen fibers provide for great tensile strength and limited extensibility.

Collagen provides biomaterials with characteristics necessary for a myriad of applications including pharmaceutical (haemostatic compresses, sponges, healing dressings), medical (prostheses such as cardiac valves, tendons and ligaments, skin substitutes, filling agents), odontological (gum implants) and cosmetic (additive, anti-wrinkling agent, microcontainer for perfumed substances). The collagen-based products manufactured in all of the aforementioned markets require vast amounts of raw collagen materials for their production.

The conformation and most of the properties of native collagen are determined by the triple helix domain which composes more than 95% of the molecule. This domain consists of three alpha chains, each containing approximately 1,000 amino acids, wrapped in a rope-like fashion to form a tight, triple helix structure. The triple helix is wound in such a way that peptide bonds linking adjacent amino acids are buried within the interior of the molecule, such that the collagen molecules are resistant to attack by proteases, such as pepsin.

In all of the fibrillar collagen molecules, the three polypeptide chains are constructed from repeating Gly-X-Y triplets, where X and Y can be any amino acid but are frequently the imino acids proline and hydroxyproline. An important feature of fibril-forming collagens is that they are synthesized as precursor procollagens containing globular N- and C-terminal extension propeptides. The triconstituent polypeptide chains are assembled within the rough endoplasmic reticulum to form procollagen. As the polypeptide chain is co-translationally translocated across the membrane of the endoplasmic reticulum, prolyl-4-hydroxylase (P4H)-dependent hydroxylation of proline and lysine residues occurs within the Gly-X-Y repeat region. The stability of the final triple-helical structure of collagen is highly dependent on the P4H-mediated hydroxylation of collagen chains. Lysyl hydroxylase (LH, EC 1.14.11.4), galactosyltransferase (EC 2.4.1.50) and glucosyltransferase (EC 2.4.1.66) are enzymes involved in posttranslational modifications of collagens. They sequentially modify lysyl residues in specific positions to hydroxylysyl, galactosylhydroxylysyl and glucosylgalactosyl hydroxylysyl residues. These structures are unique to collagens and essential for their functional activity (Wang et al, 2002, Matrix Biol. November; 21(7):559-66). A single human enzyme, Lysyl hydroxylase 3 (LH3) can catalyze all three consecutive steps in hydroxylysine linked carbohydrate formation (Wang et al, 2002, Matrix Biol. November; 21(7): 559-66). Once the polypeptide chain is fully translocated into the lumen of the endoplasmic reticulum the three pro-alpha chains associate via their C-propeptides to form a trimeric molecule where the Gly-X-Y repeat region forms a nucleation point at its C-terminal end, ensuring correct alignment of the chains. The Gly-X-Y region then folds in a C-to-N direction to form a triple helix (J. Khoshnoodi. et. al, J. Biol. Chem. 281, 38117-38121, 2006)

The C-propeptides (and to a lesser extent the N-propeptides) keep the procollagen soluble during its passage out of the cell (Bulleid et al., 2000, Biochem Soc Trans; 28(4):350-3). Following or during secretion of procollagen molecules into the extracellular matrix, propeptides are typically removed by procollagen N- and C-proteinases, thereby triggering spontaneous self-assembly of collagen molecules into fibrils (Hulmes, 2002, J Struct Biol. January-February; 137 (1-2):2-10). Removal of the propeptides by procollagen N- and C-proteinases lowers the solubility of procollagen by >10000-fold and is necessary to initiate the self-assembly of collagen into fibers at 37° C. Crucial to this assembly process are the short telopeptides which are the nontriple-helical remnants of the N- and C-terminal propeptides remaining after digestion with N/C proteinases. These peptides act to ensure correct covalent registration of the collagen molecules within the fibril structure and lower the critical concentration required for self-assembly (Bulleid et al., 2000, Biochem Soc Trans; 28(4):350-3) through their crosslinkable aldehydes.

Native collagen is generally present in connective tissue as telopeptide-containing collagen molecules packed side by side in the form of fibrils. Each longitudinal course is composed of molecules aligned in end-to-end dispositions with slight longitudinal spaces staggered relative to the next successive laterally adjacent longitudinal course. In this way, gaps are generated between facing end regions of successive molecules in a given longitudinal course and bound by the staggered sides of the molecules in the parallel longitudinal courses laterally adjacent thereto.

Dispersal and solubilization of native animal collagen can be achieved using various proteolytic enzymes which disrupt the intermolecular bonds and remove the immunogenic non-helical telopeptides without affecting the basic, rigid triple-helical structure which imparts the desired characteristics of collagen (see U.S. Pat. Nos. 3,934,852; 3,121,049; 3,131, 130; 3,314,861; 3,530,037; 3,949,073; 4,233,360 and 4,488, 911 for general methods for preparing purified soluble collagen). The resulting soluble atelocollagen can be subsequently purified by repeated precipitation at low pH and high ionic strength, followed by washing and re-solublization at low pH. Nevertheless, the soluble preparation is typically contaminated with crosslinked collagen chains which decrease the homogeneity of the protein preparation.

The use of animal-derived collagen is problematic due to the possible risks of contamination by non-conventional infectious agents. While the risks raised by bacterial or viral contamination can be fully controlled, prions are less containable and present considerable health risks. These infectious agents which appear to have a protein-like nature, are involved in the development of degenerative animal encephalopathy (sheep trembling disease, bovine spongiform encephalopathy) and human encephalopathy (Creutzfeld-Jacob disease, Gerstmann-Straussler syndrome, and kuru disease). Due to the lengthy time before onset of the disease, formal controls are difficult to conduct.

Plants expressing collagen chains are known in the art, see for example, WO06035442A3; Merle et al., FEBS Lett. 2002

Mar. 27; 515(1-3):114-8. PMID: 11943205; and Ruggiero et al., 2000, FEBS Lett. 2000 Mar. 3; 469(1):132-6. PMID: 10708770; and U.S. Pat. Applications 2002/098578 and 2002/0142391 as well as U.S. Pat. No. 6,617,431.

U.S. Pat. Nos. 4,597,762, 5,670,369, 5,316,942, 5,997,895 and 5,814,328 teach processing of animal derived "insoluble collagen" with plant derived proteases such as ficin and/or papain.

SUMMARY OF THE INVENTION

According to an aspect of some embodiments of the present invention there is provided a method of generating atelocollagen, the method comprising contacting a human telopeptide-comprising collagen with a protease selected from the group consisting of neutrase, subtilisin, ficin, recombinant human trypsin and recombinant human pepsin, wherein the human telopeptide-comprising collagen is expressed in a non-animal cell, thereby generating the atelocollagen.

According to an aspect of some embodiments of the present invention there is provided a composition-of-matter comprising a human atelocollagen expressed in non-animal cells and processed by a protease selected from the group consisting of neutrase, subtilisin, ficin, recombinant human trypsin and recombinant human pepsin.

According to some embodiments of the invention, the human telopeptide-comprising collagen comprises human procollagen.

According to some embodiments of the invention, the human telopeptide-comprising collagen comprises telocollagen.

According to some embodiments of the invention, the human procollagen comprises a C' terminal propeptide.

According to some embodiments of the invention, the procollagen comprises an N terminal propeptide.

According to some embodiments of the invention, the atelocollagen is a type I atelocollagen.

According to some embodiments of the invention, the atelocollagen comprises alpha atelocollagen.

According to some embodiments of the invention, the alpha atelocollagen comprises alpha 1 atelocollagen.

According to some embodiments of the invention, the alpha atelocollagen comprises alpha 2 atelocollagen.

According to some embodiments of the invention, the non-animal cell is a eukaryotic cell.

According to some embodiments of the invention, the eukaryotic cell is a yeast cell or a fungal cell.

According to some embodiments of the invention, the non-animal cell is a plant cell.

According to some embodiments of the invention, the plant cell is from a plant selected from the group consisting a tobacco, a maize, an alfalfa, a rice, a potato, a soybean, a tomato, a wheat, a barley, a canola, a carrot, a lettuce and a cotton.

According to some embodiments of the invention, the contacting is effected prior to purification of the telopeptide-comprising collagen.

According to some embodiments of the invention, the contacting is effected following purification of the telopeptide-comprising collagen.

According to some embodiments of the invention, the method further comprises purifying the atelocollagen following the generating to produce purified atelocollagen.

According to some embodiments of the invention, the method further comprises acid solubilizing the purified atelocollagen to generate soluble, purified atelocollagen.

According to some embodiments of the invention, at least 70% of the soluble, purified atelocollagen is capable of forming fibrils.

According to some embodiments of the invention, at least 88% of the soluble, purified atelocollagen is capable of forming fibrils.

According to some embodiments of the invention, the human atelocollagen is capable of generating fibrils.

According to some embodiments of the invention, the composition is an acidic composition.

According to some embodiments of the invention, the human telopeptide-comprising collagen is produced by targeting to a vacuole of the plant at least one type of a collagen chain and an exogenous P4H so as to allow hydroxylation of the at least one type of the collagen chain by the exogenous P4H.

According to some embodiments of the invention, the at least one type of the collagen chain comprises a signal peptide for targeting to the vacuole.

According to some embodiments of the invention, the exogenous P4H comprises a signal peptide for targeting to the vacuole.

According to some embodiments of the invention, the exogenous P4H comprises mammalian P4H.

According to some embodiments of the invention, the mammalian P4H comprises human P4H.

According to some embodiments of the invention, the exogenous P4H is capable of specifically hydroxylating the Y position of Gly-X-Y triplets of the at least one type of the collagen chain.

According to some embodiments of the invention, the telopeptide-comprising collagen is produced by expressing an exogenous polypeptide selected from the group consisting of LH, protease N and protease C.

According to some embodiments of the invention, the LH is LH3

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 2:
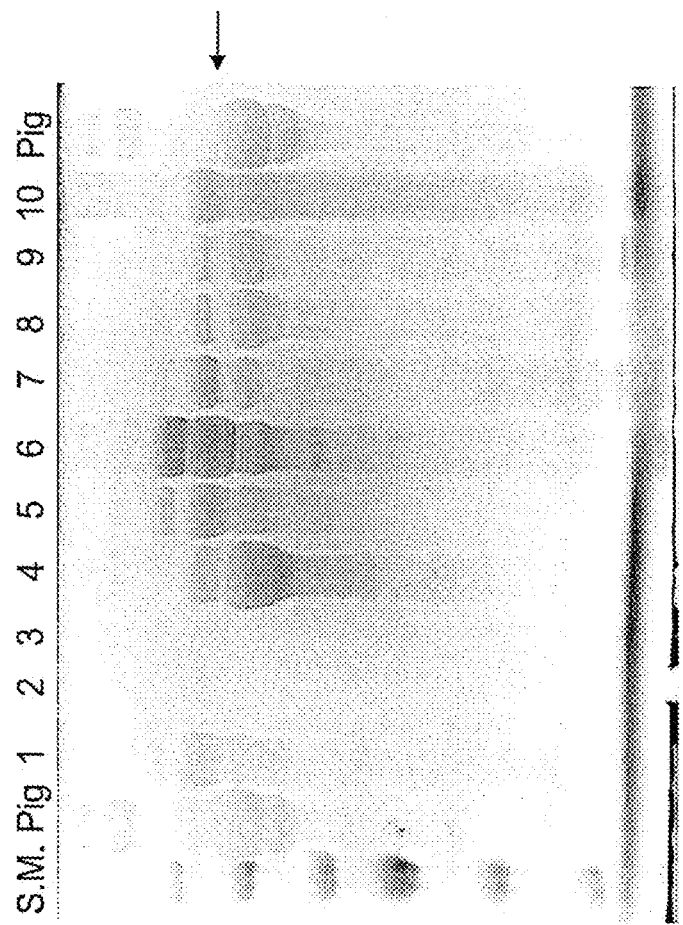
FIG. 2 Tobacco-leaf derived purified collagen following digestion with varying concentrations of trypsin. Collagen was extracted and purified as in FIG. 1 following digestion with 20 mg/L Trypsin (lanes 1-7) or 30 mg/L (lanes 8-10). Products were separated on a 10% SDS PAGE and analyzed with a Coomassie-based staining solution. Propeptide-free pig-derived collagen (0.5 mg/ml) was loaded and run as a positive control for collagen type 1 alpha 1 and alpha 2 chains.

sample as in lane 8 following resuspension in 0.5M acetic acid and centrifugation; lane 10: mature collagen following resuspension in 10 mM HCl and dialysis; lane 11: sample as in lane 10 with an additional filtration step; lane 12: sample as in lane 11 with an additional 5× concentration step; lane 13: sample as in lane 11 with an additional 20× concentration step; lane 14: sample as in lane 13 with additional 5× concentration step. Untreated procollagen samples (lanes 3-4) served as negative controls. Propeptide-free pig-derived collagen (2.5 µg) served as a positive control for alpha 1 and alpha 2 chains (lane 1).

Figure 12:
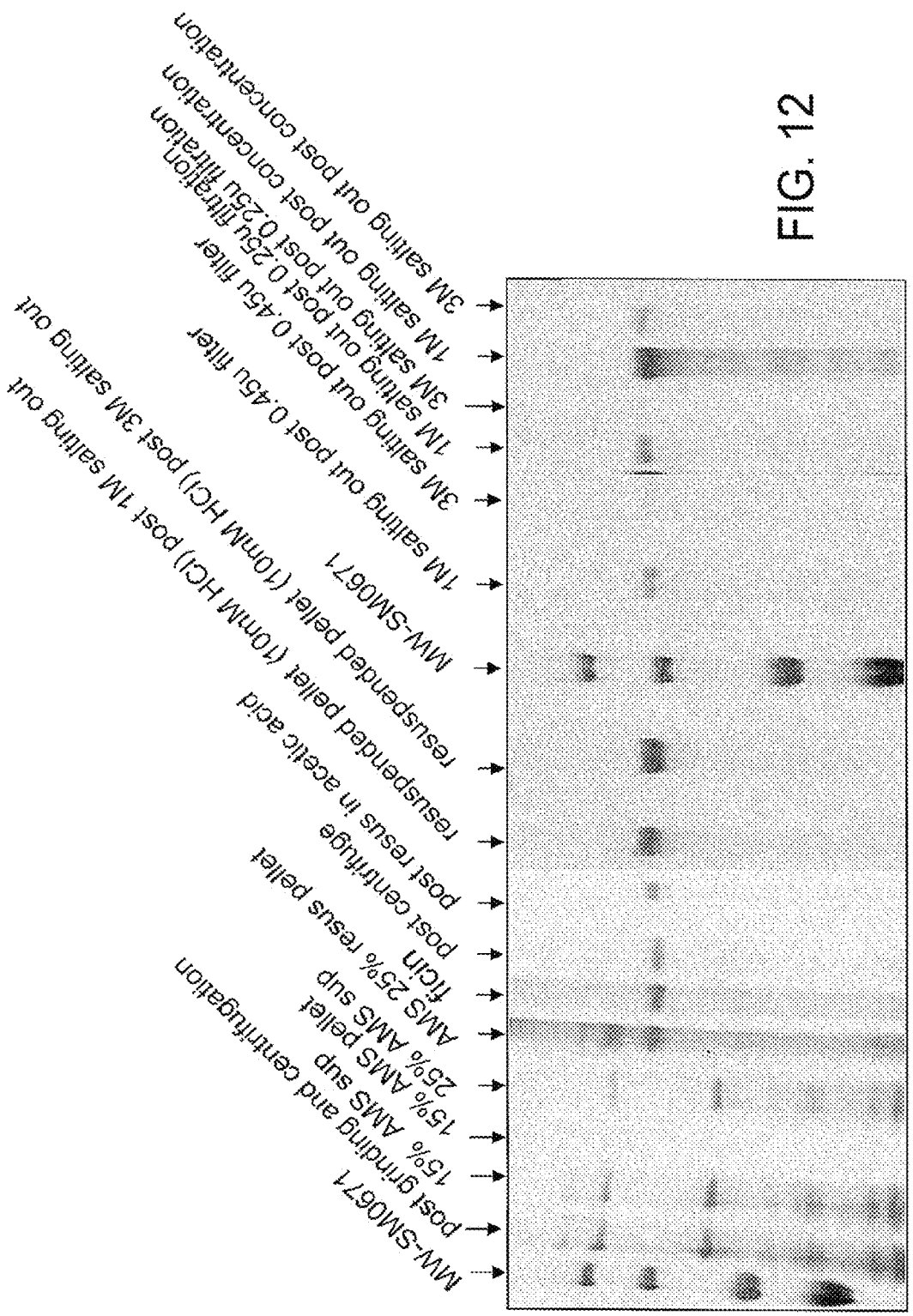

FIG. 12 Collagen content of post-ficin treated samples at the various stages of purification. Collagen-containing samples were collected at each extraction and purification stage of a reactor size AMS-based purification procedure described in the Material and Methods section. Samples were treated with ficin (5 mg/L, 15° C., 3 h) for propeptide removal, separated on a 10% SDS PAGE and stained with a Coomassie-based staining solution.

Figure 13:

FIG. 13 Optimization of procollagen cleavage by food-grade ficin: optimization of ficin concentration and reaction time. AMS-pelleted procollagen-expressing tobacco leaf extracts were resuspended in extraction buffer and then incubated with increasing concentrations of food-grade ficin (5-15 mg/L). Reaction mixtures were then incubated at 15° C. for 1-3 hours. Cleavage was terminated by centrifugation and protein samples were separated on 8% SDS-PAGE, transferred to nitrocellulose membranes and immunoblotted for α1 and α2 collagen chains with anti-collagen I. Procollagen bands are indicated by white arrows, while the red arrows indicate cleaved collagen bands.

Figure 14A:
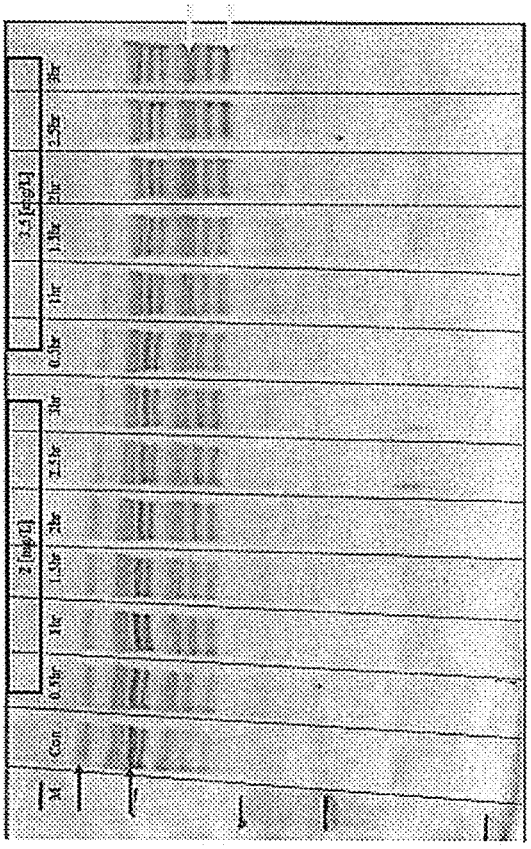
Figure 14B:
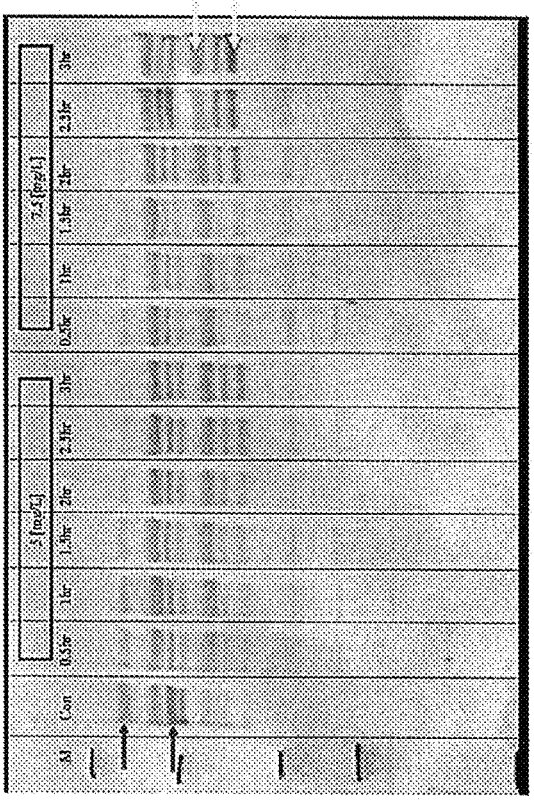
Figure 14C:
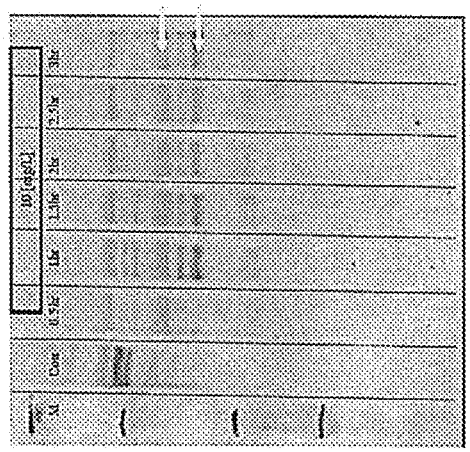

FIGS. 14A-C Optimization of procollagen cleavage by pharmaceutical-grade ficin: optimization of ficin concentration and reaction time. AMS-pelleted procollagen-expressing tobacco leaf extracts were resuspended in extraction buffer and then incubated with increasing concentrations of pharmaceutical-grade ficin (2.5-10 mg/L). Reaction mixtures were then incubated at 15° C. for 0.5-3 hours. Cleavage was terminated by centrifugation and protein samples were separated on 8% SDS-PAGE, transferred to nitrocellulose membranes and immunoblotted for α1 and α2 collagen chains with anti-collagen I. Green arrows indicate procollagen bands. Yellow arrows indicate collagen bands.

Figures 15A, 15B:
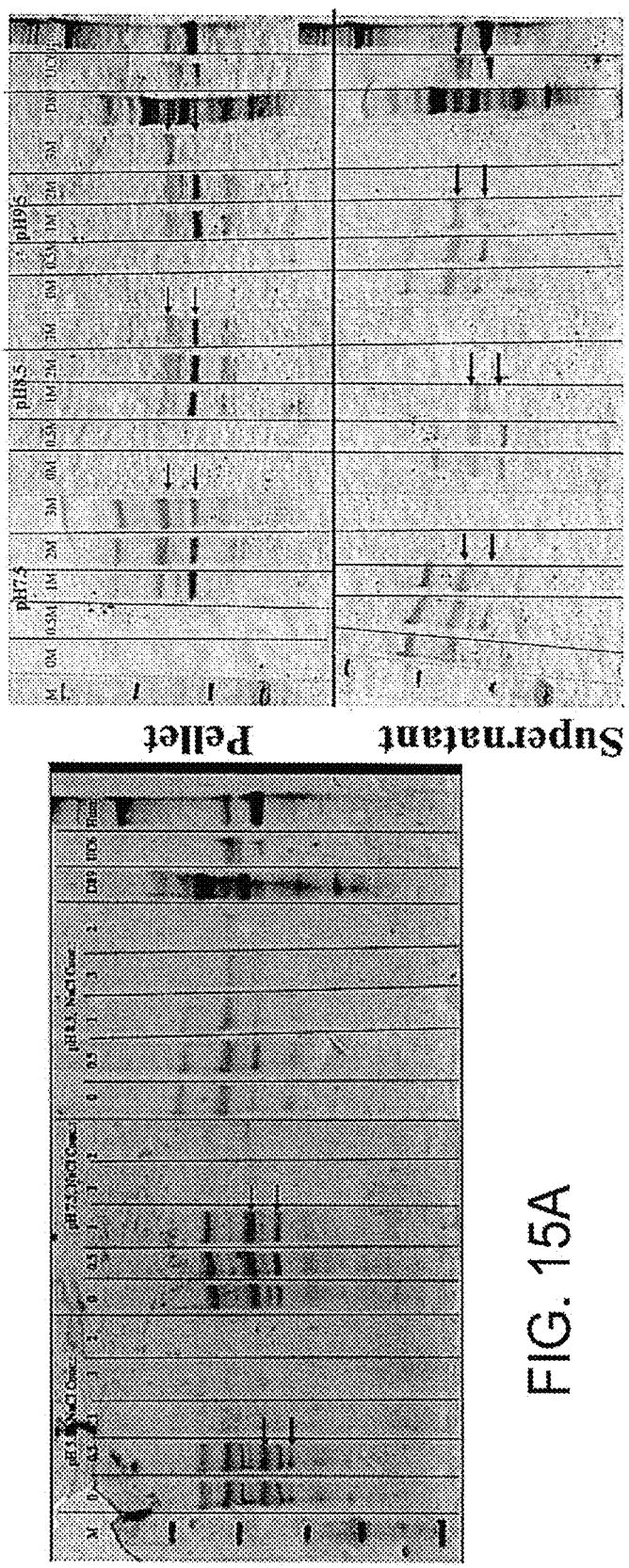

FIGS. 15A-B Optimization of procollagen cleavage by pharmaceutical-grade ficin: optimization of pH and salt concentrations in reaction buffer. AMS-pelleted procollagen-expressing tobacco leaf extracts were resuspended in extraction buffer containing 10 mg/L pharmaceutical-grade ficin at varying pH values (5.5-9.5) and with increasing NaCl concentrations (0.5-3 M). Reaction mixtures were then incubated at 15° C. for 1 hour. Cleavage was terminated by centrifugation and protein samples of both resulting pellets and supernatants were separated on 8% SDS-PAGE, transferred to nitrocellulose membranes and immunoblotted for α1 and α2 collagen chains with anti-collagen I. Arrows indicate collagen bands.

Figure 16:
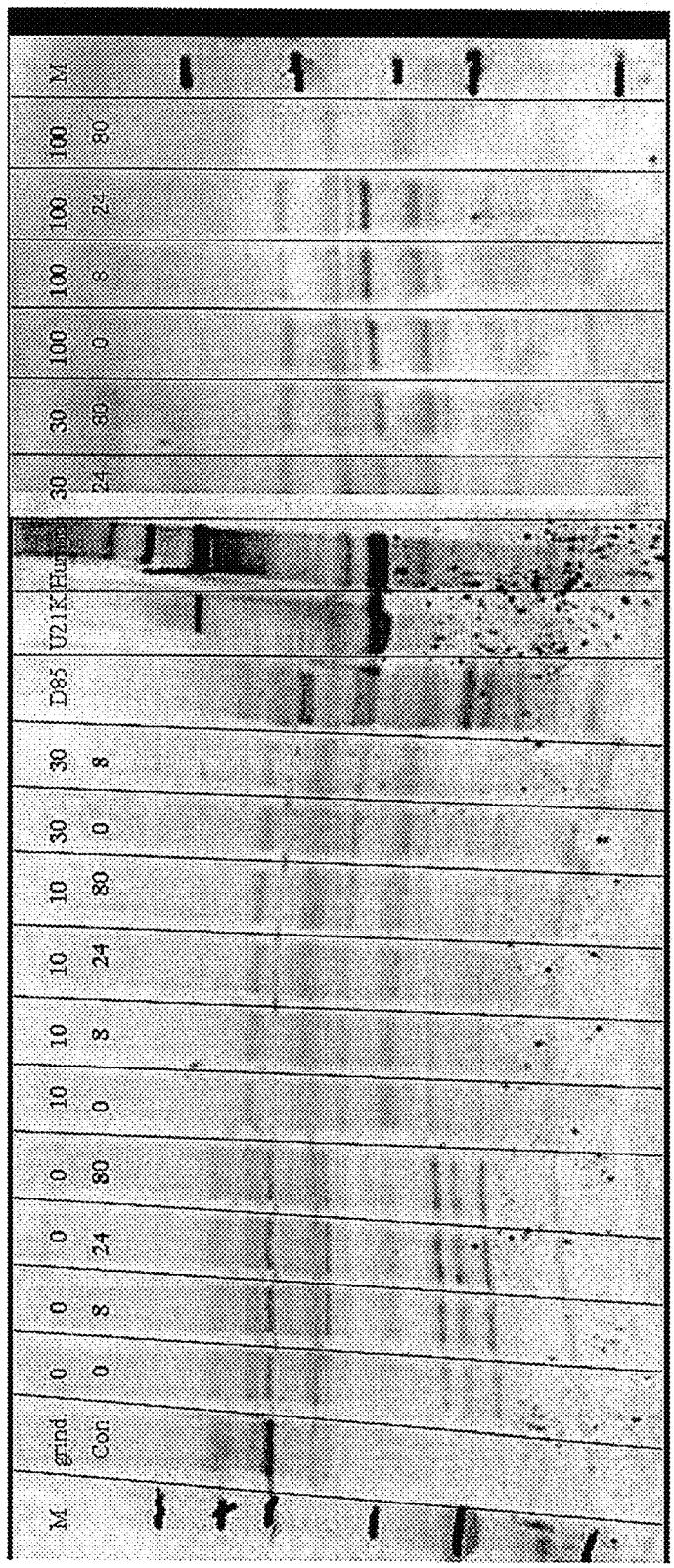

FIG. 16 Optimization of procollagen cleavage by pharmaceutical-grade ficin: optimization of EDTA and L-cystein concentrations in reaction buffer. AMS-pelleted procollagen-expressing tobacco leaf extracts were resuspended in extraction buffer (pH 7.5) containing varying concentrations of L-cystein (10-100 mM—upper panel of concentrations) and of EDTA (8-80 mM—lower panel of concentrations). Samples were then incubated with 1 mg/L pharmaceutical-grade ficin at 15° C. for 1 hr. Cleavage was terminated by centrifugation and protein samples were separated on 8% SDS-PAGE, transferred to nitrocellulose membranes and immunoblotted for α1 and α2 collagen chains with anti-collagen I.

Figure 17:
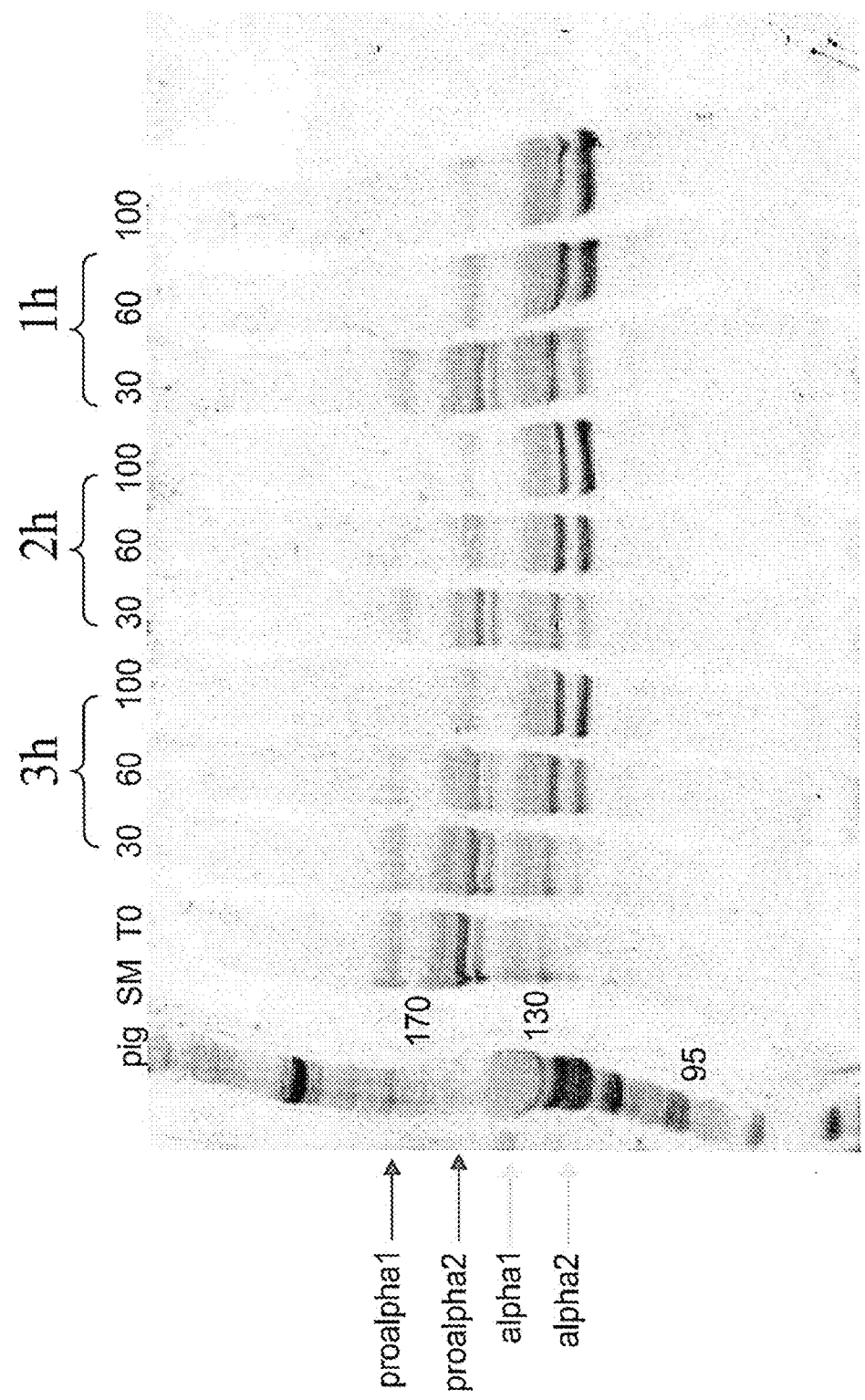

FIG. 17 Effective procollagen digestion by recombinant trypsin at pH 7.5. AMS-pelleted procollagen-expressing tobacco leaf extracts were resuspended in extraction buffer (pH 7.5) containing L-cystein and EDTA. Samples were then incubated with 30-100 mg/L recombinant trypsin at 15° C. for 1-3 hrs. Cleavage was terminated by centrifugation and protein samples were separated on 8% SDS-PAGE, transferred to nitrocellulose membranes and immunoblotted for α1 and α2 collagen chains with anti-collagen I.

DESCRIPTION OF THE PREFERRED EMBODIMENTS

The present invention is of a method of processing procollagen in order to generate homogeneous, soluble, fibril-forming atelocollagen.

The principles and operation of the method according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Whilst reducing the present invention to practice, the present inventors have shown, by analysis of proteolysis results by SDS PAGE, that certain plant-derived proteases, (e.g. papain), are not capable of cleaving the propeptide portion from soluble procollagen without proteolytic cleavage within the helical region (even though they are capable of removing telopeptides from telocollagen originating from animal sources), while other proteases (e.g. esperase, savinase) do not effectively cleave the propeptide region from soluble procollagen, thereby hindering effective fibrillogenesis. Through meticulous experimentation, the present inventors uncovered that only particular plant-derived proteases such as ficin, and bacterial-derived proteases such as neutrase and subtilisin may be used to correctly cleave the propeptide portion (including the telopeptides) from soluble procollagen to generate a homogeneous preparation of soluble atelocollagen (FIGS. 4, 6, 8, 10 and 11) without digesting the helical region of the non-animal procollagen. In addition, the present inventors showed that a recombinant trypsin is also capable of correct cleavage (FIG. 17). The present inventors further showed that cleavage with ficin allows the resultant atelocollagen to retain its fibrillogenic capacity (Table 3 of the Examples section herein below).

Thus, according to one aspect, there is provided a method of generating atelocollagen. The method comprises contacting a human recombinant telopeptide-comprising collagen with a protease selected from the group consisting of neutrase, subtilisin, recombinant trypsin, recombinant pepsin and ficin, wherein the human recombinant telopeptide-comprising collagen is expressed in a non-animal cell, thereby generating the atelocollagen.

As used herein, the phrase "telopeptide-comprising collagen" refers to a soluble collagen molecule which comprises telopeptides that are longer than the telopeptide remnants comprised in atelocollagen. Thus, the telopeptide-comprising collagen may be procollagen which comprises full length propeptides. Alternatively, the telopeptide-comprising collagen may be a procollagen molecule which comprises partially digested propeptides. Still alternatively, the telopeptide-comprising collagen may be telocollagen.

The term "procollagen" as used herein, refers to a collagen molecule (e.g. human) that comprises either an N-terminal propeptide, a C-terminal propeptide or both. Exemplary human procollagen amino acid sequences are set forth by SEQ ID NOs: 1, 2, 7 and 8.

The term "telocollagen" as used herein, refers to collagen molecules that lack both the N- and C-terminal propeptides typically comprised in procollagen but still contain the telopeptides. As mentioned in the Background section herein above, the telopeptides of fibrillar collagen are the remnants of the N- and C-terminal propeptides following digestion with native N/C proteinases.

Recombinant human telocollagen may be generated in cells which have been transformed to express both exogenous human procollagen and the respective protease (i.e. C or N or both). Polynucleotide sequences encoding such proteases are exemplified by SEQ ID Nos: 10 (protease C) and 11 (Protease N). Such proteases can be expressed such that they are accumulated in the same subcellular compartment as the collagen chain, as further described herein below.

As used herein, the term "atelocollagen" refers to collagen molecules lacking both the N- and C-terminal propeptides typically comprised in procollagen and at least a portion of its telopeptides, but including a sufficient portion of its telopeptides such that under suitable conditions it is capable of forming fibrils.

Any type of atelocollagen may be generated according to the method of the present invention. Examples include fibril-forming collagens (types I, II, III, V, and XI), network-forming collagens (types IV, VIII, and X), collagens associated with fibril surfaces (types IX, XII, and XIV), collagens which occur as transmembrane proteins (types XIII and XVII), or form 11-nm periodic beaded filaments (type VI). For further description please see Hulmes, 2002, J Struct Biol. January-February; 137(1-2):2-10. According to one embodiment, the atelocollagen comprises an alpha 1 and/or 2 chain of type I collagen.

It will be appreciated that the present invention also contemplates genetically modified forms of collagen/atelocollagen—for example collagenase-resistant collagens and the like [Wu et al., Proc Natl. Acad Sci, Vol. 87, p. 5888-5892, 1990].

The recombinant human procollagen or telocollagen may be expressed in any non-animal cell, including but not limited to plant cells and other eukaryotic cells such as yeast and fungus.

Plants in which the human procollagen or telocollagen may be produced (i.e. expressed) may be of lower (e.g. moss and algae) or higher (vascular) plant species, including tissues or isolated cells and extracts thereof (e.g. cell suspensions). Preferred plants are those which are capable of accumulating large amounts of collagen chains, collagen and/or the processing enzymes described herein below. Such plants may also be selected according to their resistance to stress conditions and the ease at which expressed components or assembled collagen can be extracted. Examples of plants in which human procollagen may be expressed include, but are not limited to tobacco, maize, alfalfa, rice, potato, soybean, tomato, wheat, barley, canola, carrot, lettuce and cotton.

Production of recombinant human procollagen is typically effected by stable or transient transformation with an exogenous polynucleotide sequence encoding human procollagen.

Exemplary polynucleotide sequences encoding human procollagen are set forth by SEQ ID NOs: 3, 4, 12 and 13.

As mentioned, production of human telocollagen is typically effected by stable or transient transformation with an exogenous polynucleotide sequence encoding human procollagen and at least one exogenous polynucleotide sequence encoding the relevant protease.

The stability of the triple-helical structure of collagen requires the hydroxylation of prolines by the enzyme prolyl-4-hydroxylase (P4H) to form residues of hydroxyproline within the collagen chain. Although plants are capable of synthesizing hydroxyproline-containing proteins, the prolyl hydroxylase that is responsible for synthesis of hydroxyproline in plant cells exhibits relatively loose substrate sequence specificity as compared with mammalian P4H. Thus, production of collagen containing hydroxyproline only in the Y position of Gly-X-Y triplets requires co-expression of collagen and human or mammalian P4H genes [Olsen et al, Adv Drug Deliv Rev. 2003 Nov. 28; 55(12):1547-67].

Thus, according to one embodiment, the procollagen or telocollagen is expressed in a subcellular compartment of a plant that is devoid of endogenous P4H activity so as to avoid incorrect hydroxylation thereof. As is used herein, the phrase "subcellular compartment devoid of endogenous P4H activity" refers to any compartmentalized region of the cell which does not include plant P4H or an enzyme having plant-like P4H activity. According to one embodiment, the subcellular compartment is a vacuole.

Accumulation of the expressed procollagen in a subcellular compartment devoid of endogenous P4H activity can be effected via any one of several approaches.

For example, the expressed procollagen/telocollagen can include a signal sequence for targeting the expressed protein to a subcellular compartment such as the apoplast or an organelle (e.g. chloroplast). Examples of suitable signal sequences include the chloroplast transit peptide (included in Swiss-Prot entry P07689, amino acids 1-57) and the Mitochondrion transit peptide (included in Swiss-Prot entry P46643, amino acids 1-28).

Alternatively, the sequence of the procollagen can be modified in a way which alters the cellular localization of the procollagen when expressed in plants.

The present invention therefore contemplates genetically modified cells co-expressing both human procollagen and a P4H, capable of correctly hydroxylating the procollagen alpha chain(s) [i.e. hydroxylating only the proline (Y) position of the Gly-X-Y triplets]. P4H is an enzyme composed of two subunits, alpha and beta as set forth in Genbank Nos. P07237 and P13674. Both subunits are necessary to form an active enzyme, while the beta subunit also possesses a chaperon function.

The P4H expressed by the genetically modified cells of the present invention is preferably a human P4H which is encoded by, for example, SEQ ID Nos: 5 and 6. In addition, P4H mutants which exhibit enhanced substrate specificity, or P4H homologues can also be used. A suitable P4H homologue is exemplified by an Arabidopsis oxidoreductase identified by NCBI accession no: NP_179363.

Since it is essential that P4H co-accumulates with the expressed procollagen chain, the coding sequence thereof is preferably modified accordingly (e.g. by addition or deletion of signal sequences).

In mammalian cells, collagen is also modified by Lysyl hydroxylase, galactosyltransferase and glucosyltransferase. These enzymes sequentially modify lysyl residues in specific positions to hydroxylysyl, galactosylhydroxylysyl and glucosylgalactosyl hydroxylysyl residues at specific positions. A single human enzyme, Lysyl hydroxylase 3 (LH3), as set forth in Genbank No. O60568, can catalyze all three consecutive modifying steps as seen in hydroxylysine-linked carbohydrate formation.

Thus, the genetically modified cells of the present invention may also express mammalian LH3. An LH3 encoding sequence such as that set forth by SEQ ID No: 9 can be used for such purposes.

The procollagen (s) and modifying enzymes described above can be expressed from a stably integrated or a transiently expressed nucleic acid construct which includes polynucleotide sequences encoding the procollagen alpha chains and/or modifying enzymes (e.g. P4H and LH3) positioned under the transcriptional control of functional promoters. Such a nucleic acid construct (which is also termed herein as an expression construct) can be configured for expression throughout the whole organism (e.g. plant, defined tissues or defined cells), and/or at defined developmental stages of the organism. Such a construct may also include selection markers (e.g. antibiotic resistance), enhancer elements and an origin of replication for bacterial replication.

It will be appreciated that constructs including two expressible inserts (e.g. two alpha procollagen chain types, or a procollagen alpha chain and P4H) preferably include an individual promoter for each insert, or alternatively such constructs can express a single transcript chimera including both insert sequences under a single promoter. In such a case, the chimeric transcript may include an intrariribosomal entry region (IRES) sequence between the two insert sequences such that the downstream insert can be translated therefrom.

Numerous functional expression promoters and enhancers which can be either tissue specific, developmentally specific, constitutive or inducible can be utilized by the constructs of the present invention, some examples are provided herein under.

As used herein, the phrase "plant promoter" or "promoter" includes a promoter which can direct gene expression in cells (including DNA-containing organelles) of plants, fungus and yeast. Such a promoter can be derived from a plant, bacterial, viral, fungal or animal origin. Such a promoter can be constitutive, i.e., capable of directing high levels of gene expression in a plurality of tissues, tissue specific, i.e., capable of directing gene expression in a particular tissue or tissues, inducible, i.e., capable of directing gene expression under a stimulus, or chimeric, i.e., formed of portions of at least two different promoters.

Thus, the plant promoter employed can be a constitutive promoter, a tissue-specific promoter, an inducible promoter or a chimeric promoter.

Examples of constitutive promoters include, without being limited to, CaMV35S and CaMV19S promoters, FMV34S promoter, sugarcane bacilliform badnavirus promoter, CsVMV promoter, Arabidopsis ACT2/ACT8 actin promoter, Arabidopsis ubiquitin UBQ1 promoter, barley leaf thionin BTH6 promoter, and rice actin promoter.

Examples of tissue-specific promoters include, without being limited to, bean phaseolin storage protein promoter, DLEC promoter, PHS promoter, zein storage protein promoter, conglutin gamma promoter from soybean, AT2S1 gene promoter, ACT11 actin promoter from Arabidopsis, napA promoter from Brassica napus and potato patatin gene promoter.

The inducible promoter is a promoter induced by a specific stimulus such as stress conditions comprising, for example, light, temperature, chemicals, drought, high salinity, osmotic shock, oxidative conditions or pathogenic stress and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

The promoter utilized by the present invention is preferably a strong, constitutive promoter such that overexpression of the construct inserts is effected following transformation.

It will be appreciated that any of the construct types used in the present invention can be co-transformed into the same cells using identical or different selection markers in each construct type. Alternatively, the first construct type can be introduced into a first organism, e.g. plant, while the second construct type can be introduced into a second isogenic plant, followed by crossing of the transgenic plants resultant therefrom and selection of the progeny for double transformants. Further self-crosses of such progeny can be employed to generate lines homozygous for both constructs.

A number of vectors containing constitutive or inducible promoters can be used for transforming yeast cells. For a review, see Current Protocols in Molecular Biology, Vol. 2, 1988, ed. Ausubel et al., Greene Publish. Assoc. & Wiley Interscience, ch. 13; Grant et al., 1987, "Expression and Secretion Vectors for Yeast," in Methods in Enzymol. 153: 516-544; Glover, 1986, DNA Cloning, Vol. II, IRL Press, Wash., D.C., Ch. 3; and Bitter, 1987, "Heterologous Gene Expression in Yeast," in Methods in Enzymol. 152:673-684. A constitutive yeast promoter such as ADH or Leu2 or an inducible promoter such as GAL can be used ("Cloning in Yeast," ch. 3, R. Rothstein In: DNA Cloning, Vol. 11, A Practical Approach, Ed. D. M. Glover, 1986, IRL Press, Wash. D.C.). Alternatively, vectors can be used which promote integration of foreign DNA sequences into the yeast chromosome.

There are various methods for introducing nucleic acid constructs into both monocotyledonous and dicotyledenous plants (Potrykus, I., Annu Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct, in which case these sequences are not inherited by the plant's progeny.

In addition, several methods exist in which a nucleic acid construct can be directly introduced into the DNA of a DNA-containing organelle such as a chloroplast.

There are two principle methods of effecting stable genomic integration of exogenous sequences, such as those included within the nucleic acid constructs of the present invention, into plant genomes:

(i) Agrobacterium-mediated gene transfer: Klee et al. (1987) Annu Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

The Agrobacterium system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure which can be performed with any tissue explant that provides a good source for initiation of whole plant differentiation. See Horsch et al. in Plant Molecular Biology Manual A5, Kluwer Academic Publishers, Dordrecht (1988) p. 1-9. A supplementary approach employs the Agrobacterium delivery system in combination with vacuum infiltration. The Agrobacterium system is especially viable in the creation of transgenic dicotyledenous plants.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Following transformation plant propagation is exercised. The most common method of plant propagation is by seed. However, regeneration by seed propagation presents the drawback of decreased uniformity due to heterozygosity, as seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Thus, micropropagation which provides a rapid, consistent reproduction of the transformed plants is the preferred mode of plant regeneration when uniformity is essential.

Transient expression methods which can be utilized for transiently expressing the isolated nucleic acid included within the nucleic acid construct of the present invention include, but are not limited to, microinjection and bombardment as described above but under conditions which favor transient expression. Alternatively, virally mediated expression can be employed wherein, a packaged or unpackaged recombinant virus vector including the nucleic acid construct is utilized to infect plant tissues or cells such that a propagating recombinant virus established therein expresses the non-viral nucleic acid sequence.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsulate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsulate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

A technique for introducing exogenous nucleic acid sequences to the genome of the chloroplasts is known. This technique involves the procedures as described below. First, the exogenous nucleic acid is introduced via particle bombardment into the cells with the aim of introducing at least one exogenous nucleic acid molecule into the chloroplasts. The exogenous nucleic acid is selected by its capacity to become integrated into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves, by sequential selection procedures, to ascertain that all or the vast majority of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Regardless of the transformation technique employed, once procollagen-expressing progeny are identified, such plants are further cultivated under conditions which maximize expression thereof. Progeny resulting from transformed plants can be selected, by verifying presence of exogenous mRNA and/or polypeptides by using nucleic acid or protein probes (e.g. antibodies). The latter approach enables localization of the expressed polypeptide components (by for example, probing fractionated plants extracts) and thus also verifies the plant's potential for correct processing and assembly of the foreign protein.

Following cultivation of such plants, the telopeptide-comprising collagen is typically harvested. Plant tissues/cells are preferably harvested at maturity, and the procollagen molecules are isolated using extraction approaches. Preferably, the harvesting is effected such that the procollagen remains in a state that it can be cleaved by protease enzymes. According to one embodiment, a crude extract is generated from the transgenic plants of the present invention and subsequently contacted with the protease enzymes. An exemplary method for generating a plant crude extract is described in the Examples section herein under.

It will be appreciated that the propeptide or telopeptide-comprising collagen may be purified from the genetically engineered cells of the present invention prior to incubation with protease, or alternatively may be purified following incubation with the protease. Still alternatively, the propeptide or telopeptide-comprising collagen may be partially purified prior to protease treatment and then fully purified following protease treatment. Yet alternatively, the propeptide or telopeptide-comprising collagen may be treated with protease concomitant with other extraction/purification procedures.

Exemplary methods of purifying or semi-purifying the telopeptide-comprising collagen of the present invention include, but are not limited to salting out with ammonium sulfate or the like and/or removal of small molecules by ultrafiltration.

As described in the Background herein above, there is a risk involved in using animal source material for medical purposes. This risk is also relevant when selecting the proteolytic enzymes used in processing the procollagen expressed in plants to atelocollagen. Application of bovine source enzymes such as trypsin or pepsin, may in itself contaminate the final preparation with disease carriers. It is therefore desired to devise a production system where all components are free of animal source.

The present inventors have shown that only particular proteases are capable of correctly cleaving recombinant propeptide or telopeptide-comprising collagen. These include certain plant derived proteases e.g. ficin (EC 3.4.22.3) and certain bacterial derived proteases e.g. subtilisin (EC 3.4.21.62), neutrase. The present inventors also contemplate the use of recombinant enzymes such as rhTrypsin and rhPepsin Such enzymes are commercially available e.g. Ficin from Fig tree latex (Sigma, catalog #F4125 and Europe Biochem), Subtilisin from *Bacillus licheniformis* (Sigma, catalog #P5459) Neutrase from bacterium *Bacillus amyloliquefaciens* (Novozymes, catalog #PW201041) and TrypZean™, a recombinant human trypsin expressed in corn (Sigma catalog #T3449).

The procollagen or telocollagen is preferably contacted with the proteases under conditions such that the proteases are able to cleave the propeptides or telopeptides therefrom. Typically, the conditions are determined according to the particular protease selected. Thus, for example procollagen may be incubated with a protease for up to 15 hours, at a concentration of 1-25 mg/ml and a temperature of about 10-20° C.

Following protease digestion, the generated atelocollagen may be further purified e.g. by salt precipitation, as described in the Examples section below so that the end product comprises a purified composition of atelocollagen having been processed from plant or plant-cell generated procollagen by a protease selected from the group consisting of neutrase, subtilisin, ficin and recombinant human trypsin and analyzed using methods known in the art (e.g. size analysis via Coomassie staining, Western analysis, etc.).

Following purification, the atelocollagen may be resolubilized by addition of acidic solutions (e.g. 10 mM HCl). Such acidic solutions are useful for storage of the purified atelocollagen.

The present inventors have shown that following digestion with ficin, the atelocollagen maintains its ability to form fibrils upon neutralization of the above described acid solutions. According to one embodiment, at least 70% of the purified and resolubilized atelocollagen generated according to the method of the present invention is capable of forming fibrils. According to one embodiment, at least 88% of the purified and resolubilized atelocollagen generated according to the method of the present invention is capable of forming fibrils.

The ability to form fibrils demonstrates that the generated atelocollagen is useful for medical purposes including, but not limited to cosmetic surgery, healing aid for burn patients, reconstruction of bone and a wide variety of dental, orthopedic and surgical purposes.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly described in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Collagen extraction and enzymatic reaction: In a blender, 300 g of tobacco leaves were blended in a chilled extraction buffer (600 ml of 100 mM Tris-HCl pH 7.5 containing 360 mg potassium-meta-bisulfite, 530 mg L-Cysteine and 1 g EDTA) supplemented with 5 g PVPP and 2 g of activated carbon. Blending was performed 5 times for 1 minute intervals to keep temperatures below 15° C. Crude extract was filtered through a gauze pad and centrifuged for 30 min, 25000 g, 5° C. The supernatant was collected; $CaCl_2$ was added to a final concentration of 10 mM. The supernatant was divided into 10 ml samples. The desired enzyme was added to each 10 ml sample, according to the conditions set forth in Table 1 herein below.

TABLE 1

Procollagen digestion reaction conditions

| # Sample | Protease: | Concentration of protease (mg/Liter): | Incubation time (Hours): | Incubation temperature (degrees Celcius): |
| --- | --- | --- | --- | --- |
| 1 | Desired enzyme | 1 | 3 | 15 |
| 2 | Desired enzyme | 5 | 3 | 15 |
| 3 | Desired enzyme | 25 | 3 | 15 |
| 4 | Desired enzyme | 1 | 6 | 15 |
| 5 | Desired enzyme | 5 | 6 | 15 |
| 6 | Desired enzyme | 25 | 6 | 15 |
| * | Control-no protease | 0 | 3 | 15 |
| * | Control-no protease | 0 | 6 | 15 |

Enzyme description: Ficin from Fig tree latex (Sigma, catalog #F4125), Subtilisin from *Bacillus licheniformis* (Sigma, catalog #P5459-5gr), Bromelain from pineapple stem (Sigma, catalog #B4882-10gr), Papain from Carica papaya (Fluka, Catalog #76220-25gr), Savinase 6.0 t type W from the alkalophilic bacterium *Bacillus lentus* (Novozymes, catalog #PX92500501), Neutrase 1.5 MG from bacterium *Bacillus amyloliquefaciens* (Novozymes, catalog #PW201041), Protamex, a commercial Bacillus proteinase complex (Novozymes, catalog #PW2A1021), Alcalase 3.0 T, *Bacillus subtilis* alkaline proteinase (Novozymes, catalog #PJ90000901), Esperase 6.0 T, alkalophilic bacterium *Bacillus lentus* (Novozymes, catalog #PE90110401), Alcalase 2.4 L FG, *Bacillus subtilis* alkaline proteinase (Novozymes, catalog #PLN05330), Esperase 8.0 L, alkalophilic bacterium *Bacillus lentus* (Novozymes, catalog #PE00077) were all donated by Novozymes. Trypsin, pancreatic trypsin 6.0 S type saltfree, from animal pancreas (Novozymes, catalog #P245-D20). TrypZean™, a recombinant trypsin expressed in corn was purchased from Sigma Chemical Co. (catalog #: T3449).

Determination of atelocollagen concentration: The concentration of atelocollagen generated according to Examples 3-4 was assayed by two methods as follows:

Sircol™ assay: Sircol™ collagen assay kit was purchased from Biocolor Ltd. (Cat. No 85000). This assay is based on the interaction of the Sirius Red dye with the collagen triple helix. The analysis was performed according to the supplier's instruction manual, $4^{th}$ edition, 2002. Bovine collagen standard was used to prepare a calibration curve (0 to 50 μg collagen). Three samples of 10-50 μl of the collagen solution in 10 mM HCl were placed into a 1.5 ml Eppendorf tube, and the volume was brought to 100 μl with 0.5 M acetic acid. 1 ml Sircol™ dye reagent was added to each tube and the tubes were shaken for 30 min at room temperature. Tubes were centrifuged at 12,000 rpm for 10 min at room temperature, the supernatant was aspirated and the tubes were inverted over an absorbing paper to remove the remaining supernatant. Cotton buds were used to remove any access drops from the walls of the tubes. 1 ml of Alkali reagent was added to each tube, mixed well and incubated for 10 min at room temperature. Absorption at 540 nm was measured using a spectrophotometer and the concentration of collagen was calculated against the calibration curve, using 10 mM HCl as a blank sample.

SDS-PAGE Instant Blue assay: Samples were boiled for 5 min in SAB buffer (reducing conditions) and centrifuged at 12,000 rpm for 5 min, prior to loading on a SDS PAGE, 8% acrylamide. The gel was run in a Mini Protean 3 unit (BioRad #165-3301, 165-3302). Instant Blue reagent (Novexin #ISB01L) was applied to the gel until the protein was visualized as blue bands on the gel. The gel was rinsed with water and dried. Concentration of the collagen bands was calculated by densitometry, against a human standard loaded on the same gel.

Coomassie analysis: Samples of collagen (in 10 mM HCl) were titered to pH 7.5 using 1M Tris. Sample Application Buffer containing 10% beta-mercaptoethanol and 8% SDS was added by diluting it fourfold in the 30 μl of pH titered samples. The samples were boiled for 7 minutes. 30 μl of the supernatant were loaded on to a 10% polyacrylamide gel and separated for 2 hours at 100 volt. The gel was transfer to a coomassie-based solution for 1 hour with shaking. The Coomassie dye was removed using a standard destain solution.

SDS-PAGE and Western blot analysis of α1 and α2 collagen chains: Samples were boiled for 7 minutes in reducing sample application buffer (2.5% β-mercaptoethanol and 2% SDS) and then centrifuged for 15 minutes at 13,000 rpm. 30 μl of the supernatant were separated on a 10% polyacrylamide gel. Following separation, standard Western blot protocols were employed to blot samples onto nitrocellulose membranes. Following transfer, the membranes were incubated with anti-Collagen I antibody (Chemicon Inc. catalogue #AB745) for immunodetection of α1 and α2 collagen chains. Molecular weight markers were purchased from Fermentas Inc. (catalogue #SM0671).

Controls: A positive control of Human Skin Collagen Type I purchased from Calbiochem (#234138) was employed as a marker for Western blot analyses. The grinding control sample reflects pellets derived from tobacco leaves immediately prior to resuspension in extraction buffer. The "D" control samples reflect the same pellets following resuspension in extraction buffer. "K" control samples include ficin-digested procollagen in 10 mM HCl. To monitor background ficin-independent protease activity, ficin-free cleavage samples were always prepared in parallel to all ficin digestion tests.

Purification of collagen from transgenic plants: Digestion of propeptides in the collagen-containing extract was initiated by the addition of 30 mg/L trypsin or 5 mg/L (50 μl/L) Subtilisin (Sigma #P5459) or 5 mg/L Ficin (Sigma #F4125). Proteolysis was performed at 15° C. for 4 hours. Elimination of non-soluble contaminants was performed by centrifugation for 30 min, 22,000 g, 15° C. The supernatant was recovered and the collagen was precipitated by slowly adding crystalline NaCl to a final concentration of 3.13 M with constant stirring for 20 min at R.T. The solution was incubated in a cold room O.N. without stirring. Collection of the collagen was effected by centrifugation at 25,000 g, for 2 hours at 5° C.

The supernatant was carefully poured through four layers of gauze pad. The pellets were resuspended in 200 ml of 250 mM acetic acid and 2M NaCl for 5 minutes using a magnetic stirrer. The suspension was centrifuged at 25,000 g, for 40 min at 5° C. Traces of supernatant were eliminated from the glass vials. The pellets were redissolved in 200 ml of 0.5 M acetic acid at room temperature for 1 hour. Elimination of nonsoluble matter was performed by centrifugation at 16,000 g, 30 min, 15° C. The supernatant was poured through 12 layers of gauze pad. Collagen was precipitated by slowly adding NaCl to a final concentration of 3M with constant stirring for 20 min at R.T. The solution was incubated at 4° C. for 8 hours up to O.N. Collection of collagen was performed by centrifugation at 25,000 g, for 2 hours at 5° C. Following aspiration of the supernatant, the pellet was redissolved in 200 ml of 0.5 M acetic acid using a magnetic stirrer at R.T. for 1 hour. Elimination of nonsoluble matter was performed by centrifugation at 16,000 g, 30 min, 15° C. The supernatant was poured through 12 layers of gauze pad. Collagen was precipitated by slowly adding NaCl to a final concentration of 3M with constant stirring for 20 min at R.T. The solution was incubated at 4° C. for 8 hours. Collagen was collected by centrifugation at 2,000 g, for 2 hours at 5° C. Supernatent was aspirated. The pellet was redissolved in 40 ml of 10 mM HCl by pipetation and vortexing for 5 min at R.T. The solution was transferred to a dialysis bag (MWCO 14,000 Da) and dialyzed for 4 hours against 4 L of 10 mM HCl at 4° C. This dialysis was repeated O.N.

Sterilization of the collagen was performed by filtering the solution first through a 0.45 µm filter, then through a 0.2 µM filter using a 30 ml syringe. Collagen was further concentrated via ultrafiltration using a Vivaspin PES 20 ml filtration tube (Vivascience, #VS2041, MWCO 100'000). Centrifugation was performed for 45 min at 5000 g at 5° C. until the volume was reduced to 0.75 ml.

Optimization of digestion kinetics and conditions of procollagen cleavage by food-grade ficin: Pellets (collected as described in Example 4), up to saturation in 25% ammonium sulfate (AMS)) were resuspended in a buffer (Buffer A: 4.5 mM potassium metadisulfite, 12.5 mM L-cystein, 7.5 mM EDTA dissolved in 0.1 M sodium phosphate buffer, titrated to pH 7.5 with 10 M NaOH or 6 N HCl) at a ratio of 4.36 g pellet:200 mL ice cold buffer. Samples were then stirred for 20 min at 15° C. Aliquots of 10 mL per 15 mL test tube were then prepared, followed by administration of increasing concentrations (5-15 mg/L) of ficin (Fig tree latex, Biochem Europe food grade ficin). Samples were incubated at 15° C. for 1-3 hours and separated by SDS-PAGE and then analyzed by Western blot for presence of collagen migrating at lower molecular weights than procollagen.

Tobacco leaf-derived pellets resuspended in phosphate Buffer A (27.2 g:800 mL buffer) of varying pH values (5.5, 7.5 or 8.5) were treated with 10 mg/L ficin in the presence of 0-3 M NaCl for 1 h at 15° C. The reaction was terminated by centrifuging 1 mL samples from each reaction mixture (10 min, 15000 g, 4° C.). Pellets were resuspended in 1 mL Buffer A (pH 7.5), separated by SDS-PAGE and analyzed by means of Western blot.

Optimization of digestion kinetics and conditions of procollagen cleavage by pharmaceutical-grade ficin: Tobacco leaf pellets were resuspended in a pharmaceutical-grade (Biochem-Europe Pharm grade) ficin-containing extraction buffer (10 mg/L) of varying pH values (7.5, 8.5, 9.5) along with increasing NaCl concentrations (0-3 M) for 5-45 minutes. Further experiments studied the necessity and optimal conditions and concentrations of EDTA and L-cystein as additives to the extraction buffer. Samples were incubated in the digestion mixture in the presence of 0-100 mM EDTA with 0-80 mM L-cystein for 1-3 h at 15° C., at pH 7.5 and without NaCl.

Fibrillogenesis: Fibrillogenesis is regarded as a collagen functionality test. Hence, the ability of purified collagen digested by ficin to form fibrils is an essential property of the obtained product. Test method: The pH of the collagen-containing solution (duplicate samples) was neutralized to pH 6.7 with sodium phosphate, pH 11.2, and then incubated at 27±2° C. for 6 hours. Samples were centrifuged to sediment the hydrogel which was formed. Protein concentration of both pre and post-neutralization (supernatant) samples was determined via the Lowry method. Purecol™ (Purchased from NUTACON, Cat No. 5409) was employed as positive control and gelatin as a negative control.

Example 1

Extraction and Purification of Collagen from Transgenic Plants in the Presence of Trypsin and Pepsin The production of human collagen in plants was initiated in order to avoid the use of collagen from mammalian sources since the use of mammalian proteins in human cosmetics or medical applications may be risky to human health as the evolutionary proximity is relativity close. The known disease Creutzfeldt-Jakob disease (CJD) is an example of one which is caused by consumption of infected mammal proteins by humans.

Initially, the purification of collagen from transgenic plants was performed using bovine pancreatic Trypsin and the digestive protease Pepsin, both of which catalyze the hydrolysis of proteins in the animal digestive system. The following examples illustrate the identification of a protease from a non-animal source suitable for use in the collagen purification process.

Results

Figure 1:
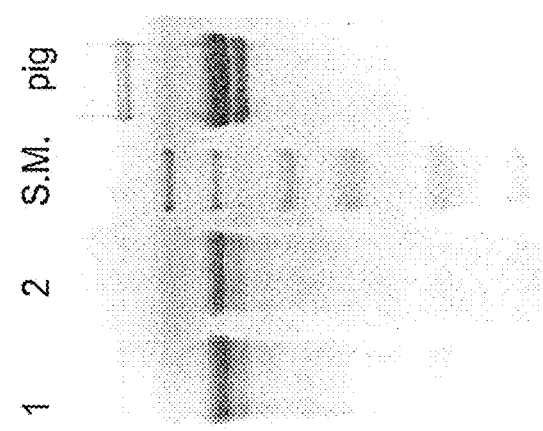
FIG. 1 Tobacco-leaf derived purified collagen following digestion with trypsin. Collagen was purified from the tobacco plant transgenic leaf line number 13-6 ground in 100 mM Tris buffer, centrifuged, proteolyzed and precipitated in a high salt concentration buffer, as detailed in the Material and Methods section. Following resuspension, collagen-containing pellets were washed, dialyzed and concentrated to the final product. This gel depicts a Coomassie stain analysis of the collected collagen samples where lanes 1 and 2 are the resulting collagen following digestion of procollagen with 300 mg/L Trypsin. Propeptide-free pig-derived collagen (0.5 mg/ml) was loaded and run as a positive control for collagen type 1 alpha 1 and alpha 2 chains.

Propeptide digestion during the purification of collagen was first performed by the pancreatic enzyme Trypsin. Trypsin, at 300 mg/L digested the collagen propeptides, however collagen yield was very low at the end of the purification process (FIG. 1). When the concentration of trypsin was lowered to 20 mg/L or 30 mg/L, the yield was higher, however procollagen digestion was only partial and inconsistent between identical samples (FIG. 2).

Figure 3:
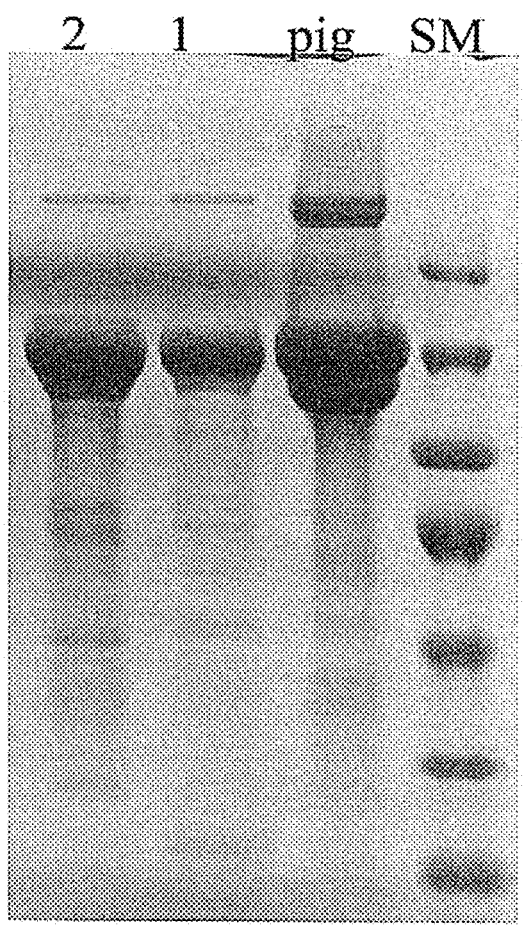
FIG. 3 Tobacco-leaf derived purified collagen following digestion with trypsin and pepsin. Collagen was extracted and purified as in FIG. 1 following digestion with 30 mg/L Trypsin and 1 µg/200 ml Pepsin (lanes 1-2). Products were separated on a 10% SDS PAGE and analyzed with a Coomassie-based staining solution. Propeptide-free pig-derived collagen (0.5 mg/ml) was loaded and run as a positive control for collagen type 1 alpha 1 and alpha 2 chains.
Figure 4:
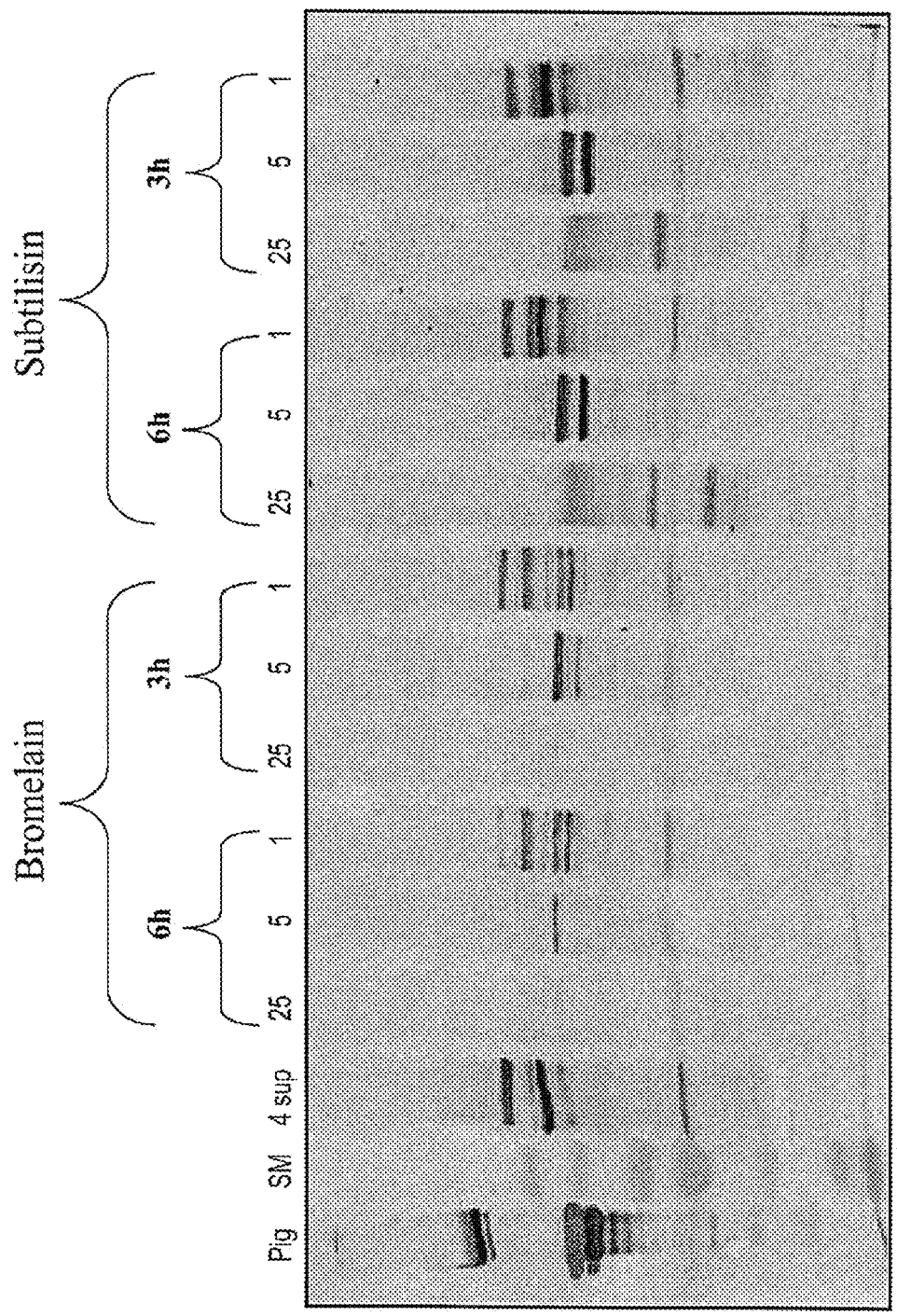
FIG. 4 Collagen chains obtained upon digestion of procollagen with Subtilisn or Bromelain. Collagen was purified from the tobacco plant transgenic leaf line number 13-361 ground in 100 mM Tris buffer, centrifuged and proteolyzed with either Subtilisin (1-25 mg/L) or Bromelain (1-25 mg/L) incubated for 3 or 6 hrs. Samples were separated on a 10% SDS PAGE and blotted to nitrocellulose membranes. Collagen chains were immunodetected using anti-collagen I. Untreated supernatants collected following homogenization and centrifugation served as collagen-free negative controls (lane 3-4sup). Propeptide-free pig-derived collagen (2.5 µg) served as a positive control for alpha 1 and alpha 2 chains (lane 1).

In an attempt to overcome this problem, varying incubation temperatures and times were tried; however the results did not lead to a change in yield (data not shown). The addition of Pepsin enzyme later on in the purification process resolved the partial digestion problem (FIG. 3) and yielded alpha 1 and alpha 2 collagen which co-migrated with pig-derived collagen control samples Example 2

Collagen Extraction and its Enzymatically-Induced Digestion

Figure 5:
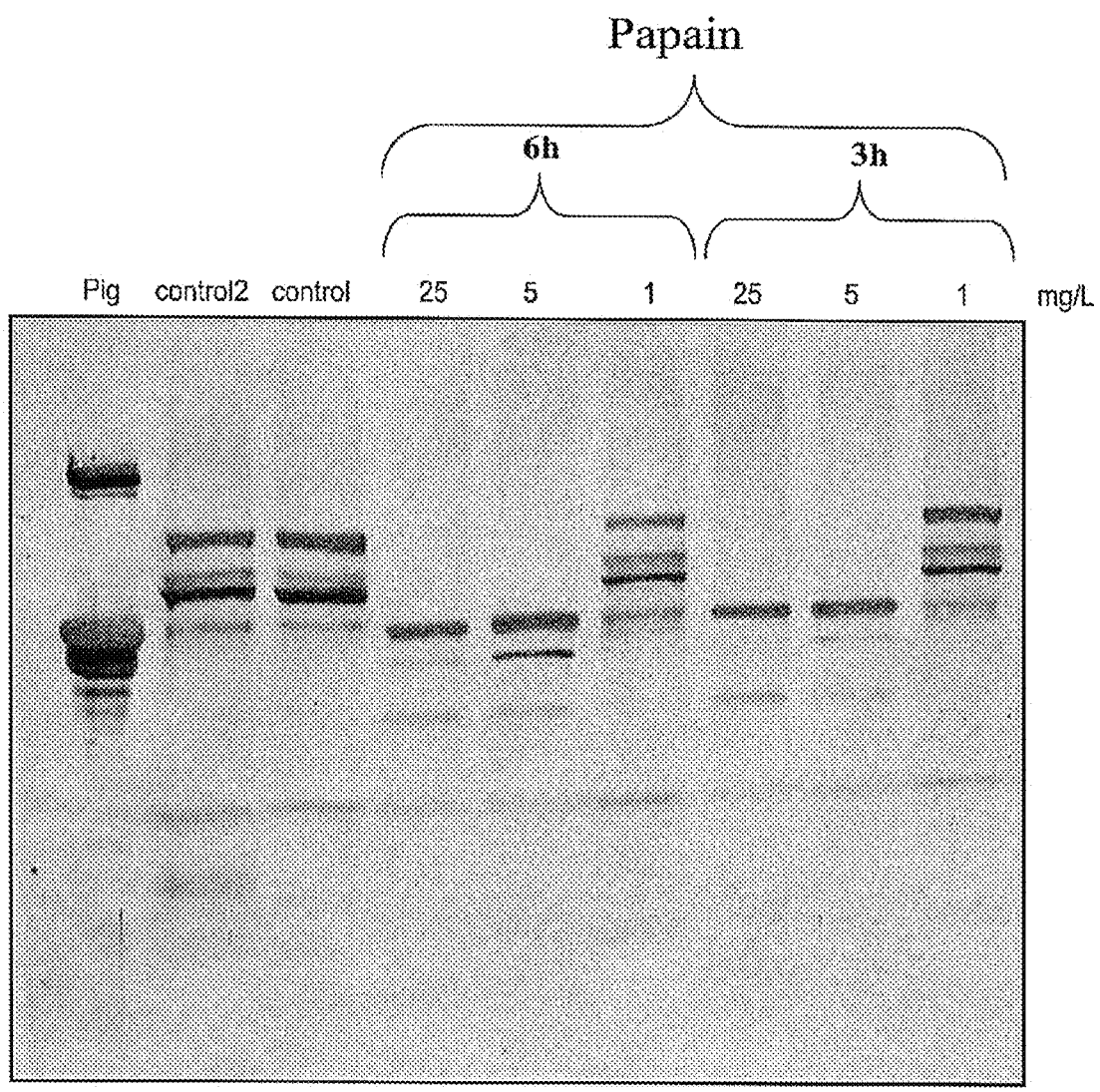
FIG. 5 Collagen chains obtained upon digestion of procollagen with Papain. Collagen was purified from the tobacco plant transgenic leaf line number 13-361 ground in 100 mM Tris buffer, centrifuged and proteolyzed with Papain (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected following homogenization, centrifugation and incubation at 15° C. for 3 hrs (lane 3) or 6 hrs (lane 2) with no enzyme served as collagen-free negative controls. Propeptide-free pig-derived collagen (2.5 µg) served as a positive control for alpha 1 and alpha 2 chains (lane 1).
Figure 6:
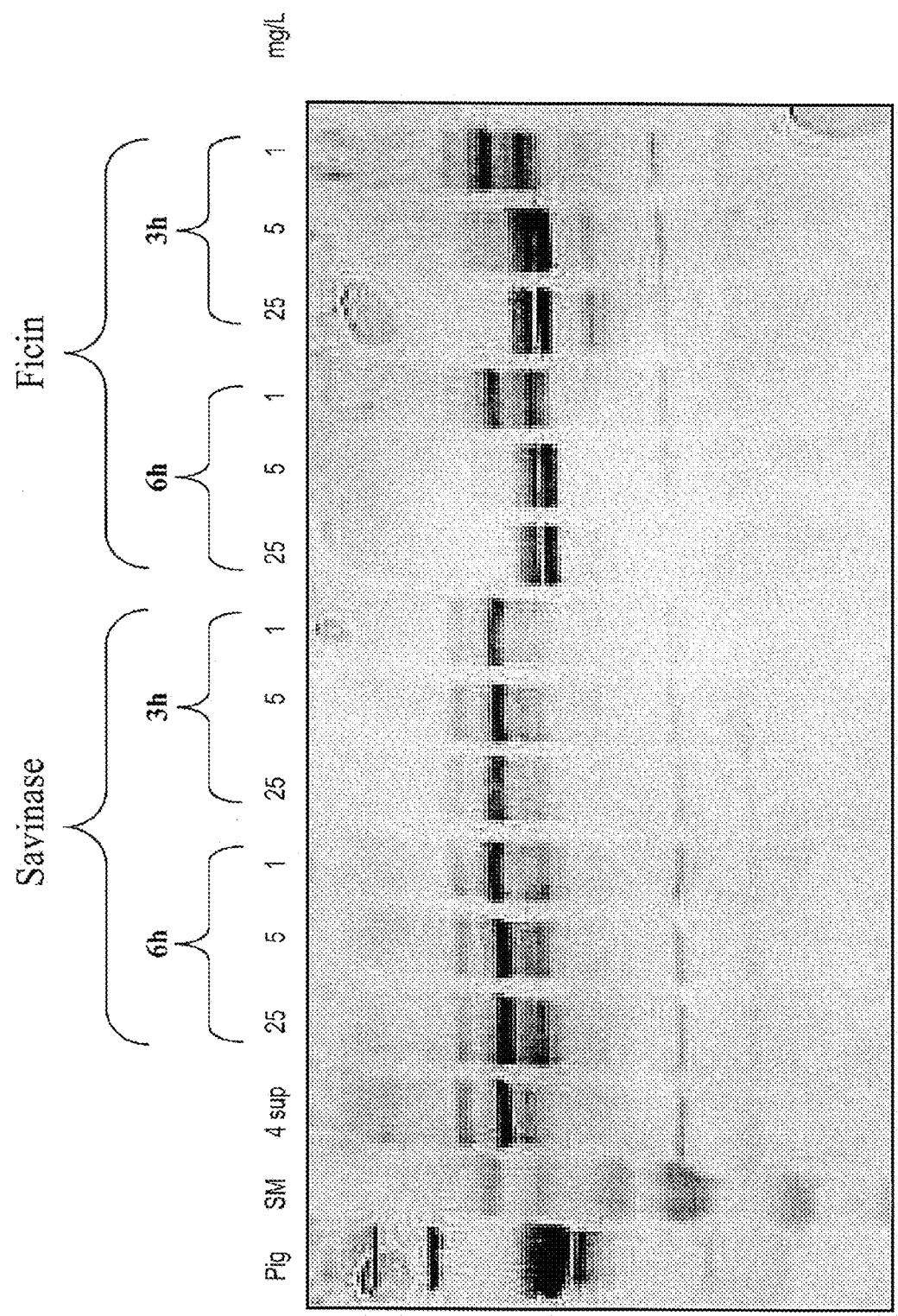
FIG. 6 Collagen chains obtained upon digestion of procollagen with Ficin or Savinase. Collagen was purified from the tobacco plant transgenic leaf line number 13-361 ground in 100 mM Tris buffer, centrifuged and proteolyzed with Ficin (1-25 mg/L) or Savinase (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected prior to proteolysis served as a collagen-free control sample (lane 3). Propeptide-free pig-derived collagen (2.5 µg) served as a positive control for alpha 1 and alpha 2 chains (lane 1).
Figure 7:
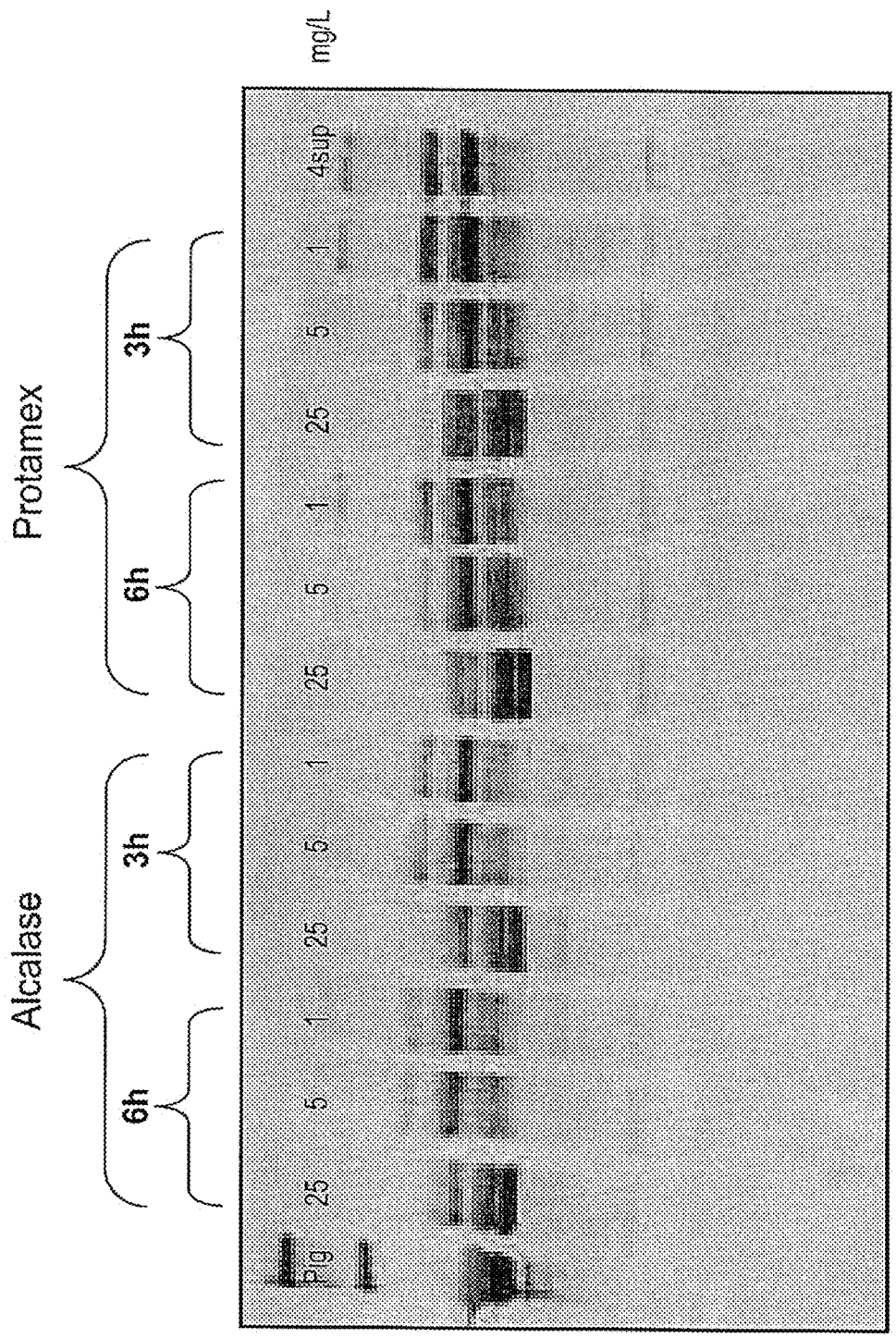
FIG. 7 Collagen chains obtained upon digestion of procollagen with Protamex or Alcalase. Collagen was purified from the tobacco plant transgenic leaf line number 13-361 ground in 100 mM Tris buffer, centrifuged and proteolyzed with Protamex (1-25 mg/L) or Alcalase (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected prior to proteolysis served as a collagen-free control sample (lane 14). Propeptide-free pig-derived collagen (2.5 µg) served as a positive control for alpha 1 and alpha 2 chains (lane 1).
Figure 8:
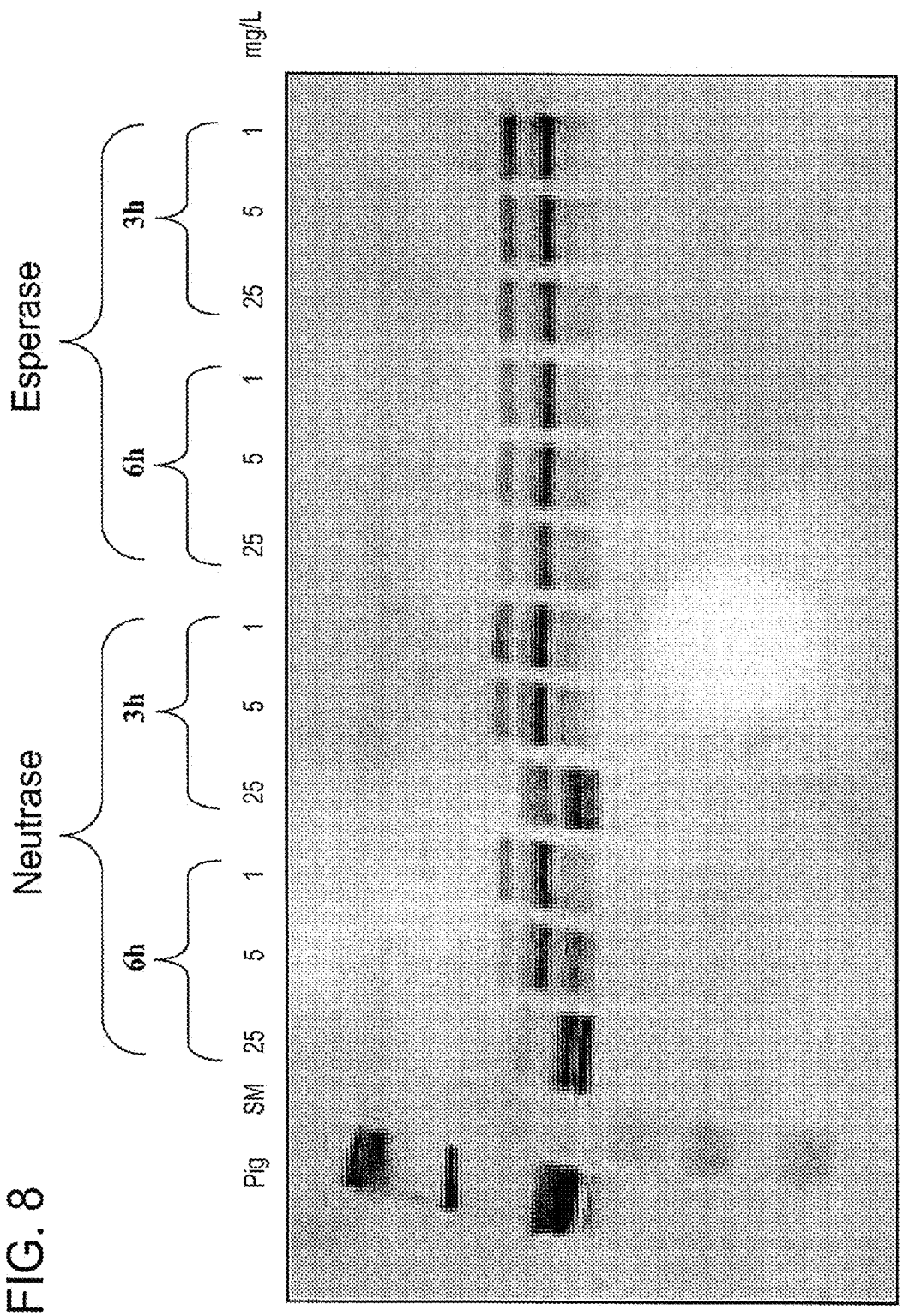
FIG. 8 Collagen chains obtained upon digestion of procollagen with Esperase or Neutrase. Collagen was purified from the tobacco plant transgenic leaf line number 13-361 ground in 100 mM Tris buffer, centrifuged and proteolyzed with Esperase (1-25 mg/L) or Neutrase (1-25 mg/L) following a 3 or 6 hrs incubation period. Samples were separated on a 10% SDS PAGE and blotted to nitrocellulose membranes. Collagen chains were immunodetected using anti-collagen I. Propeptide-free pig-derived collagen (2.5 µg) served as a positive control for alpha 1 and alpha 2 chains (lane 1).
Figure 9:
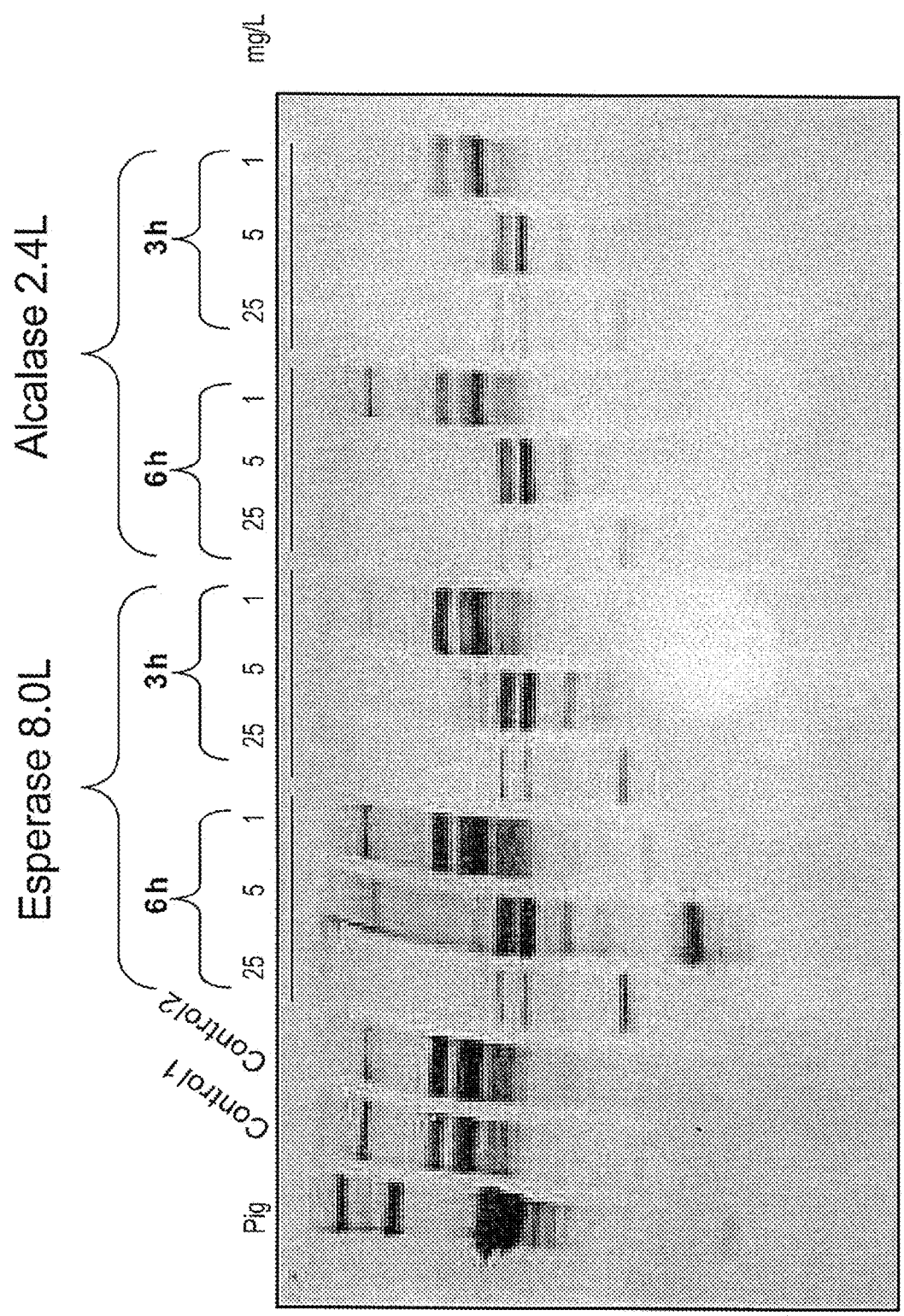
FIG. 9 Collagen chains obtained upon digestion of procollagen with Esperase 8.0 L or Alcalase. Collagen was purified from the tobacco plant transgenic leaf line number 13-361 ground in 100 mM Tris buffer, centrifuged and proteolyzed with Esperase (1-25 mg/L) or Neutrase (1-25 mg/L) following a 3 or 6 hrs incubation period. Samples were separated on a 10% SDS PAGE and blotted to nitrocellulose membranes. Collagen chains were immunodetected using anti-collagen I. Untreated supernatants collected following homogenization, centrifugation and incubation at 15° C. for 3 h (lane 3) or 6 h (lane 2) with no proteolytic enzyme served as collagen-free negative controls. Propeptide-free pig-derived collagen (2.5 µg) served as a positive control for alpha 1 and alpha 2 chains (lane 1).

However, the trypsin-pepsin solution was not optimal since it required two different enzymes, lengthening the purification process. Furthermore, both enzymes are from animal sources. In order to overcome these issues, a screen of different protease enzymes of non-animal origin, was performed. Varying digestion patterns were obtained by the different enzymes screened. Very little or no observable digestion of the propeptides resulted from the incubation of collagen with the Savinase (FIG. 6) and Esperase (FIG. 8) enzymes. Incubation with Papain (FIG. 5), Bromelain (FIG. 4), Alcalase 2.4 L and Esperase 8.0 L (FIG. 9), led to over- or under-digestion of the propeptides. Alcalase and Protamex enzymes (FIG. 7) led to the desired digestion pattern and level (25 mg/L, 6 hr), with alpha 1 and alpha 2 chains migrating similar to the pig-derived collagen sample. However, not all the molecules were fully digested and may require longer incubation periods. Optimal results were obtained upon procollagen incubation with Ficin (5 mg/L and 25 mg/L) (FIG. 6) where the bands of alpha 1 and alpha 2 chains comigrated with the pig-derived collagen control sample, with no apparent over-digestion. Similar results were demonstrated with Subtilisin 5 mg/L for 3 h (FIG. 4) and Neutrase 25 mg/L for 6 h (FIG. 8).

Example 3

Figure 10:
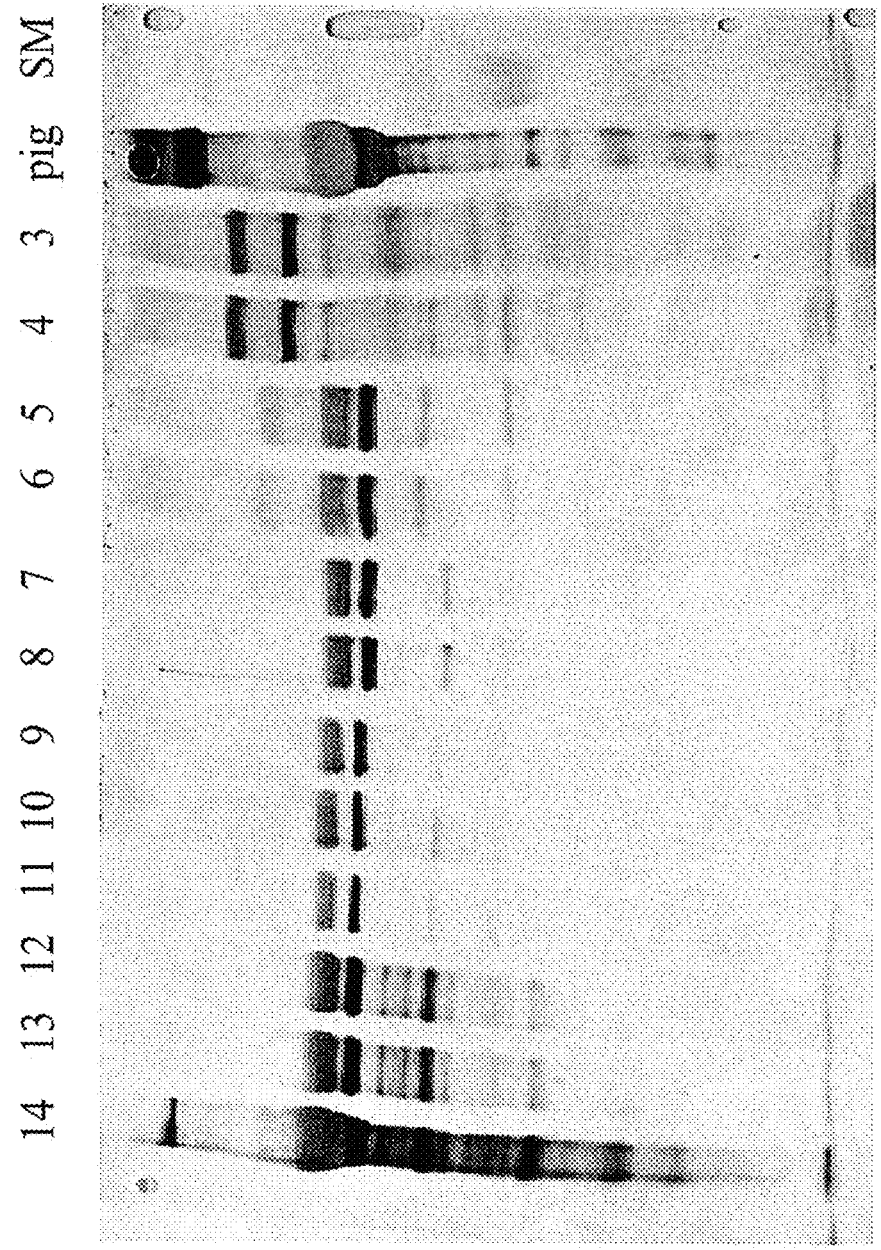
FIG. 10 Collagen chains obtained at various purification stages following digestion of procollagen with Ficin. Collagen was purified from the tobacco plant transgenic leaf line number 13-361 ground in 100 mM Tris buffer, centrifuged and proteolyzed with Ficin (5 mg/L) following a 3 hrs incubation period at 15° C. Samples were separated on a 10% SDS PAGE and blotted to nitrocellulose membranes. Collagen chains was immunodetected using anti-collagen I. Samples collected after grinding, centrifugation and incubation of supernatant with Ficin were loaded in lane 5. Lanes 6-14 depict samples of ficin-treated collagen at different stages in purification process: lane 6: sample post-ficin incubation and centrifugation; lane 7: following salt precipitation and resuspension in 0.5M acetic acid; lane 8: sample as in lane 7 with an added centrifugation step; lane 9: sample as in lane 8 following resuspension in 0.5 M acetic acid and centrifugation; lane 10: mature collagen following resuspension in 10 mM HCl and dialysis; lane 11: sample as in lane 10 with an additional filtration step; lane 12: sample as in lane 11 with an additional 5× concentration step; lane 13: sample as in lane 11 with an additional 20× concentration step; lane 14: sample as in lane 13 with additional 5× concentration step. Untreated procollagen samples (lanes 3-4) served as negative controls. Propeptide-free pig-derived collagen (2.5 µg) served as a positive control for alpha 1 and alpha 2 chains (lane 1).
Figure 11:
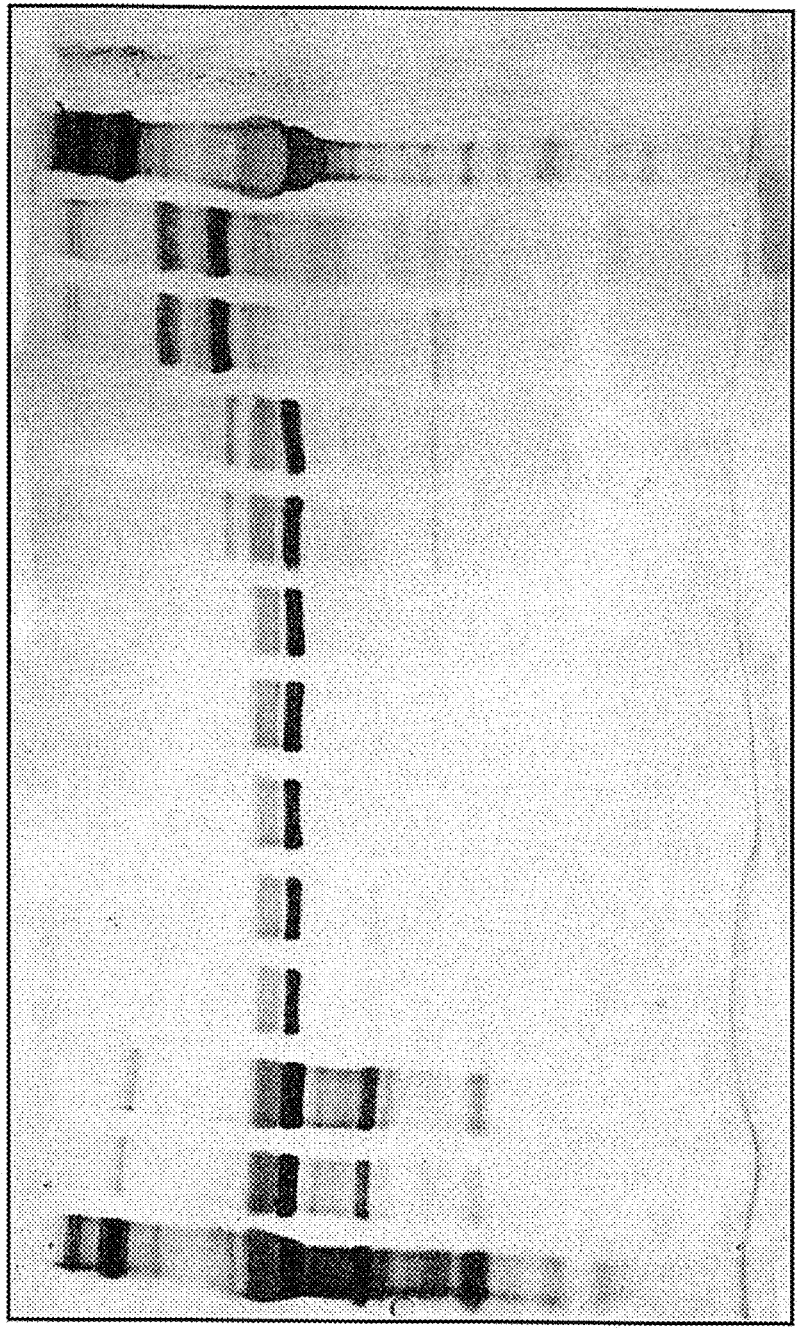
FIG. 11 Collagen chains obtained at various purification stages following digestion of procollagen with Subtilisin. Collagen was purified from the tobacco plant transgenic leaf line number 13-361 ground in 100 mM Tris buffer, centrifuged and proteolyzed with Subtilisin (5 mg/L) following a 3 hrs incubation period. Samples were separated on a 10% SDS PAGE and blotted to nitrocellulose membranes. Collagen chains was immunodetected using anti-collagen I. Samples collected after grinding, centrifugation and incubation of supernatant with Subtilisin (5 mg/L) were loaded in lane 5. Lanes 6-14 depict samples of subtilisin-treated collagen at different stages in purification process. lane 6: sample post-subtilisin incubation and centrifugation; lane 7: following salt precipitation and resuspension in 0.5M acetic acid; lane 8: sample as in lane 7 with an added centrifugation step; lane 9.

Extraction and Purification of Collagen from Transgenic Plants Following Digestion with Subtilisin or Ficin Collagen purifications from 450 gr leaves of transgenic plants (13-361 or 13-6-52) were performed followed by procollagen digestion with Ficin (FIG. 10) or Subtilisin (FIG. 11). Samples of the collagen at the various stages of the purification process were analyzed by Western analysis. Propeptide digestion by ficin and subtilisin led to the desirable degree of processing of Collagen 1 and Collagen 2. Bands of lower molecular weight were observed on the Western blots throughout the purification process, however, these bands appeared in the plant extracts prior to the incubation with the enzyme (lanes 3-4) and also in the pig-derived collagen control sample (positive control) (FIG. 10).

Example 4

Scaled Up Extraction and Purification of Collagen from Transgenic Plants Following Digestion with FICIN 1 kg of transgenic tobacco leaves were ground with pre chilled 2 L extraction buffer (100 mM sodium phosphate buffer pH 7.5, 4.5 mM potassium Meta disulfite, 12.23 mM L-cystein and 7.5 mM EDTA) in a 4 L reactor (ESCO model EL-3) for 20 minutes (5° C., 50% scraper speed and 100% homogenizer blade rpm). 6.68 g charcoal and 16.67 g of PVPP were added to the extract and continuously stirred for 20 minutes (5° C. and 50% scraper speed). Extract was centrifuged (11000 rpm, 5° C., 0.5 H) and supernatant was saturated with 15% ammonium sulfate (1 hour stirring, 5° C.). Following a 6880 rpm, 5° C., 30 min, the supernatant was saturated to 25% ammonium sulfate and stirred for 1 hour (5° C.). Following recentrifugation, the pellet (6880 rpm, 5° C., 30 min) was resuspended (in extraction buffer) in 15% of the volume collected after the first centrifugation step. Removal of propeptides was enabled by a 3 hr digestion, 15° C. with 5 mg/L ficin (Biochem Europe). The sample was centrifuged (11,000 rpm, 15° C., 30 min) and the mature collagen was precipitated using 3 M NaCl (NaCl was added slowly while stirring and left O.N. at 4° C.). Following precipitation (13, 000 rpm, 5° C., 2 hours), the supernatant was discarded and the pellet was resuspended in 0.5M acetic acid. Another round of 3M salting out (O.N) and centrifugation was followed by the resuspension of the pellets in 40 ml of 10 mM HCl. The sample was transferred to a dialysis bag (12-14 kDa) and dialyzed against 4 L 10 mM HCl, at 4° C., for 4 hours. The dialysis was repeated with fresh 4 L 10 mM HCl, O.N. The dialyzed solution was filtered through a 0.45μ filter (previously washed with 10 mM HCl) and then through a 0.25μ filter. The samples were finally concentrated in a Vivaspin (Vivascience) filtration tube (100 kDa).

Example 5

Solubility of Atelocollagen Produced as Recombinant Human Procollagen in Transgenic Tobacco Plants The concentration of atelocollagen generated according to Examples 3-4 was assayed by two methods as follows as described in the Methods section. The resulting concentrations obtained for several typical preparations digested with ficin, are listed in Table 2, herein below:

TABLE 2

Collagen concentrations as determined via the Instant blue or Sircol staining methods

| Lot No. | mg/ml collagen by Instant blue | mg/ml collagen by Sircol ™ |
|---|---|---|
| UPEK1 | 15.7 | 9.3 |
| UPEK2 | 5.8 | 4.78 |
| PEK052 | 6.8 | 5.5 |
| UPEK3 | 3.4 | 3.54 |
| UPEK4 | NA | 3.3 |
| UPEK6-1 | 5.9 | 4.7 |
| UPEK6-2 | 4.3 | 3.7 |

Example 6

Ficin-Dependent Proteolysis of Tobacco Leaf-Derived Procollagen

Digestion kinetics of procollagen by food-grade ficin: To calibrate appropriate ficin concentrations and incubation times allowing for highest collagen yields, procollagen-expressing tobacco leaf pellets were incubated with increasing concentrations of food-grade ficin (5-15 mg/L) at 15° C. for 1-3 hours. Samples were then analyzed by immunodetection of α1 and α2 collagen chains on Western blots. Increased ficin concentrations offered improvement in collagen chain yield following a 1 hour incubation period (FIG. 13, lane 5 vs. 6). However, upon extension of reaction time, increased ficin concentrations led to overdigestion of collagen (FIG. 13, lane 11 vs. 12-14 and lane 17 vs. 18-20). Thus, optimal conditions for digestion of procollagen to collagen were set at addition of 10 mg/L food-grade ficin for 1 hour at 15° C.

Digestion kinetics of procollagen by pharmaceutical-grade ficin: Similar experiments were carried out on procollagen-expressing tobacco leaf pellets to determine the appropriate conditions for procollagen digestion by pharmaceutical-grade ficin. Pellets were resuspended and incubated with increasing concentrations of pharmaceutical-grade ficin (2.5-10 mg/L), at 15° C. for 0.5-3 hrs. Digestion efficiency was determined by immunodetection of collagen chains on Western blots. As is shown in FIGS. 14A-C, increasing ficin concentrations led to increased collagen yield and decreased procollagen levels. The most effective digestion of procollagen with pharma-grade ficin was seen at 10 mg/L, after a 1 hour reaction time.

Optimization of pH values and salt concentrations for ficin-dependent procollagen cleavage: The contribution of both digestion buffer pH and salt concentrations were then evaluated. Similar tobacco leaf post-AMS pellets were resuspended in extraction buffer titrated to pH 5.5, 7.5, 8.5 or 9.5 with salt content ranging from 0.5-3 M NaCl. Samples were then incubated with 10 mg/L pharmaceutical-grade ficin at 15° C. for 1 hour prior to immunoanalysis on Western blots. Acidic assay conditions (pH 5.5) led to insufficient collagen yield (FIG. 15A, lanes 2-6), while increases in pH values demonstrated a correlative rise in ficin-dependent collagen content, with peak values observed at pH 8.5 in the presence of 2 M NaCl (FIG. 15B, lane 10). These results were further supported in a scale up extraction and purification experiment performed on two 15 kg pellets pooled for ficin-induced procollagen digestion. Aside from increased collagen chain yield as viewed by immunoblotting, samples digested in buffer of pH 8.5 in the presence of 2 M NaCl fibrillated just as efficiently as those digested in buffer A (pH 7.5, 0 mM NaCl) (see Table 3, herein below—batches YC1 and YC2). Thus, both higher pH and salt concentrations afford improved collagen yield following ficin-induced digestion of procollagen.

Determination of vitalness of EDTA and L-cystein in digestion reaction mixture: Both EDTA and L-cystein are additives present in the extraction buffer at early stages of the collagen purification process. Herein, the essentiality of these two components to effective ficin-dependent collagen cleavage was determined. Procollagen post-AMS pellets were resuspended in extraction buffer containing increasing concentrations of EDTA (8-80 mM) and L-cystein (10-100 mM), and incubated with ficin (10 mg/L) at 15° C. for 1 hour, at pH 7.5. A pronounced enhancing effect was observed on digestion efficiency in the presence of 10 mM L-cystein (FIG. 16, lanes 7-10), with no apparent contribution of EDTA to ficin-dependent collagen output (FIG. 16, lanes 7 vs. 8-10).

Optimization of temperature conditions for ficin-induced procollagen digestion: Procollagen-expressing tobacco leaf pellets were incubated with ficin for 1.5 hours at 15° C. and then transferred to a 30° C. bath for an additional 1.5 hours. Western blot and fibrillogenesis assays did not identify any improvement in collagen yield or sample purity related to increased reaction temperatures.

Fibrillogenesis of collagen extracted from ficin-induced cleavage of procollagen: Following ficin-induced digestion, fibrillogenesis assays were performed to determine the resultant collagen's ability to form fibrils, the ultimate method of determining the collagen's functionality. Table 3, herein below summarizes fibrillogenesis results as determined following ficin cleavage of procollagen using two variant protocols. Both protocols A and B, differing in reaction buffer pH and salt content yielded significant percentage of collagen fibrils. Thus, the proteolysis reaction parameters developed and optimized herein, lead to functional collagen at high yields.

TABLE 3

Percent fibrillogenesis observed by collagen obtained via digestion under varying conditions

| Batch # | Digestion conditions: | % Fibrillogenesis |
|---|---|---|
| C39 | Protocol A: 10 mg/L ficin, 1 hr, pH 7.5 | 94.1 |
| P100 | Protocol B: 10 mg/L ficin, pH 8.5, 2M NaCl, 1 hr | 87.2 |
| P101 | Protocol A | 73.1 |
| YC1 | Protocol A | 95.4 |
| YC2 | Protocol B | 98.4 |
| YC3 | Protocol A | 96 |
| YC4 | Protocol A | 93.1 |
| YC5 | Protocol A | 93.2 |
| YC7-8 | Protocol B | 94.2 |

Example 7

Determination of TrypZean™ Protease Efficacy in Procollagen Cleavage

Procollagen-expressing tobacco leaf pellets resuspended in extraction buffer (pH 7.5) enriched with EDTA (7.5 mM) and L-cystein (12.5 mM), were incubated with TrypZean™ (30-100 mg/L) for 1-3 hours at 15° C. Within 1 hour, doses of 60 and 100 mg/L TrypZean™ efficiently cleaved procollagen to yield two distinct alpha collagen chains, with no detectable over-digestion (FIG. 17). Thus, procollagen treatment with TrypZean™ at pH 7.5 lead to its effective digestion to collagen chains $\alpha 1$ and $\alpha 2$.

Discussion

The above examples describe the identification of a non-mammalian protease suitable for use in the process of purification of collagen derived from plants. Proteases from bacterial and plant sources were examined and three enzymes were found suitable for the collagen propeptides digestion, namely, neutrase, subtilisin, TrypZean™ and ficin.

Neutrase and Subtilisin are both secreted by the bacteria *Bacillus* sp. Subtilisin is primarily (>90%) used in detergents and household cleaning products. Approximately 10% of subtilisin use is towards technical applications such as protein hydrolysis, leather treatment, and in the textile and cosmetics industries. Standard use of subtilisin in the collagen purification process at higher concentration is problematic due to overdigestion of collagen. Neutrase is mainly used in the beverage alcohol industry and in cheese ripening. In the Examples described herein above, neutrase was only effective in digesting the propeptides at high concentrations and at least 6 hours were required for desirable digestion results.

Under the presently described experimental conditions, Recombinant trypsin and Ficin were found to be the most suitable among the four, since there was no overdigestion of collagen at either high enzyme concentrations or after extended incubation periods. Furthermore, these enzymes apparently did not digest the helical region of the collagen, as determined by SDS PAGE analysis. Ficin, being a natural enzyme extracted for Fig latec plant (*Ficus carica*), is available commercially at several grades including a pharmaceutical grade from several sources at low cost. It is used in the food industries: alcohol and beer industries, hydrolisation of proteins, meat processing, baking industry, and in the preparation of pet food and health food. It is also applied in the pharmaceutical industry in contact lens cleansers, cancer treatment, anti-arthritis treatments, and digestive aids as well as in the cosmetic and textile industries.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of generating atelocollagen from human procollagen which has accumulated in the vacuole of a plant, the method comprising contacting said human procollagen with ficin during or following extraction of said human procollagen from a cell of said plant, thereby generating the atelocollagen.

2. The method of claim 1, further comprising purifying the atelocollagen following said contacting to produce purified atelocollagen.

3. The method of claim 2, further comprising acid solubilizing said purified atelocollagen to generate soluble, purified atelocollagen.

4. The method of claim 3, wherein at least 70% of said soluble, purified atelocollagen is capable of forming fibrils.

* * * * *

```
                        SEQUENCE LISTING

<160> NUMBER OF SEQ ID NOS: 13

<210> SEQ ID NO 1
<211> LENGTH: 1464
<212> TYPE: PRT
<213> ORGANISM: Homo sapiens

<400> SEQUENCE: 1

Met Phe Ser Phe Val Asp Leu Arg Leu Leu Leu Leu Ala Ala Thr
1               5                   10                  15

Ala Leu Leu Thr His Gly Gln Glu Gly Gln Val Glu Gly Gln Asp
                20                  25                  30

Glu Asp Ile Pro Pro Ile Thr Cys Val Gln Asn Gly Leu Arg Tyr His
                35                  40                  45

Asp Arg Asp Val Trp Lys Pro Glu Pro Cys Arg Ile Cys Val Cys Asp
            50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
                115                 120                 125

Pro Gly Arg Asp Gly Ile Pro Gly Gln Pro Gly Leu Pro Gly Pro Pro
            130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
                195                 200                 205

Gly Glu Pro Gly Ala Ser Gly Pro Met Gly Pro Arg Gly Pro Pro Gly
            210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
                260                 265                 270

Leu Asp Gly Ala Lys Gly Asp Ala Gly Pro Ala Gly Pro Lys Gly Glu
            275                 280                 285

Pro Gly Ser Pro Gly Glu Asn Gly Ala Pro Gly Gln Met Gly Pro Arg
                290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
                340                 345                 350
```

```
Gly Glu Ala Gly Pro Gln Gly Pro Arg Gly Ser Glu Gly Pro Gln Gly
            355                 360                 365
Val Arg Gly Glu Pro Gly Pro Pro Gly Pro Ala Gly Ala Ala Gly Pro
        370                 375                 380
Ala Gly Asn Pro Gly Ala Asp Gly Gln Pro Gly Ala Lys Gly Ala Asn
385                 390                 395                 400
Gly Ala Pro Gly Ile Ala Gly Ala Pro Gly Phe Pro Gly Ala Arg Gly
                405                 410                 415
Pro Ser Gly Pro Gln Gly Pro Gly Pro Pro Gly Pro Lys Gly Asn
            420                 425                 430
Ser Gly Glu Pro Gly Ala Pro Gly Ser Lys Gly Asp Thr Gly Ala Lys
        435                 440                 445
Gly Glu Pro Gly Pro Val Gly Val Gln Gly Pro Pro Gly Pro Ala Gly
        450                 455                 460
Glu Glu Gly Lys Arg Gly Ala Arg Gly Glu Pro Gly Pro Thr Gly Leu
465                 470                 475                 480
Pro Gly Pro Pro Gly Glu Arg Gly Gly Pro Gly Ser Arg Gly Phe Pro
                485                 490                 495
Gly Ala Asp Gly Val Ala Gly Pro Lys Gly Pro Ala Gly Glu Arg Gly
            500                 505                 510
Ser Pro Gly Pro Ala Gly Pro Lys Gly Ser Pro Gly Glu Ala Gly Arg
            515                 520                 525
Pro Gly Glu Ala Gly Leu Pro Gly Ala Lys Gly Leu Thr Gly Ser Pro
        530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Pro Gly Pro Pro Gly Ala Arg Gly Gln
                565                 570                 575
Ala Gly Val Met Gly Phe Pro Gly Pro Lys Gly Ala Ala Gly Glu Pro
            580                 585                 590
Gly Lys Ala Gly Glu Arg Gly Val Pro Gly Pro Pro Gly Ala Val Gly
        595                 600                 605
Pro Ala Gly Lys Asp Gly Glu Ala Gly Ala Gln Gly Pro Pro Gly Pro
        610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                645                 650                 655
Lys Pro Gly Glu Gln Gly Val Pro Gly Asp Leu Gly Ala Pro Gly Pro
            660                 665                 670
Ser Gly Ala Arg Gly Glu Arg Gly Phe Pro Gly Glu Arg Gly Val Gln
            675                 680                 685
Gly Pro Pro Gly Pro Ala Gly Pro Arg Gly Ala Asn Gly Ala Pro Gly
        690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
                725                 730                 735
Gly Leu Pro Gly Pro Lys Gly Asp Arg Gly Asp Ala Gly Pro Lys Gly
            740                 745                 750
Ala Asp Gly Ser Pro Gly Lys Asp Gly Val Arg Gly Leu Thr Gly Pro
            755                 760                 765
Ile Gly Pro Pro Gly Pro Ala Gly Ala Pro Gly Asp Lys Gly Glu Ser
```

```
                770               775                 780
Gly Pro Ser Gly Pro Ala Gly Pro Thr Gly Ala Arg Gly Ala Pro Gly
785                 790                 795                 800

Asp Arg Gly Glu Pro Gly Pro Gly Pro Ala Gly Phe Ala Gly Pro
            805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Gly Pro Ala Gly Pro Ala Gly
            835                 840                 845

Pro Pro Gly Pro Ile Gly Asn Val Gly Ala Pro Gly Ala Lys Gly Ala
            850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
            885                 890                 895

Pro Pro Gly Pro Ala Gly Lys Glu Gly Lys Gly Pro Arg Gly Glu
            900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
            965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
            995                 1000                1005

Pro Gly Glu Ser Gly Arg Glu Gly Ala Pro Gly Ala Glu Gly Ser
    1010                1015                1020

Pro Gly Arg Asp Gly Ser Pro Gly Ala Lys Gly Asp Arg Gly Glu
    1025                1030                1035

Thr Gly Pro Ala Gly Pro Pro Gly Ala Pro Gly Ala Pro Gly Ala
    1040                1045                1050

Pro Gly Pro Val Gly Pro Ala Gly Lys Ser Gly Asp Arg Gly Glu
    1055                1060                1065

Thr Gly Pro Ala Gly Pro Ala Gly Pro Val Gly Pro Val Gly Ala
    1070                1075                1080

Arg Gly Pro Ala Gly Pro Gln Gly Pro Arg Gly Asp Lys Gly Glu
    1085                1090                1095

Thr Gly Glu Gln Gly Asp Arg Gly Ile Lys Gly His Arg Gly Phe
    1100                1105                1110

Ser Gly Leu Gln Gly Pro Pro Gly Pro Pro Gly Ser Pro Gly Glu
    1115                1120                1125

Gln Gly Pro Ser Gly Ala Ser Gly Pro Ala Gly Pro Arg Gly Pro
    1130                1135                1140

Pro Gly Ser Ala Gly Ala Pro Gly Lys Asp Gly Leu Asn Gly Leu
    1145                1150                1155

Pro Gly Pro Ile Gly Pro Pro Gly Pro Arg Gly Arg Thr Gly Asp
    1160                1165                1170

Ala Gly Pro Val Gly Pro Pro Gly Pro Pro Gly Pro Pro Gly Pro
    1175                1180                1185
```

```
Pro Gly Pro Pro Ser Ala Gly Phe Asp Phe Ser Phe Leu Pro Gln
    1190            1195                1200

Pro Pro Gln Glu Lys Ala His Asp Gly Gly Arg Tyr Tyr Arg Ala
    1205            1210                1215

Asp Asp Ala Asn Val Val Arg Asp Arg Asp Leu Glu Val Asp Thr
    1220            1225                1230

Thr Leu Lys Ser Leu Ser Gln Gln Ile Glu Asn Ile Arg Ser Pro
    1235            1240                1245

Glu Gly Ser Arg Lys Asn Pro Ala Arg Thr Cys Arg Asp Leu Lys
    1250            1255                1260

Met Cys His Ser Asp Trp Lys Ser Gly Glu Tyr Trp Ile Asp Pro
    1265            1270                1275

Asn Gln Gly Cys Asn Leu Asp Ala Ile Lys Val Phe Cys Asn Met
    1280            1285                1290

Glu Thr Gly Glu Thr Cys Val Tyr Pro Thr Gln Pro Ser Val Ala
    1295            1300                1305

Gln Lys Asn Trp Tyr Ile Ser Lys Asn Pro Lys Asp Lys Arg His
    1310            1315                1320

Val Trp Phe Gly Glu Ser Met Thr Asp Gly Phe Gln Phe Glu Tyr
    1325            1330                1335

Gly Gly Gln Gly Ser Asp Pro Ala Asp Val Ala Ile Gln Leu Thr
    1340            1345                1350

Phe Leu Arg Leu Met Ser Thr Glu Ala Ser Gln Asn Ile Thr Tyr
    1355            1360                1365

His Cys Lys Asn Ser Val Ala Tyr Met Asp Gln Gln Thr Gly Asn
    1370            1375                1380

Leu Lys Lys Ala Leu Leu Leu Gln Gly Ser Asn Glu Ile Glu Ile
    1385            1390                1395

Arg Ala Glu Gly Asn Ser Arg Phe Thr Tyr Ser Val Thr Val Asp
    1400            1405                1410

Gly Cys Thr Ser His Thr Gly Ala Trp Gly Lys Thr Val Ile Glu
    1415            1420                1425

Tyr Lys Thr Thr Lys Thr Ser Arg Leu Pro Ile Ile Asp Val Ala
    1430            1435                1440

Pro Leu Asp Val Gly Ala Pro Asp Gln Glu Phe Gly Phe Asp Val
    1445            1450                1455

Gly Pro Val Cys Phe Leu
    1460

<210> SEQ ID NO 2
<211> LENGTH: 1366
<212> TYPE: PRT
<213> ORGANISM: Homo sapiens

<400> SEQUENCE: 2

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
                35                  40                  45

Pro Pro Gly Arg Asp Gly Glu Asp Gly Pro Thr Gly Pro Pro Gly Pro
        50                  55                  60

Pro Gly Pro Pro Gly Pro Pro Gly Leu Gly Gly Asn Phe Ala Ala Gln
```

```
            65                  70                  75                  80
Tyr Asp Gly Lys Gly Val Gly Leu Gly Pro Gly Pro Met Gly Leu Met
                        85                  90                  95
Gly Pro Arg Gly Pro Gly Ala Ala Gly Ala Pro Gly Pro Gln Gly
                100                 105                 110
Phe Gln Gly Pro Ala Gly Glu Pro Gly Glu Pro Gly Gln Thr Gly Pro
            115                 120                 125
Ala Gly Ala Arg Gly Pro Ala Gly Pro Pro Gly Lys Ala Gly Glu Asp
        130                 135                 140
Gly His Pro Gly Lys Pro Gly Arg Pro Gly Glu Arg Gly Val Val Gly
145                 150                 155                 160
Pro Gln Gly Ala Arg Gly Phe Pro Gly Thr Pro Gly Leu Pro Gly Phe
                    165                 170                 175
Lys Gly Ile Arg Gly His Asn Gly Leu Asp Gly Leu Lys Gly Gln Pro
                180                 185                 190
Gly Ala Pro Gly Val Lys Gly Glu Pro Gly Ala Pro Gly Glu Asn Gly
            195                 200                 205
Thr Pro Gly Gln Thr Gly Ala Arg Gly Leu Pro Gly Glu Arg Gly Arg
        210                 215                 220
Val Gly Ala Pro Gly Pro Ala Gly Ala Arg Gly Ser Asp Gly Ser Val
225                 230                 235                 240
Gly Pro Val Gly Pro Ala Gly Pro Ile Gly Ser Ala Gly Pro Pro Gly
                    245                 250                 255
Phe Pro Gly Ala Pro Gly Pro Lys Gly Glu Ile Gly Ala Val Gly Asn
                260                 265                 270
Ala Gly Pro Ala Gly Pro Ala Gly Pro Arg Gly Glu Val Gly Leu Pro
            275                 280                 285
Gly Leu Ser Gly Pro Val Gly Pro Pro Gly Asn Pro Gly Ala Asn Gly
        290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Val Gly Ala Ala
                    325                 330                 335
Gly Ala Thr Gly Ala Arg Gly Leu Val Gly Glu Pro Gly Pro Ala Gly
                340                 345                 350
Ser Lys Gly Glu Ser Gly Asn Lys Gly Glu Pro Gly Ser Ala Gly Pro
            355                 360                 365
Gln Gly Pro Pro Gly Pro Ser Gly Glu Glu Gly Lys Arg Gly Pro Asn
        370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
                    405                 410                 415
Met Gly Pro Pro Gly Ser Arg Gly Ala Ser Gly Pro Ala Gly Val Arg
                420                 425                 430
Gly Pro Asn Gly Asp Ala Gly Arg Pro Gly Glu Pro Gly Leu Met Gly
            435                 440                 445
Pro Arg Gly Leu Pro Gly Ser Pro Gly Asn Ile Gly Pro Ala Gly Lys
        450                 455                 460
Glu Gly Pro Val Gly Leu Pro Gly Ile Asp Gly Arg Pro Gly Pro Ile
465                 470                 475                 480
Gly Pro Ala Gly Ala Arg Gly Glu Pro Gly Asn Ile Gly Phe Pro Gly
                    485                 490                 495
```

-continued

Pro Lys Gly Pro Thr Gly Asp Pro Gly Lys Asn Gly Asp Lys Gly His
        500                 505                 510

Ala Gly Leu Ala Gly Ala Arg Gly Ala Pro Gly Pro Asp Gly Asn Asn
        515                 520                 525

Gly Ala Gln Gly Pro Pro Gly Pro Gln Gly Val Gln Gly Gly Lys Gly
        530                 535                 540

Glu Gln Gly Pro Ala Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
            565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
            595                 600                 605

Arg Gly Pro Ser Gly Pro Pro Gly Pro Asp Gly Asn Lys Gly Glu Pro
        610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Leu Lys Gly Glu
            645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685

Ala Thr Gly Asp Arg Gly Glu Ala Gly Ala Ala Gly Pro Ala Gly Pro
        690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
            725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765

Gly Pro Pro Gly Pro Ala Gly Ser Arg Gly Asp Gly Gly Pro Pro Gly
        770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
            805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845

Ser Gly Glu Ala Gly Thr Ala Gly Pro Pro Gly Thr Pro Gly Pro Gln
        850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
            885                 890                 895

Leu Gly Ile Ala Gly Pro Pro Gly Ala Arg Gly Pro Pro Gly Ala Val
            900                 905                 910

-continued

```
Gly Ser Pro Gly Val Asn Gly Pro Gly Glu Ala Gly Arg Asp Gly
            915                 920                 925

Asn Pro Gly Asn Asp Gly Pro Pro Gly Arg Asp Gly Gln Pro Gly His
930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly Pro Gln Gly Ile Arg Gly Asp Lys
            995                 1000                1005

Gly Glu Pro Gly Glu Lys Gly Pro Arg Gly Leu Pro Gly Leu Lys
         1010                1015                1020

Gly His Asn Gly Leu Gln Gly Leu Pro Gly Ile Ala Gly His His
         1025                1030                1035

Gly Asp Gln Gly Ala Pro Gly Ser Val Gly Pro Ala Gly Pro Arg
         1040                1045                1050

Gly Pro Ala Gly Pro Ser Gly Pro Ala Gly Lys Asp Gly Arg Thr
         1055                1060                1065

Gly His Pro Gly Thr Val Gly Pro Ala Gly Ile Arg Gly Pro Gln
         1070                1075                1080

Gly His Gln Gly Pro Ala Gly Pro Pro Gly Pro Pro Gly Pro Pro
         1085                1090                1095

Gly Pro Pro Gly Val Ser Gly Gly Gly Tyr Asp Phe Gly Tyr Asp
         1100                1105                1110

Gly Asp Phe Tyr Arg Ala Asp Gln Pro Arg Ser Ala Pro Ser Leu
         1115                1120                1125

Arg Pro Lys Asp Tyr Glu Val Asp Ala Thr Leu Lys Ser Leu Asn
         1130                1135                1140

Asn Gln Ile Glu Thr Leu Leu Thr Pro Glu Gly Ser Arg Lys Asn
         1145                1150                1155

Pro Ala Arg Thr Cys Arg Asp Leu Arg Leu Ser His Pro Glu Trp
         1160                1165                1170

Ser Ser Gly Tyr Tyr Trp Ile Asp Pro Asn Gln Gly Cys Thr Met
         1175                1180                1185

Asp Ala Ile Lys Val Tyr Cys Asp Phe Ser Thr Gly Glu Thr Cys
         1190                1195                1200

Ile Arg Ala Gln Pro Glu Asn Ile Pro Ala Lys Asn Trp Tyr Arg
         1205                1210                1215

Ser Ser Lys Asp Lys Lys His Val Trp Leu Gly Glu Thr Ile Asn
         1220                1225                1230

Ala Gly Ser Gln Phe Glu Tyr Asn Val Glu Gly Val Thr Ser Lys
         1235                1240                1245

Glu Met Ala Thr Gln Leu Ala Phe Met Arg Leu Leu Ala Asn Tyr
         1250                1255                1260

Ala Ser Gln Asn Ile Thr Tyr His Cys Lys Asn Ser Ile Ala Tyr
         1265                1270                1275

Met Asp Glu Glu Thr Gly Asn Leu Lys Lys Ala Val Ile Leu Gln
         1280                1285                1290

Gly Ser Asn Asp Val Glu Leu Val Ala Glu Gly Asn Ser Arg Phe
         1295                1300                1305

Thr Tyr Thr Val Leu Val Asp Gly Cys Ser Lys Lys Thr Asn Glu
```

Trp Gly Lys Thr Ile Ile Glu Tyr Lys Thr Asn Lys Pro Ser Arg
    1325              1330                1335

Leu Pro Phe Leu Asp Ile Ala Pro Leu Asp Ile Gly Gly Ala Asp
    1340              1345                1350

Gln Glu Phe Phe Val Asp Ile Gly Pro Val Cys Phe Lys
    1355              1360                1365

<210> SEQ ID NO 3
<211> LENGTH: 5927
<212> TYPE: DNA
<213> ORGANISM: Homo sapiens

<400> SEQUENCE: 3

| | | | | | |
|---|---|---|---|---|---|
| tcgtcggagc | agacgggagt | ttctcctcgg | ggtcggagca | ggaggcacgc | ggagtgtgag | 60 |
| gccacgcatg | agcggacgct | aaccccctcc | ccagccacaa | agagtctaca | tgtctagggt | 120 |
| ctagacatgt | tcagctttgt | ggacctccgg | ctcctgctcc | tcttagcggc | caccgccctc | 180 |
| ctgacgcacg | gccaagagga | aggccaagtc | gagggccaag | acgaagacat | cccaccaatc | 240 |
| acctgcgtac | agaacggcct | caggtaccat | gaccgagacg | tgtggaaacc | cgagccctgc | 300 |
| cggatctgcg | tctgcgacaa | cggcaaggtg | ttgtgcgatg | acgtgatctg | tgacgagacc | 360 |
| aagaactgcc | ccgcgccga | agtccccgag | ggcgagtgct | gtccgtctg | ccccgacggc | 420 |
| tcagagtcac | ccaccgacca | agaaaccacc | ggcgtcgagg | acccaaggg | agacactggc | 480 |
| ccccgaggcc | caaggggacc | cgcaggcccc | cctggccgag | atggcatccc | tggacagcct | 540 |
| ggacttcccg | gacccccgg | acccccgga | cctcccggac | cccctggcct | cggaggaaac | 600 |
| tttgctcccc | agctgtctta | tggctatgat | gagaaatcaa | ccggaggaat | ttccgtgcct | 660 |
| ggccccatgg | gtccctctgg | tcctcgtggt | ctccctggcc | cccctggtgc | acctggtccc | 720 |
| caaggcttcc | aaggtccccc | tggtgagcct | ggcgagcctg | gagcttcagg | tcccatgggt | 780 |
| ccccgaggtc | ccccaggtcc | cctggaaag | aatggagatg | atgggaagc | tggaaaacct | 840 |
| ggtcgtcctg | gtgagcgtgg | gcctcctggg | cctcagggtg | ctcgaggatt | gcccggaaca | 900 |
| gctggcctcc | ctggaatgaa | gggacacaga | ggtttcagtg | gtttggatgg | tgccaaggga | 960 |
| gatgctggtc | ctgctggtcc | taagggtgag | cctggcagcc | ctggtgaaaa | tggagctcct | 1020 |
| ggtcagatgg | gccccgtgg | cctgcctggt | gagagaggtc | gccctggagc | ccctggccct | 1080 |
| gctggtgctc | gtggaaatga | tggtgctact | ggtgctgccg | gccccctgg | tccaccggc | 1140 |
| cccgctggtc | ctcctggctt | ccctggtgct | gttggtgcta | agggtgaagc | tggtcccaa | 1200 |
| gggccccgag | gctctgaagg | tcccagggt | gtgcgtggtg | agcctggccc | cctggccct | 1260 |
| gctggtgctc | ctgccctgc | tggaaaccct | ggtgctgatg | gacagcctgg | tgctaaaggt | 1320 |
| gccaatggtg | ctcctggtat | tgctggtgct | cctggcttcc | ctggtgcccg | aggccctct | 1380 |
| ggaccccagg | gccccggcgg | ccctcctggt | cccaaggta | acagcggtga | acctggtgct | 1440 |
| cctggcagca | aaggagacac | tggtgctaag | ggagagcctg | gccctgttgg | tgttcaagga | 1500 |
| ccccctggcc | ctgctggaga | ggaaggaaag | cgaggagctc | gaggtgaacc | cggacccact | 1560 |
| ggcctgcccg | gaccccctgg | cgagcgtggt | ggacctggta | gccgtggttt | ccctggcgca | 1620 |
| gatggtgttg | ctggtcccaa | gggtcccgct | ggtgaacgtg | gttctcctgg | ccctgctggc | 1680 |
| cccaaaggat | ctcctggtga | agctggtcgt | cccggtgaag | ctggtctgcc | tggtgccaag | 1740 |
| ggtctgactg | gaagccctgg | cagccctggt | cctgatggca | aaactggccc | cctggtccc | 1800 |

```
gccggtcaag atggtcgccc cggaccccca ggcccacctg gtgcccgtgg tcaggctggt      1860
gtgatgggat ccctggacc taaaggtgct gctggagagc ccggcaaggc tggagagcga      1920
ggtgttcccg acccctgg cgctgtcggt cctgctggca aagatggaga ggctggagct       1980
cagggacccc ctggccctgc tggtcccgct ggcgagagag gtgaacaagg ccctgctggc     2040
tcccccggat tccagggtct ccctggtcct gctggtcctc caggtgaagc aggcaaacct    2100
ggtgaacagg gtgttcctgg agaccttggc gcccctggcc cctctggagc aagaggcgag    2160
agaggtttcc ctggcgagcg tggtgtgcaa ggtccccctg gtcctgctgg tccccgaggg    2220
gccaacggtg ctcccggcaa cgatggtgct aagggtgatg ctggtgcccc tggagctccc   2280
ggtagccagg gcgcccctgg ccttcaggga atgcctggtg aacgtggtgc agctggtctt    2340
ccagggccta agggtgacag aggtgatgct ggtcccaaag gtgctgatgg ctctcctggc   2400
aaagatggcg tccgtggtct gactggcccc attggtcctc ctggccctgc tggtgcccct   2460
ggtgacaagg gtgaaagtgg tcccagcggc cctgctggtc ccactggagc tcgtggtgcc   2520
cccggagacc gtggtgagcc tggtcccccc ggccctgctg gctttgctgg ccccctggt    2580
gctgacggcc aacctggtgc taaaggcgaa cctggtgatg ctggtgctaa aggcgatgct   2640
ggtcccctg gccctgccgg acccgctgga ccccctggcc ccattggtaa tgttggtgct    2700
cctggagcca aggtgctcg cggcagcgct ggtcccctg gtgctactgg tttccctggt    2760
gctgctggcc gagtcggtcc tcctggcccc tctggaaatg ctggacccc tggccctcct   2820
ggtcctgctg gcaaagaagg cggcaaaggt ccccgtggtg agactggccc tgctggacgt   2880
cctggtgaag ttggtcccc tggtcccct ggccctgctg gcgagaaagg atccctggt    2940
gctgatggtc ctgctggtgc tcctggtact cccgggcctc aaggtattgc tggacagcgt   3000
ggtgtggtcg gcctgcctgg tcagagagga gagagaggct tccctggtct tcctggcccc   3060
tctggtgaac ctggcaaaca aggtccctct ggagcaagtg gtgaacgtgg tccccctggt   3120
cccatgggcc cccctggatt ggctggaccc cctggtgaat ctggacgtga gggggctcct   3180
ggtgccgaag gttcccctgg acgagacggt tctcctggcg ccaagggtga ccgtggtgag   3240
accggccccg ctggaccccc tggtgctcct ggtgctcctg gtgcccctgg ccccgttggc   3300
cctgctggca agagtggtga tcgtggtgag actggtcctg ctggtcccgc cggtcctgtc   3360
ggccctgttg gcgcccgtgg ccccgccgga cccaaggcc ccgtggtga caagggtgag   3420
acaggcgaac agggcgacag aggcataaag ggtcaccgtg gcttctctgg cctccagggt   3480
cccctggcc ctcctggctc tcctggtgaa caaggtcct ctggagcctc tggtcctgct    3540
ggtcccgag gtcccctgg ctctgctggt gctcctggca aagatggact caacggtctc    3600
cctggcccca ttgggccccc tggtcctcgc ggtcgcactg gtgatgctgg tcctgttggt   3660
cccccggcc ctcctggacc tcctggtccc ctggtcctc ccagcgctgg tttcgacttc    3720
agcttcctgc cccagccacc tcaagagaag gctcacgatg gtggccgcta ctaccgggct   3780
gatgatgcca atgtggttcg tgaccgtgac ctcgaggtgg acaccaccct caagagcctg   3840
agccagcaga tcgagaacat ccggagccca gagggcagcc gcaagaaccc cgcccgcacc   3900
tgccgtgacc tcaagatgtg ccactctgac tggaagagtg gagagtactg gattgacccc   3960
aaccaaggct gcaacctgga tgccatcaaa gtcttctgca acatggagac tggtgagacc   4020
tgcgtgtacc ccactcagcc cagtgtggcc cagaagaact ggtacatcag caagaacccc   4080
aaggacaaga ggcatgtctg gttcggcgag agcatgaccg atggattcca gttcgagtat   4140
ggcggccagg gctccgaccc tgccgatgtg gccatccagc tgaccttcct gcgcctgatg   4200
```

```
tccaccgagg cctcccagaa catcacctac cactgcaaga acagcgtggc ctacatggac    4260
cagcagactg gcaacctcaa gaaggccctg ctcctccagg gctccaacga gatcgagatc    4320
cgcgccgagg gcaacagccg cttcacctac agcgtcactg tcgatggctg cacgagtcac    4380
accggagcct ggggcaagac agtgattgaa tacaaaacca ccaagacctc ccgcctgccc    4440
atcatcgatg tggcccccctt ggacgttggt gccccagacc aggaattcgg cttcgacgtt    4500
ggccctgtct gcttcctgta aactcccctcc atcccaacct ggctccctcc cacccaacca    4560 actttcccccc caacccggaa acagacaagc aacccaaact gaaccccctc aaaagccaaa    4620
aaatgggaga caatttcaca tggacttttgg aaaatatttt tttcctttgc attcatctct    4680
caaacttagt ttttatcttt gaccaaccga acatgaccaa aaaccaaaag tgcattcaac    4740
cttaccaaaa aaaaaaaaaa aaaaagaata aataataac ttttttaaaaa aggaagcttg    4800 gtccacttgc ttgaagaccc atgcgggggt aagtcccttt ctgcccgttg ggcttatgaa    4860 acccccaatgc tgccctttct gctcctttct ccacacccccc cttgggggcct ccctccact    4920 ccttcccaaa tctgtctccc cagaagacac aggaaacaat gtattgtctg cccagcaatc    4980
aaaggcaatg ctcaaacacc caagtggccc ccaccctcag cccgctcctg cccgcccagc    5040 accccccaggc cctgggggac ctggggttct cagactgcca aagaagcctt gccatctggc    5100
gctcccatgg ctcttgcaac atctccccctt cgttttttgag ggggtcatgc cggggggagcc    5160 accagccccct cactgggttc ggaggagagt caggaagggc cacgacaaag cagaaacatc    5220
ggatttgggg aacgcgtgtc aatcccttgt gccgcagggc tgggcgggag agactgttct    5280
gttccttgtg taactgtgtt gctgaaagac tacctcgttc ttgtcttgat gtgtcaccgg    5340
ggcaactgcc tgggggcggg gatgggggca gggtggaagc ggctccccat tttataccaa    5400
aggtgctaca tctatgtgat gggtggggtg gggagggaat cactggtgct atagaaattg    5460
agatgccccc ccaggccagc aaatgttcct ttttgttcaa agtctatttt tattccttga    5520 tattttttctt ttttttttttt tttttttgtg gatggggact tgtgaatttt tctaaaggtg    5580
ctatttaaca tggaggagaa gcgtgtgcgg ctccagccca gcccgctgct cactttccac    5640
cctctctcca cctgcctctg gcttctcagg cctctgctct ccgacctctc tcctctgaaa    5700
ccctcctcca cagctgcagc ccatcctccc ggctccctcc tagtctgtcc tgcgtcctct    5760
gtccccgggt ttcagagaca acttcccaaa gcacaaagca gttttttcccc ctaggggtgg    5820 gaggaagcaa aagactctgt acctatttttg tatgtgtata ataatttgag atgtttttaa    5880
ttattttgat tgctggaata aagcatgtgg aaatgaccca aacataa                  5927

<210> SEQ ID NO 4
<211> LENGTH: 5411
<212> TYPE: DNA
<213> ORGANISM: Homo sapiens

<400> SEQUENCE: 4
gtgtcccata gtgtttccaa acttggaaag ggcgggggag ggcgggagga tgcggagggc     60
ggaggtatgc agacaacgag tcagagtttc cccttgaaag cctcaaaagt gtccacgtcc    120
tcaaaaagaa tggaaccaat ttaagaagcc agccccgtgg ccacgtccct tccccccattc    180 gctccctcct ctgcgccccc gcaggctcct cccagctgtg gctgcccggg ccccccagccc    240 cagccctccc attggtggag gccctttttgg aggcaccccta gggccaggga aacttttgcc    300
gtataaatag ggcagatccg ggcttttatta tttttagcacc acggcagcag gaggtttcgg    360
```

| | |
|---|---|
| ctaagttgga ggtactggcc acgactgcat gcccgcgccc gccaggtgat acctccgccg | 420 |
| gtgacccagg ggctctgcga cacaaggagt ctgcatgtct aagtgctaga catgctcagc | 480 |
| tttgtggata cgcggacttt gttgctgctt gcagtaacct tatgcctagc aacatgccaa | 540 |
| tctttacaag aggaaactgt aagaaagggc ccagccggag atagaggacc acgtggagaa | 600 |
| aggggtccac caggcccccc aggcagagat ggtgaagatg gtcccacagg ccctcctggt | 660 |
| ccacctggtc ctcctggccc ccctggtctc ggtgggaact tgctgctcca gtatgatgga | 720 |
| aaaggagttg gacttggccc tggaccaatg ggcttaatgg gacctagagg cccacctggt | 780 |
| gcagctggag ccccaggccc tcaaggtttc caaggacctg ctggtgagcc tggtgaacct | 840 |
| ggtcaaactg gtcctgcagg tgctcgtggt ccagctggcc ctcctggcaa ggctggtgaa | 900 |
| gatggtcacc ctggaaaacc cggacgacct ggtgagagag gagttgttgg accacagggt | 960 |
| gctcgtggtt ccctggaac tcctggactt cctggcttca aaggcattag ggacacaat | 1020 |
| ggtctgatg gattgaaggg acagcccggt gctcctggtg tgaagggtga acctggtgcc | 1080 |
| cctggtgaaa atggaactcc aggtcaaaca ggagcccgtg ggcttcctgg tgagagagga | 1140 |
| cgtgttggtg ccctggccc agctggtgcc cgtggcagtg atggaagtgt gggtcccgtg | 1200 |
| ggtcctgctg gtcccattgg gtctgctggc cctccaggct tcccaggtgc ccctggcccc | 1260 |
| aagggtgaaa ttggagctgt tggtaacgct ggtcctgctg gtcccgccgg tccccgtggt | 1320 |
| gaagtgggtc ttccaggcct ctccggcccc gttggacctc ctggtaatcc tggagcaaac | 1380 |
| ggccttactg gtgccaaggg tgctgctggc cttcccggcg ttgctggggc tcccggcctc | 1440 |
| cctggacccc gcggtattcc tggccctgtt ggtgctgccg gtgctactgg tgccagagga | 1500 |
| cttgttggtg agcctggtcc agctggctcc aaaggagaga gcggtaacaa gggtgagccc | 1560 |
| ggctctgctg ggccccaagg tcctcctggt cccagtggtg aagaaggaaa gagaggccct | 1620 |
| aatggggaag ctggatctgc cggccctcca ggacctcctg ggctgagagg tagtcctggt | 1680 |
| tctcgtggtc ttcctggagc tgatggcaga gctggcgtca tgggccctcc tggtagtcgt | 1740 |
| ggtgcaagtg gccctgctgg agtccgagga cctaatggag atgctggtcg ccctggggag | 1800 |
| cctggtctca tgggacccag aggtcttcct ggttcccctg gaaatatcgg ccccgctgga | 1860 |
| aaagaaggtc ctgtcggcct cccggcatc gacggcaggc ctggcccaat ggcccagct | 1920 |
| ggagcaagag gagagcctgg caacattgga ttccctggac ccaaaggccc cactggtgat | 1980 |
| cctggcaaaa acggtgataa aggtcatgct ggtcttgctg gtgctcgggg tgctccaggt | 2040 |
| cctgatggaa acaatggtgc tcagggacct cctggaccac aggtgttcca aggtggaaaa | 2100 |
| ggtgaacagg gtccccctgg tcctccaggc ttcagggtc tgcctggccc ctcaggtccc | 2160 |
| gctggtgaag ttggcaaacc aggagaaagg ggtctccatg gtgagtttgg tctccctggt | 2220 |
| cctgctggtc aagaggggga acgcggtccc ccaggtgaga gtggtgctgc cggtcctact | 2280 |
| ggtcctattg gaagccgagg tccttctgga ccccaggggc ctgatggaaa caagggtgaa | 2340 |
| cctggtgtgg ttggtgctgt gggcactgct ggtccatctg gtcctagtgg actcccagga | 2400 |
| gagagggtg ctgctggcat acctggaggc aagggagaaa aggtgaacc tggtctcaga | 2460 |
| ggtgaaattg gtaaccctgg cagagatggt gctcgtggtg ctcctggtgc tgtaggtgcc | 2520 |
| cctggtcctg ctggagccac aggtgaccgg ggcgaagctg gggctgctgg tcctgctggt | 2580 |
| cctgctggtc ctcggggaag ccctggtgaa cgtggtgagg tcggtcctgc tggccccaat | 2640 |
| ggatttgctg gtcctgctgg tgctgctggt caacctggtg ctaaaggaga aagaggagcc | 2700 |
| aaagggccta agggtgaaaa cggtgttgtt ggtcccacag gccccgttgg agctgctggc | 2760 |

```
ccagctggtc caaatggtcc ccccggtcct gctggaagtc gtggtgatgg aggccccccT    2820
ggtatgactg gtttccctgg tgctgctgga cggactggtc ccccaggacc ctctggtatt    2880
tctggccctc ctggtccccc tggtcctgct gggaaagaag gcttcgtgg tcctcgtggt    2940 gaccaaggtc cagttggccg aactggagaa gtaggtgcag ttggtccccc tggcttcgct    3000
ggtgagaagg gtccctctgg agaggctggt actgctggac ctcctggcac tccaggtcct    3060
cagggtcttc ttggtgctcc tggtattctg ggtctccctg gctcgagagg tgaacgtggt    3120
ctaccaggtg ttgctggtgc tgtgggtgaa cctggtcctc ttggcattgc cggccctcct    3180
gggggccgtg gtcctcctgg tgctgtgggt agtcctggag tcaacggtgc tcctggtgaa    3240
gctggtcgtg atggcaaccc tgggaacgat ggtcccccag gtcgcgatgg tcaacccgga    3300
cacaagggag agcgcggtta ccctggcaat attggtcccg ttggtgctgc aggtgcacct    3360
ggtcctcatg gccccgtggg tcctgctggc aaacatggaa accgtggtga aactggtcct    3420
tctggtcctg ttggtcctgc tggtgctgtt ggcccaagag gtcctagtgg cccacaaggc    3480
attcgtggcg ataagggaga gcccggtgaa aaggggccca gaggtcttcc tggcttaaag    3540
ggacacaatg gattgcaagg tctgcctggt atcgctggtc accatggtga tcaaggtgct    3600
cctggctccg tgggtcctgc tggtcctagg ggccctgctg gtccttctgg ccctgctgga    3660
aaagatggtc gcactggaca tcctggtaca gttggacctg ctggcattcg aggccctcag    3720
ggtcaccaag gccctgctgg ccccctggt ccccctggcc ctcctggacc tccaggtgta    3780
agcggtggtg gttatgactt tggttacgat ggagacttct acagggctga ccagcctcgc    3840
tcagcacctt ctctcagacc caaggactat gaagttgatg ctactctgaa gtctctcaac    3900
aaccagattg agacccttct tactcctgaa ggctctagaa agaacccagc tcgcacatgc    3960
cgtgacttga gactcagcca cccagagtgg agcagtggtt actactggat tgaccctaac    4020
caaggatgca ctatgatgc tatcaaagta tactgtgatt tctctactgg cgaaacctgt    4080
atccgggccc aacctgaaaa catcccagcc aagaactggt ataggagctc caaggacaag    4140
aaacacgtct ggctaggaga aactatcaat gctggcagcc agtttgaata taatgtagaa    4200
ggagtgactt ccaaggaaat ggctacccaa cttgccttca tgcgcctgct ggccaactat    4260
gcctctcaga acatcaccta ccactgcaag aacagcattg catacatgga tgaggagact    4320
ggcaacctga aaaaggctgt cattctacag ggctctaatg atgttgaact tgttgctgag    4380
ggcaacagca ggttcactta cactgttctt gtagatggct gctctaaaaa gacaaatgaa    4440
tggggaaaga caatcattga atacaaaaca aataagccat cacgcctgcc cttccttgat    4500
attgcacctt tggacatcgg tggtgctgac caggaattct tgtggacat tggcccagtc    4560 tgtttcaaat aaatgaactc aatctaaatt aaaaagaaa gaaatttgaa aaactttct    4620 ctttgccatt tcttcttctt ctttttaac tgaaagctga atccttccat ttcttctgca    4680
catctacttg cttaaattgt gggcaaaaga gaaaagaag gattgatcag agcattgtgc    4740
aatacagttt cattaactcc ttcccccgct cccccaaaaa tttgaattt ttttttcaaca    4800 ctcttacacc tgttatggaa aatgtcaacc tttgtaagaa aaccaaaata aaaattgaaa    4860
aataaaaacc ataaacattt gcaccacttg tggcttttga atatcttcca cagagggaag    4920
tttaaaaccc aaacttccaa aggtttaaac tacctcaaaa cactttccca tgagtgtgat    4980
ccacattgtt aggtgctgac ctagacagag atgaactgag gtccttgttt tgttttgttc    5040
ataatacaaa ggtgctaatt aatagtattt cagatacttg aagaatgttg atggtgctag    5100
```

```
aagaatttga agaaatac tcctgtattg agttgtatcg tgtggtgtat tttttaaaaa    5160
atttgattta gcattcatat tttccatctt attcccaatt aaaagtatgc agattatttg    5220
cccaaatctt cttcagattc agcatttgtt ctttgccagt ctcattttca tcttcttcca    5280
tggttccaca gaagctttgt ttcttgggca agcagaaaaa ttaaattgta cctatttgt     5340 atatgtgaga tgtttaaata aattgtgaaa aaatgaaat aaagcatgtt tggttttcca     5400
aaagaacata t                                                          5411
```

<210> SEQ ID NO 5
<211> LENGTH: 1633
<212> TYPE: DNA
<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the human Prolyl
      4-hydroxylase beta subunit and flanking regions

<400> SEQUENCE: 5

```
ctcgagtaaa ccatggctca tgctagggtt ttgcttttgg ctcttgctgt tcttgctact    60
gctgctgttg ctgtggcttc ttcttcatct ttcgctgatt ctaacccaat taggccagtg    120
actgatagag ctgcttctac tcttgctcaa ttggtcgaca tggatgctcc agaagaggag    180
gatcacgttc ttgtgcttag gaagtctaac ttcgctgaag ctcttgctgc tcacaagtac    240
cttcttgtgg agttttatgc tccttggtgc ggacattgca aagctcttgc tccagagtat    300
gctaaggctg ctggaaagtt gaaggctgag ggatctgaaa ttaggcttgc taaagtggat    360
gctactgagg agtctgatct tgctcaacag tacggagtta ggggataccc aactattaag    420
ttcttcagga acgagatac tgcttctcca aaggagtata ctgctggaag ggaggctgat    480
gatattgtga actggcttaa aagagaact ggaccagctg ctactactct tccagatgga    540
gctgctgctg aatctcttgt ggagtcatct gaggtggcag tgattggatt cttcaaggat    600
gtggagtctg attctgctaa gcagttcctt caagctgctg aggctattga tgatattcca    660
ttcggaatta cttctaactc tgatgtgttc tctaagtacc agcttgataa ggatggagtg    720
gtgcttttca agaaattcga tgagggaagg aacaatttcg agggagaggt gacaaaggag    780
aaccttcttg atttcattaa gcacaaccag cttccacttg tgattgagtt cactgagcag    840
actgctccaa agatttttcgg aggagagatt aagactcaca ttcttcttttt ccttccaaag    900 tctgtgtctg attacgatgg aaagttgtct aacttcaaga ctgctgctga gtctttcaag    960 ggaaagatc tttttcatttt cattgattct gatcacactg ataaccagag gattcttgag    1020
ttcttcggac ttaagaagga gagtgcccca gctgttaggc ttattactct tgaggaggag    1080
atgactaagt acaagccaga gtctgaagaa cttactgctg agaggattac tgagttctgc    1140
cacagattcc ttgagggaaa gattaagcca caccttatgt ctcaagagct tccagaggat    1200
tgggataagc agccagttaa ggtgttggtg ggtaaaaaact tcgaggatgt ggctttcgat    1260
gagaagaaga acgtgttcgt ggagttctac gcaccttggt gtggtcactg taagcagctt    1320
gctccaattt gggataagtt gggagagact acaaggatc acgagaacat tgtgattgct    1380
aagatggatt ctactgctaa cgaggtggag gctgttaagg ttcactcttt cccaactttg    1440
aagttcttcc cagcttctgc tgataggact gtgattgatt acaacggaga aaggactctt    1500
gatggattca agaagttcct tgagtctgga ggacaagatg gagctggaga tgatgatgat    1560
cttgaggatt tggaagaagc tgaggagcca gatatggagg aggatgatga tcagaaggct    1620
```

```
gtgtgatgag ctc                                                      1633
```

<210> SEQ ID NO 6
<211> LENGTH: 1723
<212> TYPE: DNA
<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the human Prolyl
      4-hydroxylase alpha-1 subunit and flanking regions

<400> SEQUENCE: 6

```
ctcgagtaaa ccatggctca tgctagggtt ttgcttttgg ctcttgctgt tcttgctact     60
gctgctgttg ctgtggcttc ttcttcatct ttcgctgatt ctaacccaat taggccagtg    120
actgatagag ctgcttctac tcttgctcaa ttggtcgaca tgcacccagg attcttcact    180
tctattggac agatgactga tcttattcac actgagaagg atcttgtgac ttctcttaag    240
gattacatta aggctgagga ggataagttg gagcagatta agaagtgggc tgagaagttg    300
gataggctta cttctactgc tacaaaagat ccagagggat tcgttggtca tccagtgaac    360
gctttcaagt tgatgaagag gcttaacact gagtggagtg agcttgagaa ccttgtgctt    420
aaggatatgt ctgatggatt catttctaac cttactattc agaggcagta cttcccaaat    480
gatgaggatc aagtgggagc tgctaaggct cttcttaggc ttcaggatac ttacaacctt    540
gatactgata caatttctaa gggaaacctt ccaggagtta agcacaagtc tttccttact    600
gctgaggatt gcttcgagct tggaaaggtt gcatacactg aggctgatta ctaccacact    660
gagcttttgga tggaacaagc tcttaggcaa cttgatgagg agagatttc tactattgat    720
aaggtgtcag tgcttgatta cctttcttac gctgtgtacc agcagggtga tcttgataag    780
gctcttttgc ttactaagaa gttgcttgag cttgatccag aacatcagag ggctaacgga    840
aaccttaagt acttcgagta cattatggct aaggaaaagg atgtgaacaa gtctgcttct    900
gatgatcagt ctgatcaaaa gactactcca agaagaaagg gagtggctgt tgattatctt    960
cctgagaggc agaagtatga gatgttgtgt aggggagagg gtattaagat gactccaagg   1020
aggcagaaga agttgttctg caggtatcac gatggaaaca ggaacccaaa gttcattctt   1080
gctccagcta gcaagaaga tgagtgggat aagccaagga ttattaggtt ccacgatatt   1140
atttctgatg ctgagattga gattgtgaag gatcttgcta gccaagact taggagggct   1200
actatttcta acccatcttc tggtgatctt gagactgtgc actacaggat ttctaagtct   1260
gcttggcttt ctggatacga gaacccagtg gtgtctagga ttaacatgag gattcaggat   1320
cttactggac ttgatgtgtc tactgctgag gagcttcaag ttgctaacta cggagttgga   1380
ggacaatatg agccacactt cgatttcgct aggaaggatg agccagatgc ttttaaggag   1440
cttggaactg gaaacaggat tgctacttgg cttttctaca tgtctgatgt ttctgctgga   1500
ggagctactg ttttcccaga agtgggagct tctgtttggc caagaaaggg aactgctgtg   1560
ttctggtaca accttttcgc ttctggagag ggagattact ctactaggca tgctgcttgc   1620
ccagttcttg ttggaaacaa gtgggtgtca aacaagtggc ttcatgagag gggacaagag   1680
tttagaaggc catgcactct ttctgagctt gagtgatgag ctc                    1723
```

<210> SEQ ID NO 7
<211> LENGTH: 1489
<212> TYPE: PRT
<213> ORGANISM: Homo sapiens

<400> SEQUENCE: 7

```
Met Ala His Ala Arg Val Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ser Thr Leu Ala Gln Leu Gln
            35                  40                  45

Glu Glu Gly Gln Val Glu Gly Gln Asp Glu Asp Ile Pro Pro Ile Thr
    50                  55                  60

Cys Val Gln Asn Gly Leu Arg Tyr His Asp Arg Asp Val Trp Lys Pro
65                  70                  75                  80

Glu Pro Cys Arg Ile Cys Val Cys Asp Asn Gly Lys Val Leu Cys Asp
                85                  90                  95

Asp Val Ile Cys Asp Glu Thr Lys Asn Cys Pro Gly Ala Glu Val Pro
            100                 105                 110

Glu Gly Glu Cys Cys Pro Val Cys Pro Asp Gly Ser Glu Ser Pro Thr
            115                 120                 125

Asp Gln Glu Thr Thr Gly Val Glu Gly Pro Lys Gly Asp Thr Gly Pro
    130                 135                 140

Arg Gly Pro Arg Gly Pro Ala Gly Pro Pro Gly Arg Asp Gly Ile Pro
145                 150                 155                 160

Gly Gln Pro Gly Leu Pro Gly Pro Pro Gly Pro Pro Gly Pro Pro Gly
                165                 170                 175

Pro Pro Gly Leu Gly Gly Asn Phe Ala Pro Gln Leu Ser Tyr Gly Tyr
            180                 185                 190

Asp Glu Lys Ser Thr Gly Gly Ile Ser Val Pro Gly Pro Met Gly Pro
    195                 200                 205

Ser Gly Pro Arg Gly Leu Pro Gly Pro Pro Gly Ala Pro Gly Pro Gln
210                 215                 220

Gly Phe Gln Gly Pro Pro Gly Glu Pro Gly Glu Pro Gly Ala Ser Gly
225                 230                 235                 240

Pro Met Gly Pro Arg Gly Pro Pro Gly Pro Pro Gly Lys Asn Gly Asp
                245                 250                 255

Asp Gly Glu Ala Gly Lys Pro Gly Arg Pro Gly Glu Arg Gly Pro Pro
            260                 265                 270

Gly Pro Gln Gly Ala Arg Gly Leu Pro Gly Thr Ala Gly Leu Pro Gly
    275                 280                 285

Met Lys Gly His Arg Gly Phe Ser Gly Leu Asp Gly Ala Lys Gly Asp
290                 295                 300

Ala Gly Pro Ala Gly Pro Lys Gly Glu Pro Gly Ser Pro Gly Glu Asn
305                 310                 315                 320

Gly Ala Pro Gly Gln Met Gly Pro Arg Gly Leu Pro Gly Glu Arg Gly
                325                 330                 335

Arg Pro Gly Ala Pro Gly Pro Ala Gly Ala Arg Gly Asn Asp Gly Ala
            340                 345                 350

Thr Gly Ala Ala Gly Pro Pro Gly Pro Thr Gly Pro Ala Gly Pro Pro
    355                 360                 365

Gly Phe Pro Gly Ala Val Gly Ala Lys Gly Glu Ala Gly Pro Gln Gly
370                 375                 380

Pro Arg Gly Ser Glu Gly Pro Gln Gly Val Arg Gly Glu Pro Gly Pro
385                 390                 395                 400

Pro Gly Pro Ala Gly Ala Ala Gly Pro Ala Gly Asn Pro Gly Ala Asp
                405                 410                 415
```

```
Gly Gln Pro Gly Ala Lys Gly Ala Asn Gly Ala Pro Gly Ile Ala Gly
            420                 425                 430

Ala Pro Gly Phe Pro Gly Ala Arg Gly Pro Ser Gly Pro Gln Gly Pro
            435                 440                 445

Gly Gly Pro Pro Gly Pro Lys Gly Asn Ser Gly Glu Pro Gly Ala Pro
            450                 455                 460

Gly Ser Lys Gly Asp Thr Gly Ala Lys Gly Glu Pro Gly Pro Val Gly
465                 470                 475                 480

Val Gln Gly Pro Pro Gly Pro Ala Gly Glu Glu Gly Lys Arg Gly Ala
            485                 490                 495

Arg Gly Glu Pro Gly Pro Thr Gly Leu Pro Gly Pro Pro Gly Glu Arg
            500                 505                 510

Gly Gly Pro Gly Ser Arg Gly Phe Pro Gly Ala Asp Gly Val Ala Gly
            515                 520                 525

Pro Lys Gly Pro Ala Gly Glu Arg Gly Ser Pro Gly Pro Ala Gly Pro
            530                 535                 540

Lys Gly Ser Pro Gly Glu Ala Gly Arg Pro Gly Glu Ala Gly Leu Pro
545                 550                 555                 560

Gly Ala Lys Gly Leu Thr Gly Ser Pro Gly Ser Pro Gly Pro Asp Gly
            565                 570                 575

Lys Thr Gly Pro Pro Gly Pro Ala Gly Gln Asp Gly Arg Pro Gly Pro
            580                 585                 590

Pro Gly Pro Pro Gly Ala Arg Gly Gln Ala Gly Val Met Gly Phe Pro
            595                 600                 605

Gly Pro Lys Gly Ala Ala Gly Glu Pro Gly Lys Ala Gly Glu Arg Gly
            610                 615                 620

Val Pro Gly Pro Pro Gly Ala Val Gly Pro Ala Gly Lys Asp Gly Glu
625                 630                 635                 640

Ala Gly Ala Gln Gly Pro Pro Gly Pro Ala Gly Pro Ala Gly Glu Arg
            645                 650                 655

Gly Glu Gln Gly Pro Ala Gly Ser Pro Gly Phe Gln Gly Leu Pro Gly
            660                 665                 670

Pro Ala Gly Pro Pro Gly Glu Ala Gly Lys Pro Gly Glu Gln Gly Val
            675                 680                 685

Pro Gly Asp Leu Gly Ala Pro Gly Pro Ser Gly Ala Arg Gly Glu Arg
            690                 695                 700

Gly Phe Pro Gly Glu Arg Gly Val Gln Gly Pro Pro Gly Pro Ala Gly
705                 710                 715                 720

Pro Arg Gly Ala Asn Gly Ala Pro Gly Asn Asp Gly Ala Lys Gly Asp
            725                 730                 735

Ala Gly Ala Pro Gly Ala Pro Gly Ser Gln Gly Ala Pro Gly Leu Gln
            740                 745                 750

Gly Met Pro Gly Glu Arg Gly Ala Ala Gly Leu Pro Gly Pro Lys Gly
            755                 760                 765

Asp Arg Gly Asp Ala Gly Pro Lys Gly Ala Asp Gly Ser Pro Gly Lys
            770                 775                 780

Asp Gly Val Arg Gly Leu Thr Gly Pro Ile Gly Pro Pro Gly Pro Ala
785                 790                 795                 800

Gly Ala Pro Gly Asp Lys Gly Glu Ser Gly Pro Ser Gly Pro Ala Gly
            805                 810                 815

Pro Thr Gly Ala Arg Gly Ala Pro Gly Asp Arg Gly Glu Pro Gly Pro
            820                 825                 830
```

```
Pro Gly Pro Ala Gly Phe Ala Gly Pro Gly Ala Asp Gly Gln Pro
        835                 840                 845

Gly Ala Lys Gly Glu Pro Gly Asp Ala Gly Ala Lys Gly Asp Ala Gly
850                 855                 860

Pro Pro Gly Pro Ala Gly Pro Ala Gly Pro Pro Gly Pro Ile Gly Asn
865                 870                 875                 880

Val Gly Ala Pro Gly Ala Lys Gly Ala Arg Gly Ser Ala Gly Pro Pro
            885                 890                 895

Gly Ala Thr Gly Phe Pro Gly Ala Ala Gly Arg Val Gly Pro Pro Gly
            900                 905                 910

Pro Ser Gly Asn Ala Gly Pro Pro Gly Pro Pro Gly Pro Ala Gly Lys
        915                 920                 925

Glu Gly Gly Lys Gly Pro Arg Gly Glu Thr Gly Pro Ala Gly Arg Pro
930                 935                 940

Gly Glu Val Gly Pro Pro Gly Pro Pro Gly Pro Ala Gly Glu Lys Gly
945                 950                 955                 960

Ser Pro Gly Ala Asp Gly Pro Ala Gly Ala Pro Gly Thr Pro Gly Pro
            965                 970                 975

Gln Gly Ile Ala Gly Gln Arg Gly Val Val Gly Leu Pro Gly Gln Arg
        980                 985                 990

Gly Glu Arg Gly Phe Pro Gly Leu Pro Gly Pro Ser Gly Glu Pro Gly
        995                 1000                1005

Lys Gln Gly Pro Ser Gly Ala  Ser Gly Glu Arg Gly  Pro Pro Gly
    1010                1015                 1020

Pro Met Gly Pro Pro Gly Leu  Ala Gly Pro Pro Gly  Glu Ser Gly
    1025                1030                 1035

Arg Glu Gly Ala Pro Gly Ala  Glu Gly Ser Pro Gly  Arg Asp Gly
    1040                1045                 1050

Ser Pro Gly Ala Lys Gly Asp  Arg Gly Glu Thr Gly  Pro Ala Gly
    1055                1060                 1065

Pro Pro Gly Ala Pro Gly Ala  Pro Gly Ala Pro Gly  Pro Val Gly
    1070                1075                 1080

Pro Ala Gly Lys Ser Gly Asp  Arg Gly Glu Thr Gly  Pro Ala Gly
    1085                1090                 1095

Pro Ala Gly Pro Val Gly Pro  Ala Gly Ala Arg Gly  Pro Ala Gly
    1100                1105                 1110

Pro Gln Gly Pro Arg Gly Asp  Lys Gly Glu Thr Gly  Glu Gln Gly
    1115                1120                 1125

Asp Arg Gly Ile Lys Gly His  Arg Gly Phe Ser Gly  Leu Gln Gly
    1130                1135                 1140

Pro Pro Gly Pro Pro Gly Ser  Pro Gly Glu Gln Gly  Pro Ser Gly
    1145                1150                 1155

Ala Ser Gly Pro Ala Gly Pro  Arg Gly Pro Pro Gly  Ser Ala Gly
    1160                1165                 1170

Ala Pro Gly Lys Asp Gly Leu  Asn Gly Leu Pro Gly  Pro Ile Gly
    1175                1180                 1185

Pro Pro Gly Pro Arg Gly Arg  Thr Gly Asp Ala Gly  Pro Val Gly
    1190                1195                 1200

Pro Pro Gly Pro Pro Gly Pro  Pro Gly Pro Pro Gly  Pro Pro Ser
    1205                1210                 1215

Ala Gly Phe Asp Phe Ser Phe  Leu Pro Gln Pro Pro  Gln Glu Lys
    1220                1225                 1230

Ala His Asp Gly Gly Arg Tyr  Tyr Arg Ala Asp Asp  Ala Asn Val
```

```
                    1235                1240                1245

Val  Arg  Asp  Arg  Asp  Leu  Glu  Val  Asp  Thr  Thr  Leu  Lys  Ser  Leu
     1250                1255                1260

Ser  Gln  Gln  Ile  Glu  Asn  Ile  Arg  Ser  Pro  Glu  Gly  Ser  Arg  Lys
     1265                1270                1275

Asn  Pro  Ala  Arg  Thr  Cys  Arg  Asp  Leu  Lys  Met  Cys  His  Ser  Asp
     1280                1285                1290

Trp  Lys  Ser  Gly  Glu  Tyr  Trp  Ile  Asp  Pro  Asn  Gln  Gly  Cys  Asn
     1295                1300                1305

Leu  Asp  Ala  Ile  Lys  Val  Phe  Cys  Asn  Met  Glu  Thr  Gly  Glu  Thr
     1310                1315                1320

Cys  Val  Tyr  Pro  Thr  Gln  Pro  Ser  Val  Ala  Gln  Lys  Asn  Trp  Tyr
     1325                1330                1335

Ile  Ser  Lys  Asn  Pro  Lys  Asp  Lys  Arg  His  Val  Trp  Phe  Gly  Glu
     1340                1345                1350

Ser  Met  Thr  Asp  Gly  Phe  Gln  Phe  Glu  Tyr  Gly  Gly  Gln  Gly  Ser
     1355                1360                1365

Asp  Pro  Ala  Asp  Val  Ala  Ile  Gln  Leu  Thr  Phe  Leu  Arg  Leu  Met
     1370                1375                1380

Ser  Thr  Glu  Ala  Ser  Gln  Asn  Ile  Thr  Tyr  His  Cys  Lys  Asn  Ser
     1385                1390                1395

Val  Ala  Tyr  Met  Asp  Gln  Gln  Thr  Gly  Asn  Leu  Lys  Lys  Ala  Leu
     1400                1405                1410

Leu  Leu  Lys  Gly  Ser  Asn  Glu  Ile  Glu  Ile  Arg  Ala  Glu  Gly  Asn
     1415                1420                1425

Ser  Arg  Phe  Thr  Tyr  Ser  Val  Thr  Val  Asp  Gly  Cys  Thr  Ser  His
     1430                1435                1440

Thr  Gly  Ala  Trp  Gly  Lys  Thr  Val  Ile  Glu  Tyr  Lys  Thr  Thr  Lys
     1445                1450                1455

Thr  Ser  Arg  Leu  Pro  Ile  Ile  Asp  Val  Ala  Pro  Leu  Asp  Val  Gly
     1460                1465                1470

Ala  Pro  Asp  Gln  Glu  Phe  Gly  Phe  Asp  Val  Gly  Pro  Val  Cys  Phe
     1475                1480                1485

Leu

<210> SEQ ID NO 8
<211> LENGTH: 1389
<212> TYPE: PRT
<213> ORGANISM: Homo sapiens

<400> SEQUENCE: 8

Met  Ala  His  Ala  Arg  Val  Leu  Leu  Leu  Ala  Leu  Ala  Val  Leu  Ala  Thr
1                   5                   10                  15

Ala  Ala  Val  Ala  Val  Ala  Ser  Ser  Ser  Phe  Ala  Asp  Ser  Asn  Pro
              20                  25                  30

Ile  Arg  Pro  Val  Thr  Asp  Arg  Ala  Ala  Ser  Thr  Leu  Ala  Gln  Leu  Leu
          35                  40                  45

Gln  Glu  Glu  Thr  Val  Arg  Lys  Gly  Pro  Ala  Gly  Asp  Arg  Gly  Pro  Arg
     50                  55                  60

Gly  Glu  Arg  Gly  Pro  Pro  Gly  Pro  Pro  Gly  Arg  Asp  Gly  Glu  Asp  Gly
65                  70                  75                  80

Pro  Thr  Gly  Pro  Pro  Gly  Pro  Pro  Gly  Pro  Pro  Gly  Pro  Pro  Gly  Leu
              85                  90                  95

Gly  Gly  Asn  Phe  Ala  Ala  Gln  Tyr  Asp  Gly  Lys  Gly  Val  Gly  Leu  Gly
```

-continued

```
                100                 105                 110
Pro Gly Pro Met Gly Leu Met Gly Pro Arg Gly Pro Pro Gly Ala Ala
            115                 120                 125
Gly Ala Pro Gly Pro Gln Gly Phe Gln Gly Pro Ala Gly Glu Pro Gly
130                 135                 140
Glu Pro Gly Gln Thr Gly Pro Ala Gly Ala Arg Gly Pro Ala Gly Pro
145                 150                 155                 160
Pro Gly Lys Ala Gly Glu Asp Gly His Pro Gly Lys Pro Gly Arg Pro
            165                 170                 175
Gly Glu Arg Gly Val Val Gly Pro Gln Gly Ala Arg Gly Phe Pro Gly
            180                 185                 190
Thr Pro Gly Leu Pro Gly Phe Lys Gly Ile Arg Gly His Asn Gly Leu
            195                 200                 205
Asp Gly Leu Lys Gly Gln Pro Gly Ala Pro Gly Val Lys Gly Glu Pro
            210                 215                 220
Gly Ala Pro Gly Glu Asn Gly Thr Pro Gly Gln Thr Gly Ala Arg Gly
225                 230                 235                 240
Leu Pro Gly Glu Arg Gly Arg Val Gly Ala Pro Gly Pro Ala Gly Ala
            245                 250                 255
Arg Gly Ser Asp Gly Ser Val Gly Pro Val Gly Pro Ala Gly Pro Ile
            260                 265                 270
Gly Ser Ala Gly Pro Pro Gly Phe Pro Gly Ala Pro Gly Pro Lys Gly
            275                 280                 285
Glu Ile Gly Ala Val Gly Asn Ala Gly Pro Thr Gly Pro Ala Gly Pro
            290                 295                 300
Arg Gly Glu Val Gly Leu Pro Gly Leu Ser Gly Pro Val Gly Pro Pro
305                 310                 315                 320
Gly Asn Pro Gly Ala Asn Gly Leu Thr Gly Ala Lys Gly Ala Ala Gly
            325                 330                 335
Leu Pro Gly Val Ala Gly Ala Pro Gly Leu Pro Gly Pro Arg Gly Ile
            340                 345                 350
Pro Gly Pro Val Gly Ala Ala Gly Ala Thr Gly Ala Arg Gly Leu Val
            355                 360                 365
Gly Glu Pro Gly Pro Ala Gly Ser Lys Gly Glu Ser Gly Asn Lys Gly
            370                 375                 380
Glu Pro Gly Ser Ala Gly Pro Gln Gly Pro Pro Gly Pro Ser Gly Glu
385                 390                 395                 400
Glu Gly Lys Arg Gly Pro Asn Gly Glu Ala Gly Ser Ala Gly Pro Pro
            405                 410                 415
Gly Pro Pro Gly Leu Arg Gly Ser Pro Gly Ser Arg Gly Leu Pro Gly
            420                 425                 430
Ala Asp Gly Arg Ala Gly Val Met Gly Pro Pro Gly Ser Arg Gly Ala
            435                 440                 445
Ser Gly Pro Ala Gly Val Arg Gly Pro Asn Gly Asp Ala Gly Arg Pro
            450                 455                 460
Gly Glu Pro Gly Leu Met Gly Pro Arg Gly Leu Pro Gly Ser Pro Gly
465                 470                 475                 480
Asn Ile Gly Pro Ala Gly Lys Glu Gly Pro Val Gly Leu Pro Gly Ile
            485                 490                 495
Asp Gly Arg Pro Gly Pro Ile Gly Pro Ala Gly Ala Arg Gly Glu Pro
            500                 505                 510
Gly Asn Ile Gly Phe Pro Gly Pro Lys Gly Pro Thr Gly Asp Pro Gly
            515                 520                 525
```

-continued

```
Lys Asn Gly Asp Lys Gly His Ala Gly Leu Ala Gly Ala Arg Gly Ala
530                 535                 540
Pro Gly Pro Asp Gly Asn Asn Gly Ala Gln Gly Pro Pro Gly Pro Gln
545                 550                 555                 560
Gly Val Gln Gly Gly Lys Gly Glu Gln Gly Pro Ala Gly Pro Pro Gly
                565                 570                 575
Phe Gln Gly Leu Pro Gly Pro Ser Gly Pro Ala Gly Glu Val Gly Lys
                580                 585                 590
Pro Gly Glu Arg Gly Leu His Gly Glu Phe Gly Leu Pro Gly Pro Ala
                595                 600                 605
Gly Pro Arg Gly Glu Arg Gly Pro Pro Gly Glu Ser Gly Ala Ala Gly
610                 615                 620
Pro Thr Gly Pro Ile Gly Ser Arg Gly Pro Ser Gly Pro Pro Gly Pro
625                 630                 635                 640
Asp Gly Asn Lys Gly Glu Pro Gly Val Val Gly Ala Val Gly Thr Ala
                645                 650                 655
Gly Pro Ser Gly Pro Ser Gly Leu Pro Gly Glu Arg Gly Ala Ala Gly
                660                 665                 670
Ile Pro Gly Gly Lys Gly Glu Lys Gly Glu Pro Gly Leu Arg Gly Glu
                675                 680                 685
Ile Gly Asn Pro Gly Arg Asp Gly Ala Arg Gly His Ala Val
690                 695                 700
Gly Ala Pro Gly Pro Ala Gly Ala Thr Gly Asp Arg Gly Glu Ala Gly
705                 710                 715                 720
Ala Ala Gly Pro Ala Gly Pro Ala Gly Pro Arg Gly Ser Pro Gly Glu
                725                 730                 735
Arg Gly Glu Val Gly Pro Ala Gly Pro Asn Gly Phe Ala Gly Pro Ala
                740                 745                 750
Gly Ala Ala Gly Gln Pro Gly Ala Lys Gly Glu Arg Gly Gly Lys Gly
                755                 760                 765
Pro Lys Gly Glu Asn Gly Val Val Gly Pro Thr Gly Pro Val Gly Ala
770                 775                 780
Ala Gly Pro Ala Gly Pro Asn Gly Pro Pro Gly Pro Ala Gly Ser Arg
785                 790                 795                 800
Gly Asp Gly Gly Pro Pro Gly Met Thr Gly Phe Pro Gly Ala Ala Gly
                805                 810                 815
Arg Thr Gly Pro Pro Gly Pro Ser Gly Ile Ser Gly Pro Pro Gly Pro
                820                 825                 830
Pro Gly Pro Ala Gly Lys Glu Gly Leu Arg Gly Pro Arg Gly Asp Gln
                835                 840                 845
Gly Pro Val Gly Arg Thr Gly Glu Val Gly Ala Val Gly Pro Pro Gly
850                 855                 860
Phe Ala Gly Glu Lys Gly Pro Ser Gly Glu Ala Gly Thr Ala Gly Pro
865                 870                 875                 880
Pro Gly Thr Pro Gly Pro Gln Gly Leu Leu Gly Ala Pro Gly Ile Leu
                885                 890                 895
Gly Leu Pro Gly Ser Arg Gly Glu Arg Gly Leu Pro Gly Val Ala Gly
                900                 905                 910
Ala Val Gly Glu Pro Gly Pro Leu Gly Ile Ala Gly Pro Pro Gly Ala
                915                 920                 925
Arg Gly Pro Pro Gly Ala Val Gly Ser Pro Gly Val Asn Gly Ala Pro
930                 935                 940
```

```
Gly Glu Ala Gly Arg Asp Gly Asn Pro Gly Asn Asp Gly Pro Pro Gly
945                 950                 955                 960

Arg Asp Gly Gln Pro Gly His Lys Gly Glu Arg Gly Tyr Pro Gly Asn
            965                 970                 975

Ile Gly Pro Val Gly Ala Ala Gly Ala Pro Gly Pro His Gly Pro Val
                980                 985                 990

Gly Pro Ala Gly Lys His Gly Asn Arg Gly Glu Thr Gly Pro Ser Gly
        995                 1000                1005

Pro Val Gly Pro Ala Gly Ala Val Gly Pro Arg Gly Pro Ser Gly
    1010                1015                1020

Pro Gln Gly Ile Arg Gly Asp Lys Gly Glu Pro Gly Glu Lys Gly
    1025                1030                1035

Pro Arg Gly Leu Pro Gly Phe Lys Gly His Asn Gly Leu Gln Gly
    1040                1045                1050

Leu Pro Gly Ile Ala Gly His His Gly Asp Gln Gly Ala Pro Gly
    1055                1060                1065

Ser Val Gly Pro Ala Gly Pro Arg Gly Pro Ala Gly Pro Ser Gly
    1070                1075                1080

Pro Ala Gly Lys Asp Gly Arg Thr Gly His Pro Gly Thr Val Gly
    1085                1090                1095

Pro Ala Gly Ile Arg Gly Pro Gln Gly His Gln Gly Pro Ala Gly
    1100                1105                1110

Pro Pro Gly Pro Pro Gly Pro Pro Gly Pro Pro Gly Val Ser Gly
    1115                1120                1125

Gly Gly Tyr Asp Phe Gly Tyr Asp Gly Asp Phe Tyr Arg Ala Asp
    1130                1135                1140

Gln Pro Arg Ser Ala Pro Ser Leu Arg Pro Lys Asp Tyr Glu Val
    1145                1150                1155

Asp Ala Thr Leu Lys Ser Leu Asn Asn Gln Ile Glu Thr Leu Leu
    1160                1165                1170

Thr Pro Glu Gly Ser Arg Lys Asn Pro Ala Arg Thr Cys Arg Asp
    1175                1180                1185

Leu Arg Leu Ser His Pro Glu Trp Ser Ser Gly Tyr Tyr Trp Ile
    1190                1195                1200

Asp Pro Asn Gln Gly Cys Thr Met Glu Ala Ile Lys Val Tyr Cys
    1205                1210                1215

Asp Phe Pro Thr Gly Glu Thr Cys Ile Arg Ala Gln Pro Glu Asn
    1220                1225                1230

Ile Pro Ala Lys Asn Trp Tyr Arg Ser Ser Lys Asp Lys Lys His
    1235                1240                1245

Val Trp Leu Gly Glu Thr Ile Asn Ala Gly Ser Gln Phe Glu Tyr
    1250                1255                1260

Asn Val Glu Gly Val Thr Ser Lys Glu Met Ala Thr Gln Leu Ala
    1265                1270                1275

Phe Met Arg Leu Leu Ala Asn Tyr Ala Ser Gln Asn Ile Thr Tyr
    1280                1285                1290

His Cys Lys Asn Ser Ile Ala Tyr Met Asp Glu Thr Gly Asn
    1295                1300                1305

Leu Lys Lys Ala Val Ile Leu Gln Gly Ser Asn Asp Val Glu Leu
    1310                1315                1320

Val Ala Glu Gly Asn Ser Arg Phe Thr Tyr Thr Val Leu Val Asp
    1325                1330                1335

Gly Cys Ser Lys Lys Thr Asn Glu Trp Gly Lys Thr Ile Ile Glu
```

Tyr Lys Thr Asn Lys Pro Ser Arg Leu Pro Phe Leu Asp Ile Ala
1355                1360                1365

Pro Leu Asp Ile Gly Gly Ala Asp His Glu Phe Phe Val Asp Ile
1370                1375                1380

Gly Pro Val Cys Phe Lys
1385

<210> SEQ ID NO 9
<211> LENGTH: 2888
<212> TYPE: DNA
<213> ORGANISM: Artificial sequence
<220> FEATURE:
<223> OTHER INFORMATION: Synthetic sequence containing the coding
regions of the vascular signal sequence of barley gene for Thiol
protease aleurain precursor fused to the human Lysyl hydroxylase 3
and flanking regions

<400> SEQUENCE: 9

| | | | | | |
|---|---|---|---|---|---|
| gcgaattcgc | tagctatcac | tgaaaagaca | gcaagacaat | ggtgtctcga | tgcaccagaa | 60 |
| ccacatcttt | gcagcagatg | tgaagcagcc | agagtggtcc | acaagacgca | ctcagaaaag | 120 |
| gcatcttcta | ccgacacaga | aaaagacaac | cacagctcat | catccaacat | gtagactgtc | 180 |
| gttatgcgtc | ggctgaagat | aagactgacc | ccaggccagc | actaaagaag | aaataatgca | 240 |
| agtggtccta | gctccacttt | agctttaata | attatgtttc | attattattc | tctgcttttg | 300 |
| ctctctatat | aaagagcttg | tattttcatt | tgaaggcaga | ggcgaacaca | cacacagaac | 360 |
| ctccctgctt | acaaaccaga | tcttaaacca | tggctcacgc | tagggttttg | cttcttgctc | 420 |
| ttgctgttct | tgctactgct | gctgttgctg | tggcttcttc | aagttctttc | gctgattcta | 480 |
| acccaattag | gccagtgact | gatagagctg | cttctactct | tgctcaattg | agatctatgt | 540 |
| ctgatagacc | aaggggaagg | gatccagtta | atccagagaa | gttgcttgtg | attactgtgg | 600 |
| ctactgctga | gactgaagga | taccttagat | tccttaggag | tgctgagttc | ttcaactaca | 660 |
| ctgtgaggac | tcttggactt | ggagaagaat | ggaggggagg | agatgttgct | agaactgttg | 720 |
| gaggaggaca | gaaagtgaga | tggcttaaga | aagagatgga | gaagtacgct | gatagggagg | 780 |
| atatgattat | tatgttcgtg | gattcttacg | atgtgattct | tgctggatct | ccaactgagc | 840 |
| ttttgaagaa | attcgttcag | tctggatcta | ggcttctttt | tctgctgag  | tcttttttgtt | 900 |
| ggccagaatg | gggacttgct | gagcaatatc | agaagtggg  | aactggaaag | agattcctta | 960 |
| actctggagg | attcattgga | ttcgctacta | ctattcacca | gattgtgagg | cagtggaagt | 1020 |
| acaaggatga | cgatgatgat | cagcttttct | acactaggct | ttaccttgat | ccaggactta | 1080 |
| gggagaagtt | gtctcttaac | cttgatcaca | agtctaggat | tttccagaac | cttaacggtg | 1140 |
| ctcttgatga | ggttgtgctt | aagttcgata | ggaacagagt | gaggattagg | aacgtggctt | 1200 |
| acgatactct | tcctattgtg | gtgcatggaa | acggaccaac | aaaactccag | cttaactacc | 1260 |
| ttggaaacta | cgttccaaac | ggatggactc | agaaggagg  | atgtggattc | tgcaatcagg | 1320 |
| ataggagaac | tcttccagga | ggacaaccac | accaagagt  | tttccttgct | gtgttcgttg | 1380 |
| aacagccaac | tccattcctt | ccaagattcc | ttcagaggct | tcttcttttg | gattacccac | 1440 |
| cagatagggt | gacactttc  | cttcacaaca | acagaggtttt | ccacgagcca | cacattgctg | 1500 |
| attcttggcc | acagcttcag | gatcatttct | ctgctgtgaa | gttggttggt | ccagaagaag | 1560 |
| ctctttctcc | aggagaagct | agggatatgg | ctatggattt | gtgcaggcag | gatccagagt | 1620 |
| gcgagttcta | cttctctctt | gatgctgatg | ctgtgcttac | taaccttcag | actcttagga | 1680 |

```
ttcttattga ggagaacagg aaagtgattg ctccaatgct ttctaggcac ggaaagttgt    1740
ggtctaattt ctggggtgct ctttctcctg atgagtacta cgctagatca gaggactacg    1800
tggagcttgt tcagagaaag agagtgggag tttggaacgt tccttatatt tctcaggctt    1860
acgtgattag gggagatact cttaggatgg agcttccaca gagggatgtt ttctctggat    1920
ctgatactga tccagatatg gctttctgca agtctttcag ggataaggga attttccttc    1980 accttctaa ccagcatgag ttcggaagat tgcttgctac ttcaagatac gatactgagc    2040
accttcatcc tgatctttgg cagattttcg ataacccagt ggattggaag gagcagtaca    2100
ttcacgagaa ctactctagg gctcttgaag gagaaggaat tgtggagcaa ccatgcccag    2160
atgtttactg gttcccactt ctttctgagc aaatgtgcga tgagcttgtt gctgagatgg    2220
agcattacgg acaatggagt ggaggtagac atgaggattc taggcttgct ggaggatacg    2280
agaacgttcc aactgtggat attcacatga agcaagtggg atacgaggat caatggcttc    2340
agcttcttag gacttatgtg ggaccaatga ctgagtctct tttcccagga taccacacta    2400
aggctagggc tgttatgaac ttcgttgtga ggtatcgtcc agatgagcaa ccatctctta    2460
ggccacacca cgattcttct actttcactc ttaacgtggc tcttaaccac aagggacttg    2520
attatgaggg aggaggatgc cgtttcctta gatacgattg cgtgatttct tcaccaagaa    2580
agggatgggc tcttcttcat ccaggaaggc ttactcatta ccacgaggga cttccaacta    2640
cttggggaac tagatatatt atggtgtctt tcgtggatcc atgactgctt taatgagata    2700
tgcgagacgc ctatgatcgc atgatatttg ctttcaattc tgttgtgcac gttgtaaaaa    2760
acctgagcat gtgtagctca gatccttacc gccggtttcg gttcattcta atgaatatat    2820
cacccgttac tatcgtattt ttatgaataa tattctccgt tcaatttact gattgtccag    2880
aattcgcg                                                             2888
```

<210> SEQ ID NO 10
<211> LENGTH: 2689
<212> TYPE: DNA
<213> ORGANISM: Artificial sequence
<220> FEATURE:
<223> OTHER INFORMATION: Synthetic sequence containing the coding
      regions of the human Procollagen C-proteinase and flanking regions

<400> SEQUENCE: 10

```
agatctatcg atgcatgcca tggtaccgcg ccatggctca attggctgca acatcaaggc      60
ctgaaagagt ttggccagat ggtgttattc ctttcgttat tggtggaaac tttactggat     120
ctcagagagc agttttttaga caagctatga acattggga aaagcacact tgtgtgacat     180
tccttgaaag gactgatgaa gattcttata ttgtgttcac ataccgtcca tgtggatgct     240
gctcatatgt tggtagaagg ggaggaggtc cacaagcaat ttctattgga aaaaactgcg     300
ataagttcgg aattgtggtg catgaattgg gacatgttgt tggtttctgg cacgaacaca     360
caaggccaga tagggatagg cacgtgtcta ttgtgaggga aaacattcag ccaggtcaag     420
agtacaattt tcttaagatg gaacctcaag aggtggaatc tctcggagag acttacgact     480
tcgactccat catgcactac gcaaggaata ctttcagcag gggcatcttc ttggatacca     540
ttgtgcctaa gtacgaggtg aacggcgtta agccacctat tggtcaaagg actaggctct     600
ctaagggtga tattgcacag gctaggaagc tctacaaatg tccagcatgc ggagaaactc     660
ttcaggattc cactggcaac ttctcatctc cagagtaccc aaacggatac tctgctcata     720
tgcactgtgt ttggaggatc tcagtgactc ctggagagaa gatcatcctc aacttcactt     780
```

```
ccctcgatct ctatcgttct aggctctgtt ggtacgacta tgtggaagtg agagatggct    840
tctggagaaa ggctccactt agaggaaggt tctgcggatc taaacttcct gagccaatcg    900
tgtctactga ttccagattg tgggtggagt tcaggtcctc ttctaattgg gttggcaagg    960
gcttttttgc tgtgtacgag gctatttgtg gcggcgacgt gaaaaaggac tacggacata   1020
ttcaaagtcc aaattaccca gatgattacc gtccttcaaa agtgtgtatt tggaggattc   1080
aagtgagtga gggtttccat gttggattga cattccaatc tttcgaaatt gagagacacg   1140
attcatgcgc atacgattat ttggaagtga gagatggaca ctctgaatct tctacactta   1200
ttggaaggta ctgcggttat gagaaacctg atgatattaa gtctacttct agtaggttgt   1260
ggcttaaatt tgtgtcagat ggttctatta acaaggctgg tttcgcagtg aacttcttca   1320
aggaagtgga tgaatgctca agacctaaca gaggaggatg tgagcaaaga tgccttaaca   1380
ctttgggaag ttacaagtgt tcttgcgatc ctggatacga gttggctcct gataagagaa   1440
gatgcgaagc tgcttgcggt ggttttttga caaaattgaa cggatctatt acttctcctg   1500
gatggccaaa agagtaccca cctaataaga attgcatttg gcagcttgtt gcacctactc   1560
agtaccgtat ttcattgcaa ttcgattttt tcgagactga gggtaatgat gtgtgcaagt   1620
acgatttcgt ggaagtgaga tcaggtctta ctgctgatag taaattgcac ggaaagttct   1680
gcggatctga aaaccagaa gtgattacat cacagtacaa caatatgagg gtggagttca   1740
aatctgataa tactgtttct aaaaaaggtt ttaaggcaca tttcttttct gataaggacg   1800
agtgctctaa agataatggt ggttgccagc aggattgcgt gaacacattc ggttcatatg   1860
agtgccaatg ccgtagtgga tttgttcttc acgataacaa acatgattgc aaagaggcag   1920
gttgcgatca aaggtgaca tctacttcag gtactatcac atctccaaac tggcctgata   1980
agtatccttc aaaaaaagaa tgtacatggg caatttcttc tacaccaggt catagggtta   2040
agttgacatt catggagatg gatattgaga gtcaaccaga gtgcgcttat gatcatcttg   2100
aggtgttcga tggaagggat gctaaggctc ctgttcttgg tagattctgt ggtagtaaaa   2160
agccagaacc agtgcttgca acaggatcta ggatgttcct tagattctac tctgataact   2220
cagttcagag gaaaggattc caagctagtc acgcaactga atgcggtgga caagttagag   2280
cagatgttaa gactaaggat ctttactcac acgcacagtt cggagataac aactaccctg   2340
gaggagttga ttgcgagtgg gttattgtgg ctgaagaggg atacggagtt gagcttgttt   2400
tccagacatt cgaggtggag gaggaaactg attgcggtta cgattatatg gaacttttg    2460 atggatacga tagtactgct ccaagacttg gaaggtattg tggtagtggt ccaccagaag   2520
aggtgtactc agctggagat agtgttcttg ttaagttcca cagtgatgat acaattacta   2580
agaagggatt ccatcttaga tatacttcaa ctaagtttca ggatactctt cattctagga   2640
agtaatgagc tcgcggccgc atccaagctt ctgcagacgc gtcgacgtc               2689
```

<210> SEQ ID NO 11
<211> LENGTH: 2912
<212> TYPE: DNA
<213> ORGANISM: Artificial sequence
<220> FEATURE:
<223> OTHER INFORMATION: Synthetic sequence containing the coding
      regions of the human Procollagen I N-proteinase and flanking
      regions

<400> SEQUENCE: 11

```
gcgccatggc tcaattgagg agaagggcta ggagacacgc agctgatgat gattacaaca     60
```

-continued

```
ttgaagtttt gcttggtgtt gatgatagtg tggtgcaatt ccacggaaaa gagcatgttc    120
agaaatatct tttgacactt atgaatattg tgaacgaaat ctaccatgat gagtctttgg    180
gagcacacat taacgtggtt cttgtgagga ttattcttct ttcatacggt aaatctatgt    240
cacttattga gattggaaac ccttctcagt ctcttgagaa tgtgtgcaga tgggcatacc    300
ttcaacagaa gcctgatact ggacacgatg agtatcacga tcacgctatt ttccttacaa    360
ggcaggattt cggtccaagt ggaatgcaag gatatgctcc tgttactggt atgtgccacc    420
ctgttaggtc ttgtacactt aaccacgagg atggtttttc atctgctttc gtggtggctc    480
atgagacagg tcatgttttg ggaatggaac atgatggaca gggtaataga tgtggagatg    540
aagtgagact tggttcaatt atggctcctc ttgttcaagc tgcttttcat aggttccact    600
ggagtaggtg ttcacagcaa gagttgagta gatacccttca ttcttacgat tgcttgcttg    660
atgatccatt tgctcatgat tggccagctt tgcctcaact tcctggattg cactactcta    720
tgaacgagca gtgcagattt gatttcggtc ttggttacat gatgtgcaca gctttcagga    780
ctttcgatcc atgcaaacag ttgtggtgtt cacacccaga taacccatat ttctgtaaaa    840
caaaaaaagg tccaccactt gatggtacta tgtgcgcacc tggaaagcac tgcttcaagg    900
gacactgcat ttggcttact cctgatattc ttaaaaggga tggatcatgg ggagcttggt    960
ctccattcgg aagttgctca agaacttgcg gaacaggtgt taagtttaga actaggcagt   1020
gcgataatcc acaccctgct aatggtggta gaacttgctc tggacttgct tacgattttc   1080
agttgtgttc taggcaagat tgccctgata gtcttgctga ttttagagaa gagcaatgta   1140
gacagtggga tctttacttt gagcacggcg acgctcagca ccactggctt ccacacgagc   1200
atagagatgc aaaagaaagg tgtcaccttt attgcgagag tagagagact ggagaggtgg   1260
tgtcaatgaa gagaatggtg cacgatggta caaggtgttc ttataaggat gcattctctt   1320
tgtgtgtgag gggagattgc aggaaagtgg gttgtgatgg agtgattgga tctagtaagc   1380
aagaagataa gtgcggagtg tgcggaggag ataactctca ttgcaaggtt gtgaaaggaa   1440
cttttacaag atcaccaaaa aaacacggtt acattaagat gttcgaaatt cctgctggag   1500
caaggcattt gcttattcag gaagtggatg caacatctca ccacttggca gtgaaaaacc   1560
ttgagactgg aaaattcatt ttgaacgagg agaacgatgt tgatgcatct agtaagactt   1620
tcattgcaat gggtgttgaa tgggagtata gggatgagga tggaagggaa acacttcaaa   1680
caatgggtcc tcttcatgga acaattactg tgttggtgat tccagtggga gatacaaggg   1740
tgtcattgac atacaagtat atgattcacg aggatagtct taacgttgat gataacaacg   1800
ttttggaaga agattctgtg gtttacgagt gggctcttaa gaaatggtca ccttgctcta   1860
agccatgtgg tggaggaagt cagttcacta agtatggttg taggaggagg cttgatcata   1920
agatggttca tagggggattt tgcgcagcac ttagtaagcc aaaggcaatt aggagggctt   1980
gtaaccctca agaatgctca caaccagttt gggtgacagg agagtgggag ccatgttcac   2040
aaacatgcgg aagaactgga atgcaagtta gatcagttag atgcattcaa cctcttcatg   2100
ataacactac aagaagtgtg cacgcaaaac actgtaacga tgctaggcca gagagtagaa   2160
gagcttgctc tagggaactt tgccctgta gatggagggc aggaccttgg agtcagtgct   2220
ctgtgacatg tggaaacggt actcaggaaa gacctgttcc atgtagaact gctgatgata   2280
gtttcggaat tgtcaggag gaaaggccag aaacagctag gacttgtaga cttggacctt   2340
gtcctaggaa tatttctgat cctagtaaaa aatcatacgt ggtgcaatgg ttgagtaggc   2400
cagatccaga ttcaccaatt aggaagattt cttcaaaagg acactgccag ggtgataaga   2460
```

| | | |
|---|---|---|
| gtattttctg cagaatggaa gttcttagta ggtactgttc tattccaggt tataacaaac | 2520 |
| tttcttgtaa gagttgcaac ttgtataaca atcttactaa cgtggagggt agaattgaac | 2580 |
| ctccaccagg aaagcacaac gatattgatg tgtttatgcc tactcttcct gtgccaacag | 2640 |
| ttgcaatgga agttagacct tctccatcta ctccacttga ggtgccactt aatgcatcaa | 2700 |
| gtactaacgc tactgaggat cacccagaga ctaacgcagt tgatgagcct tataagattc | 2760 |
| acggacttga ggatgaggtt cagccaccaa accttattcc taggaggcca agtccttacg | 2820 |
| aaaaaactag aaatcagagg attcaggagc ttattgatga gatgaggaaa aaggagatgc | 2880 |
| ttggaaagtt ctaatgagct cgcggccgca tc | 2912 |

<210> SEQ ID NO 12
<211> LENGTH: 4467
<212> TYPE: DNA
<213> ORGANISM: Homo sapiens

<400> SEQUENCE: 12

| | | |
|---|---|---|
| atggctcacg ctcgtgttct cctcctcgct ctcgctgttt tggcaacagc tgctgtggct | 60 |
| gtggcttcta gttcttcttt tgctgattca aaccctatta gacctgttac tgatagagca | 120 |
| gcttccactt tggctcaatt gcaagaggag ggccaggttg agggccaaga tgaggatatc | 180 |
| cctccaatta catgcgtgca aaatggcttg cgttaccacg atagggatgt gtggaaacct | 240 |
| gaaccttgtc gtatctgtgt gtgtgataac ggcaaggtgc tctgcgatga tgttatctgc | 300 |
| gatgagacaa aaaattgccc tggcgctgaa gttcctgagg cgagtgttg ccctgtgtgc | 360 |
| cctgatggtt ccgagtcccc aactgatcag gaaactactg gcgtggaggg cccaaaagga | 420 |
| gatactggtc cacgtggtcc taggggtcca gcaggtcctc caggtagaga tggtattcca | 480 |
| ggccagcctg gattgccagg accaccaggc ccacctggcc caccaggacc tcctggtctt | 540 |
| ggtggaaatt tcgctccaca actctcttat ggctatgatg agaagtcaac aggtggtatt | 600 |
| tccgttccag gtcctatggg accatccgga ccaagaggtc tcccaggtcc tccaggtgct | 660 |
| cctggacctc aaggctttca aggacctcca ggcgaaccag gagaaccagg cgcttctgga | 720 |
| ccaatgggcc caagggggacc acctggccca ccaggaaaaa atggcgatga tggcgaagct | 780 |
| ggaaagcctg gtcgtcctgg agagagaggt cctcctggcc cacagggtgc aagaggcttg | 840 |
| ccaggaactg ctggcttgcc tggaatgaag ggacatgggg gcttctccgg cctcgatggc | 900 |
| gctaagggtg atgctggccc tgctggacca aagggcgagc caggttcccc tggagaaaac | 960 |
| ggtgctcctg gacaaatggg tcctcgtgga cttccaggaa aaggggtcg tccaggcgct | 1020 |
| ccaggaccag caggtgctag gggaaacgat ggtgcaacag cgctgctgg ccctcctggc | 1080 |
| ccaactggtc ctgctggccc tccaggattc ccaggcgca ttggagctaa aggagaagca | 1140 |
| ggaccacagg gcctaggggg ttctgaagga cctcagggtg ttagaggtga accaggtcct | 1200 |
| ccaggcccag ctggagcagc tggtccagca ggaaatccag tgctgatgg tcaacctgga | 1260 |
| gctaagggcg ctaatggcgc accaggtatc gcaggcgcac caggttttcc tggcgctaga | 1320 |
| ggcccaagtg gtcctcaagg accaggtgga ccaccaggtc caaaaggcaa ttctggcgaa | 1380 |
| cctggcgctc aggttctaa aggagatact ggtgctaaag gcgaaccagg acctgttggt | 1440 |
| gttcagggtc ctcctggtcc tgctggagaa gaggaaaaa gaggtgctcg tggagaacca | 1500 |
| ggaccaactg gacttcctgg acctcctggt gaacgtggcg gacctggctc aagggggttc | 1560 |
| cctggagctg atggagtggc aggtccaaaa ggccctgctg gagagagagg ttcaccaggt | 1620 |

```
ccagctggtc ctaagggctc ccctggtgaa gcaggtagac caggcgaagc aggattgcca    1680
ggcgcaaagg gattgacagg ctctcctggt agtcctggcc cagatggaaa aacaggccca    1740
ccaggtccag caggacaaga tggacgtcca ggcccaccag gtcctcctgg agcaagggga    1800
caagctggcg ttatgggttt tccaggacct aaaggtgctg ctggagagcc aggaaaggca    1860
ggtgaaagag gagttcctgg tccaccagga gcagtgggtc ctgctggcaa agatggtgaa    1920
gctggagcac agggccctcc aggccctgct ggcccagctg gcgaacgtgg agaacaaggc    1980
ccagctggta gtccaggatt tcaaggattg cctggccctg ctggccctcc aggagaagca    2040
ggaaaacctg gagaacaagg agttcctggt gatttgggag cacctggacc ttcaggagca    2100
cgtggtgaaa gaggcttccc tggcgagagg ggtgttcaag gtccaccagg tccagcagga    2160
cctagaggtg ctaatggcgc tcctggcaac gatggagcaa aggtgatgc tggtgctcct    2220 ggcgcacctg gaagtcaggg tgctcctgga ttgcaaggaa tgcctggaga gagggtgct    2280 gctggcttgc caggcccaaa gggcgatagg ggtgatgctg gaccaaaagg tgctgatgga    2340
tccccaggaa aagatggagt tcgtggtctt actggcccaa tcggacctcc aggccctgct    2400
ggcgctccag gtgataaggg cgaaagtggc ccaagtggac ctgctggacc tactggtgct    2460
agaggtgcac ctggtgatag gggtgaacct ggaccacctg gtccagctgg ttttgctggt    2520
cctcctggag ctgatggaca acctggcgca aagggtgaac aggtgatgc tggcgcaaag    2580 ggagatgctg gtccacctgg acctgctggt ccagcaggcc ccctgggcc aatcggtaat    2640 gttggagcac aggtgctaa gggagctagg ggttccgctg gtccacctgg agcaacagga    2700
tttccaggcg ctgctggtag agttggccca ccaggcccat ccggaaacgc aggccctcct    2760
ggtcctccag gtcctgctgg caaggagggt ggcaaaggac caaggggcga actggccct    2820 gctggtagac ctggcgaagt tggccctcct ggaccaccag gtccagcagg agaaaaaggt    2880
tccccaggag ctgatggccc agctggtgct ccaggaactc caggccctca aggtattgct    2940
ggacagagag gcgttgtggg actccctggt caaaggggag agagaggatt tccaggcttg    3000
ccaggaccta gtggagaacc tggaaaacaa ggcccatcag gcgctagtgg agagcgtgga    3060
cctcctggcc ctatgggacc tcctggattg ctggcccac ctggcgaatc aggtcgtgaa    3120
ggcgcaccag gcgcagaagg atcacctgga agagatggat cccctggtgc taaaggcgat    3180
cgtggagaaa ctggtccagc aggcccacca ggcgcaccag gtcacctgg cgctccagga    3240 cctgtgggac cagctggaaa atccggagat aggggcgaga caggcccagc aggaccagct    3300
ggacctgttg gccctgctgg cgctcgtgga ccagcaggac ctcaaggacc aaggggagat    3360
aagggagaaa caggcgaaca aggcgatagg ggcattaagg gtcataggggg ttttagtggc    3420 ctccaggggtc ctcctggccc acctggatca ccaggagaac agggaccatc tggtgcttcc    3480
ggcccagctg gtccaagagg acctccagga tcagctggtg cacctggaaa agatggtctt    3540
aacggtctcc caggaccaat cggccctcca ggacctagag gaagaacagg agatgctggc    3600
cctgttggcc ctcaggacc tcctggtcca ccagtccac ctggtcctcc atcagctgga    3660
ttcgattttt catttcttcc acagccacca caagagaaag ctcacgatgg cggcagatat    3720
taccgtgctg atgatgctaa cgttgttagg gatagagatt tggaagtgga tacaactttg    3780
aaatccctct cccagcaaat tgaaaacatt agatctccag aaggttcacg taaaaaccca    3840
gctagaacat gtcgtgattt gaaaatgtgt cactccgatt ggaaaagtgg tgaatactgg    3900
attgatccaa atcagggctg taatctcgat gctatcaaag ttttctgtaa catggaaaca    3960
ggcgaaacat gcgtttatcc tactcaacct tccgtggctc agaaaaattg gtacatctca    4020
```

| | | |
|---|---|---|
| aaaaatccta aagataagag gcacgtttgg ttcggtgaaa gtatgactga tggatttcaa | 4080 | |
| tttgagtacg gcggtcaagg tagtgatcca gctgatgtgg ctattcaact cacatttttg | 4140 | |
| cgtcttatgt ccacagaggc atcacaaaac atcacttacc actgcaaaaa cagtgtggct | 4200 | |
| tatatggatc aacaaacagg aaaccttaag aaggctcttc ttttgaaggg ctcaaacgag | 4260 | |
| attgagatta gagcagaggg caactcaagg tttacttatt cagttactgt tgatggctgc | 4320 | |
| acttcacata ctggcgcttg ggtaaaaaca gttatcgagt ataagactac aaaaacatca | 4380 | |
| agactcccaa tcattgatgt tgctcctctc gatgttggcg ctcctgatca agagttcggt | 4440 | |
| tttgatgtgg gcccagtttg tttcctc | 4467 | |

<210> SEQ ID NO 13
<211> LENGTH: 4167
<212> TYPE: DNA
<213> ORGANISM: Homo sapiens

<400> SEQUENCE: 13

| | | |
|---|---|---|
| atggctcacg ctcgtgttct cctcctcgct ctcgctgttt tggcaacagc tgctgtggct | 60 | |
| gtggcttcaa gttctagttt tgctgattcc aacccaattc gtccagttac tgatagagca | 120 | |
| gcttccactt tggctcaatt gcttcaagaa gaaactgtga ggaagggccc tgctggcgat | 180 | |
| aggggcccta ggggcgaaag gggtccacca ggacctccag gcagggatgg cgaagatggt | 240 | |
| ccaactggcc ctcctggacc tcctggccct ccagggccac ccggcttggg cggaaacttc | 300 | |
| gcagctcaat acgatggcaa gggtgttggt cttggtcctg gtcctatggg cttgatggga | 360 | |
| cctagaggcc cacctggtgc tgctggtgct cctggaccac agggttttca gggaccagct | 420 | |
| ggcgagccag gagagccagg ccaaacagga ccagctggtg caaggggacc tgctggacct | 480 | |
| cctggaaaag ctggtgaaga tggtcaccca ggcaaaccag gacgtcctgg cgaaagaggt | 540 | |
| gttgttggac acaaggcgc tagggggattt ccaggtacac ctggattgcc aggttttaag | 600 | |
| ggcattcgtg gtcataacgg cctcgatgga ttgaagggac agcctggcgc acctggcgtt | 660 | |
| aagggtgaac ctggagcacc aggtgaaaac ggtactcctg ccagactggt gcaagagga | 720 | |
| ctcccaggtg aaaggggtag agttggtgct cctggacctg ctggagctag gggtagtgat | 780 | |
| ggtagtgttg gtcctgtggg ccctgctggt ccaatcggtt ccgctggccc acctggattc | 840 | |
| ccaggcgctc caggacctaa aggagaaatc ggtgctgtgg gtaacgcagg tcctactggt | 900 | |
| ccagcaggtc ctcgtggaga agtgggattg ccaggacttt ctggtccagt gggccctcca | 960 | |
| ggcaaccctg gagctaacgg cttgacagga gctaaaggcg cagcaggact ccctggagtg | 1020 | |
| gctggcgcac caggattgcc tggtccaagg ggtatcccag ccctgttgg cgcagctgga | 1080 | |
| gctactggtg cacgtggact tgttggcgaa ccaggccctg ctggatcaaa aggcgagtct | 1140 | |
| ggaaataagg gagaacctgg ttctgctgga cctcaaggtc ctcctggacc ttctggagaa | 1200 | |
| gaaggaaaaa ggggaccaaa tggcgaggct ggatcagcag gtcccaccag gacacctgga | 1260 | |
| cttcgtggat cccctggtag tagaggactt ccaggcgctg atggtagagc aggcgttatg | 1320 | |
| ggaccaccag gaagtagagg agcatccggt ccagcaggag ttagggtcc taacggagat | 1380 | |
| gctggtagac aggtgaacc aggtcttatg gcccaaggg gctcccag tagtccagga | 1440 | |
| aatatcggcc ctgctggaaa agaaggccct gttggacttc aggtattga tggacgtcct | 1500 | |
| ggccctattg gccagcagg tgcaagagga gaacctggca atattggatt tccaggacca | 1560 | |
| aagggtccaa caggcgatcc tggaaaaaat ggagataagg gtcatgctgg attggcaggc | 1620 | |

```
gcaaggggcg ctcctggtcc agatggaaac aacggcgcac agggtccacc tggccctcag    1680
ggtgttcaag gcggaaaagg cgaacaaggc ccagctggac caccaggctt tcaaggcttg    1740
ccaggaccaa gtggtccagc aggtgaagtt ggcaagccag gcgagcgtgg acttcatggc    1800
gagtttggac tccctggacc agcaggacca aggggtgaaa gaggccctcc tggagagagt    1860
ggcgctgctg gaccaacagg cccaatcggt agtagaggtc ctagtggacc tccaggccca    1920
gatggaaata agggtgaacc aggagttgtg ggcgctgttg aacagctggt cccttcagga    1980
ccatcaggac tcccaggcga gagaggcgct gctggcattc ctggaggaaa aggtgaaaaa    2040
ggcgaacctg gcctccgtgg cgaaatcgga atcctggacg tgatggtgc tcgtggtgca     2100
cacggcgctg tgggcgctcc aggccctgct ggtgctactg gtgatagagg agaggctggc    2160
gcagctggcc cagcaggtcc tgctggccca aggggtagtc ctggtgaaag aggcgaagtt    2220
ggacctgctg gccctaacgg cttttgctggc cctgctggag cagcaggtca acctggcgct    2280
aaaggtgaaa ggggcggaaa gggcccaaaa ggtgaaaatg gcgttgtggg accaactggt    2340
ccagtgggcg cagctggacc tgctggtcca aatggaccac caggaccagc aggtagtaga    2400
ggagatggtg gacctccagg aatgacaggt tttccaggtg ctgctggtag aacaggacct    2460
cctggtccta gtggtatttc tggtccacca ggaccaccag gtcctgctgg aaaagaagga    2520
ttgaggggtc cacgtggtga tcaaggacca gtgggcagaa ctggtgaagt tggcgcagtg    2580
ggaccacctg gttttgctgg agaaaagggc ccttctggag aggcaggaac agctggtcct    2640
cctggtacac ctggaccctca aggactttttg ggtgcacctg gtattctcgg attgccagga    2700
agtaggggcg aacgtggact tcctggcgtg cagggagca ttggagaacc tggccctctc     2760
ggaatcgcag gcccaccagg cgcaagagga ccaccaggag ctgttggatc accaggcgtg    2820
aatggtgcac ctggcgaggc tggtcgtgat ggaaacccag gaaatgatgg cccaccagga    2880
agagatggtc aacctggaca caaaggcgag aggggctacc aggaaatat tggcccagtt     2940
ggtgctgctg gcgcaccagg cccacacggt ccagttggac cagcaggaaa acacggtaat    3000
cgtggcgaaa caggcccttc aggcccagtg ggacctgctg gtgctgttgg cccaagagga    3060
ccatctggac ctcaaggcat tagaggcgat aaggagagc ctggcgaaaa aggacctaga     3120
ggcttgcctg gttttaaagg acacaacggt ctccaaggac ttccaggtat cgctggtcat    3180
catggagatc agggtgctcc tggatcagtg ggtccagcag gtcctagagg cccagcaggc    3240
ccttccggtc cagcaggaaa ggatggacgt actggccacc ctggaactgt gggccctgct    3300
ggaattagag gtcctcaagg tcatcagggc cctgctggcc ctccaggtcc accaggtcct    3360
ccaggcccac caggagtttc aggtggtggt tacgattttg gttacgatgg tgattttttac    3420
cgtgctgatc aacctagaag tgctccttct ctccgtccta aagattatga agttgatgct    3480
actttgaaat cacttaacaa ccagattgag actcttctca cacctgaggg atcaagaaag    3540
aatccagcac gtacatgccg tgatctcaga cttagtcacc cagagtggtc aagtggctat    3600
tattggattg atcctaatca gggttgtaca atggaggcta tcaaagttta ctgtgatttt    3660
ccaactggag agacatgtat tagggcacaa cctgagaaca ttccagctaa aaattggtat    3720
cgttcctcta agataagaa acatgtttgg ctcggagaga ctattaacgc tggttctcag    3780
ttcgagtata atgttgaggg cgttacttct aaagagatgg caactcagct cgcttttatg    3840
agattgctcg ctaactacgc atcccaaaac atcacttatc actgcaaaaa ttccattgca    3900
tatatggatg aggagacagg aaatttgaag aaagcagtta ttctccaagg tagtaacgat    3960
gttgagcttg tggctgaggg aaatagtaga ttcacttaca cagttttggt ggatggatgc    4020
```

```
tcaaagaaaa ctaatgagtg gggcaagaca atcattgagt acaagacaaa taagccttct    4080
aggctcccat ttctcgatat tgcacctctt gatatcggag gagctgatca cgagtttttt    4140
gttgatatcg gacctgtttg ttttaag                                        4167
```